United States Patent
Lal et al.

(10) Patent No.: US 7,834,052 B2
(45) Date of Patent: Nov. 16, 2010

(54) FUSED TRICYCLIC COMPOUNDS AS INHIBITORS OF TUMOR NECROSIS FACTOR-ALPHA

(75) Inventors: Bansi Lal, Mumbai (IN); Usha Ghosh, Mumbai (IN); Swati Bal-Tembe, Mumbai (IN); Tulsidas More, Mumbai (IN); Pravin Gagare, Mumbai (IN); Sunil Jadhav, Mumbai (IN); Shashikant Patil, Mumbai (IN)

(73) Assignee: Piramal Life Sciences Limited, Mumbai (IN)

( * ) Notice: Subject to any disclaimer, the term of this patent is extended or adjusted under 35 U.S.C. 154(b) by 615 days.

(21) Appl. No.: 11/667,580

(22) PCT Filed: Nov. 8, 2005

(86) PCT No.: PCT/IB2005/053654

§ 371 (c)(1),
(2), (4) Date: May 10, 2007

(87) PCT Pub. No.: WO2006/051477

PCT Pub. Date: May 18, 2006

(65) Prior Publication Data

US 2007/0299050 A1    Dec. 27, 2007

Related U.S. Application Data

(60) Provisional application No. 60/637,217, filed on Dec. 17, 2004.

(30) Foreign Application Priority Data

Nov. 10, 2004   (IN) .................................. 1226/2004

(51) Int. Cl.
  *A61K 31/38*   (2006.01)
  *C07D 497/00*   (2006.01)
(52) U.S. Cl. .................................................... 514/431
(58) Field of Classification Search ................. 514/431; 540/1
  See application file for complete search history.

(56) References Cited

U.S. PATENT DOCUMENTS

| 4,431,808 A | 2/1984 | Protiva et al. |
| 5,036,067 A | 7/1991 | Girard et al. |
| 2003/0171585 A1 | 9/2003 | Scott et al. |

FOREIGN PATENT DOCUMENTS

| GB | 1 505 085 | 3/1978 |
| JP | 8 119920 | 5/1996 |
| JP | 90 40662 | 2/1997 |
| JP | 11 130772 | 5/1999 |
| WO | WO 96/31497 | 10/1996 |

OTHER PUBLICATIONS

Palladino et al., "Anti-TNF-α Therapies: The Next Generation." *Nature Reviews* 2(2003): 736-746.
Yale et al., "Novel Polycyclic Heterocycles, Derivatives of 5,11-Dihydrodibenz[b,e][1,4]oxazepine and 5,11-Dihydrodibenzo[b,e][1,4]thiazepine." *Journal of Medicinal Chemistry* 13, 4(1970): 713-722.
Oda et al., "Clevage of Vinyl Carbon-Silicon Bond with Tetrabutylammonium Flouride." *Tetrahedron* 41(1985): 3257-3268.
Baruah, Robindra N., "An efficient system: Cobalt(II) chloride hexahydrate-zinc-dimethylformamide-water for reduction of nitroarenes." *Indian Journal of Chemistry* 33B (1994): 758.
Overman et al., "The Reduction of Aryl Disulfides with Triphenylphosphine and Water." *Synthesis* (1974): 59-60.
Ackrell et al., "Synthesis and Antiinflammatory Activity of 6,11-Dihydro-11-oxodibenzo[*b,e*]thiepinalkanoic Acids and Related Compounds." *Journal of Medicinal Chemistry* 21,10(1978): 1035-1044.
Wilson et al., "A convenient human whole blood culture system for studying the regulation of tumour necrosis factor release by bacterial lipopolysaccharide." *Journal of Immunological Methods* 139(1991): 233-240.
Henry et al., "Potent Inhibitors of the Map Kinase p38." *Bioorganic & Medicinal Chemistry Letters* 8(1998): 3335-3340.
Brennan et al., "Inhibitory Effect of TNFα Antibodies on Synovial Cell Interleukin-1 Production in Rheumatoid Arthritis." *The Lancet* (1989): 244-247.

(Continued)

*Primary Examiner*—Taofiq A Solola
(74) *Attorney, Agent, or Firm*—Megan M. Miller

(57) ABSTRACT

Compounds of formula 1:

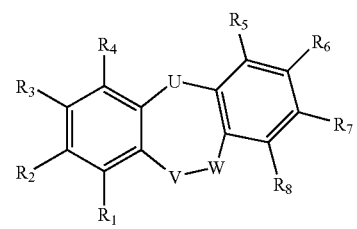

are disclosed, wherein V is $CH_2$; W is $S(O)_m$; m is the integer 0, 1 or 2; U is O, C(O), $CR_{13}R_{14}$ or $NR_{15}$; where $R_{13}$ is H, alkyl; $R_{14}$ is H, OH, $OR_{13}$ or $OCOR_{13}$; $R_{15}$ is H, alkyl, cycloalkyl, alkenyl, $C(O)R_{13}$, $C(O)OR_{13}$ or alkylaminocarbonyl; $R_1$, $R_2$, $R_3$, $R_4$, $R_5$, $R_6$, $R_7$ and $R_8$ are as defined herein. These compounds are inhibitors of tumor necrosis factor-alpha (TNF-α) and are useful as medicaments for the treatment and prevention of disorders caused by increased TNF-α activity, in particular inflammations.

14 Claims, No Drawings

OTHER PUBLICATIONS

Fukuda et al., "A novel dual regulator of tumor necrosis factor-α and interleukin-10 protects mice from endotoxin-induced shock." *European Journal of Pharmacology* 391(2000): 317-320.

Sindelar et al., "Butaclamol-Like Neuroleptic Agents: Synthesis of 1-(11*H*-DIBENZ[*b,f*]-1,4-Oxathiepin-11-YL)Methyl-4-Isobutylpiperdin-4-OL and of Some Related Compounds." *Collection of Czechoslocak Chemical Communications* 50,7(1985): 1484-1497.

Sindelar et al., "Tricyclic Psychotropic Agents Containing Two Chalcogen Atoms in the Central Ring: Derivatives of 11H-Dibenz[*b,f*]-1,4-Oxathiepin." *Collection of Czechoslovak Chemical Communications* 47(1982): 967-983.

PCT International Search Report for PCT/IB2005/053654, Jun. 6, 2006.

FUSED TRICYCLIC COMPOUNDS AS INHIBITORS OF TUMOR NECROSIS FACTOR-ALPHA

CROSS-REFERENCE TO RELATED APPLICATIONS

This application is related to our copending PCT application entitled: 'Tricyclic guanidine derivatives as sodium-proton exchange inhibitors', filed on the same date as the present application.

FIELD OF THE INVENTION

The present invention relates to novel condensed tricyclic compounds, which are inhibitors of Tumor Necrosis Factor-alpha (TNF-$\alpha$), to processes for their preparation, pharmaceutical compositions containing them and their use in medicines for treatment and prevention of disorders caused by increased TNF-$\alpha$ activity, such as inflammations.

BACKGROUND OF THE INVENTION

Tumor Necrosis Factor-$\alpha$ (TNF-$\alpha$), a pleiotropic cytokine, is produced mainly by macrophages, but other types of cells also produce it. TNF-$\alpha$ demonstrates beneficial as well as pathological activities. It has both growth stimulating effects and growth inhibitory properties, besides being self-regulatory. The beneficial functions of TNF-$\alpha$ include maintaining homeostasis by regulating the body's circadian rhythm, mounting an immune response to bacterial, viral, fungal and parasitic infections, replacing or remodeling injured tissue by stimulating fibroblast growth and, as the name suggests, killing certain tumors.

TNF-$\alpha$ has been implicated as a mediator in inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma. Much research has been conducted to study the effect of TNF-$\alpha$ and anti-TNF-$\alpha$ therapies. Studies in the area of cancer have shown that with TNF-$\alpha$ therapy it is important to balance the cytotoxicity and systemic toxicity of the potential drug candidates.

Inflammation is the response of a tissue to injury that may be caused by invading parasites, ischemia, antigen-antibody reactions or other forms of physical or chemical injury. It is characterized by increased blood flow to the tissue, causing pyrexia, redness, swelling, and pain. Each stimulus elicits a characteristic response that has a common theme. Inflammation occurs in three distinct phases:

1. an acute transient phase characterized by local vasodilation and increased capillary permeability;
2. a subacute phase characterized by infiltration of the site by leucocytes and phagocytic cells; and
3. a chronic proliferative phase characterized by tissue degeneration and fibrosis. The recruitment of inflammatory cells to sites of injury involves the concerted interactions of several types of mediators.

Several cytokines, especially IL-1 (interleukin-1) and TNF-$\alpha$ (tumor necrosis factor-$\alpha$), play an important role in the inflammatory process. Both IL-1 and TNF-$\alpha$ are derived from mononuclear cells and macrophages and in turn induce the expression of a variety of genes that contribute to the inflammatory process. An increase in TNF-$\alpha$ synthesis/release is a common phenomenon during the inflammatory process. Inflammation is an inherent part of various disease states like rheumatoid arthritis, Crohn's disease, septic shock syndrome, atherosclerosis, among other clinical conditions.

Rheumatoid arthritis (RA)—an autoimmune disorder, is a chronic, systemic, articular inflammatory disease of unknown etiology. In RA, the normally thin synovial lining of joints is replaced by an inflammatory, highly vascularized, invasive fibrocollagenase tissue (pannus), which is destructive to both cartilage and bone. Areas that may be affected include the joints of the hands, wrists, neck, jaw, elbows, feet and ankles. Cartilage destruction in RA is linked to aberrant cytokines and growth factor expression in the affected joints.

The most common rheumatoid arthritis therapy involves the use of nonsteroidal anti-inflammatory drugs (NSAIDs) to alleviate symptoms. However, despite the widespread use of NSAIDs, many individuals cannot tolerate the doses necessary to treat the disorder over a prolonged period of time. In addition, NSAIDs merely treat the symptoms of disorder and not the cause.

When patients fail to respond to NSAIDs, other drugs such as methotrexate, gold salts, D-penicillamine and prednisone are used. These drugs also have significant toxicities and their mechanism of action remains unknown.

TNF-$\alpha$ is considered to be at the apex of the proinflammatory cytokine cascade. Elevated circulating TNF-$\alpha$ levels and expression of other proinflammatory mediators are diminished by anti-TNF-$\alpha$ treatment, indicating possible beneficial effects this treatment can offer. Intervention of TNF-$\alpha$ activity can occur at the synthesis, release and receptor levels. Anti-TNF-$\alpha$ monoclonal antibodies, soluble receptors or receptor fusion proteins will target the TNF-$\alpha$ receptors/binding. Synthesis of TNF-$\alpha$ can also be suppressed by drugs/agents such as cyclosporine A, glucocorticoids or interleukin-10.

There are several small molecules, which inhibit the production of inflammatory cytokines and have demonstrated activity in animal rheumatoid arthritis models. Potential advantages of small molecules are that they are convenient to use for chronic problems, might facilitate tissue penetration, can be used in combination with other anti-inflammatory therapies. Such molecules are in various stages of preclinical and clinical development (Nature Reviews, 2003, 2, 736-746).

US 2003/0171585 describes tricyclic compounds (triphenylpropanamides) as anti-inflammatory agents.

JP 08-119920 describes tricyclic compounds (anilide derivatives) as steroid 5$\alpha$-reductase inhibitors useful in the treatment of prostate cancer, baldness and syphilis.

JP 11-130772 describes nitrogen-containing tricyclic compounds as leukocyte activation inhibitors that are useful for the treatment of inflammatory and allergic diseases.

JP 90-40662 describes tricyclic compounds that are substance P and bradykinin antagonists and are useful for the treatment of many diseases, including inflammation.

J. Med. Chem., 1970, Vol. 13, no. 4, 713-722, describes derivatives of 5,11-dihydrodibenz[b,e][1,4]oxazepine showing anti-anxiety and CNS depressant activities.

Monoclonal antibody drugs such as Infliximab, Etanercept and Adalimumab are useful as anti-inflammatory agents, but have drawbacks such as route of administration (only parenteral), high cost, allergy induction, activation of latent tuberculosis, increased risk of cancer and congestive heart disease.

There is a need for improved and alternative medicaments for the prevention and treatment of inflammatory disorders caused by increased TNF-α activity.

SUMMARY OF THE INVENTION

The present invention relates to novel condensed tricyclic compounds of general formula 1 or 1' (as provided herein below), as well as prodrugs, tautomeric forms, stereoisomers, pharmaceutically acceptable salts or solvates or polymorphs thereof, which inhibit TNF-α activity. The compounds of general formula 1 or 1' are useful for the treatment and prevention of diseases caused by increased TNF-α activity, such as rheumatoid arthritis, Crohn's disease, septic shock syndrome and atherosclerosis.

The present invention also relates to the subject condensed tricyclic compounds, which inhibit interleukin (IL-1, IL-6, IL-8) activity. The compounds are useful for the treatment and prevention of diseases caused by increased interleukin (IL-1, IL-6, IL-8) activity such as rheumatoid arthritis, osteoarthritis and other autoimmune conditions.

The invention further relates to pharmaceutical compositions comprising the subject condensed tricyclic compounds as active ingredient for the medical conditions caused by increased TNF-α activity indicated herein, especially inflammatory disorders.

The invention still further relates to processes for producing the subject condensed tricyclic compounds of general formula 1 or 1'.

DETAILED DESCRIPTION OF THE INVENTION

The present invention provides novel tricyclic compounds represented by the following general formula 1:

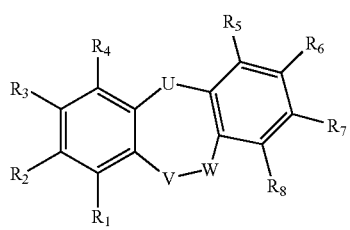

wherein $R_1$, $R_2$, $R_3$, $R_4$, $R_5$, $R_6$, $R_7$ and $R_8$ are each independently selected from: hydrogen, halogen, hydroxy, alkyl, cycloalkyl, alkenyl, alkoxy, cyano, nitro, trifluoromethyl, aryl, heterocyclyl, heteroaryl, alkyl sulfonyl, heterocyclylsulfonyl, heteroarylsulfonyl, sulfonamide, —S(O)$_2$—NH-alkyl, —S(O)$_2$—NH-cycloalkyl, —S(O)$_2$—NH-heterocyclyl, —S(O)$_2$—NH-heteroaryl, —S(O)$_2$—NH-aryl, —NH—S(O)$_2$-alkyl, —NH—S(O)$_2$-cycloalkyl, —NH—S(O)$_2$-aryl, —NH—S(O)$_2$-heterocyclyl, —NH—S(O)$_2$-heteroaryl, —(CH$_2$)$_n$C(O)R$_9$, —C(O)NR$_{11}$R$_{12}$, —NR$_{11}$R$_{12}$, hydrazine and N=R';

n is the integer 0, 1 or 2;

$R_9$ is hydrogen, halogen, alkyl, cycloalkyl, aralkyl, trifluoromethyl, OR$_{10}$, aryl or heterocyclyl;

$R_{10}$ is hydrogen, alkyl, cycloalkyl, trifluoromethyl, aryl or heterocyclyl;

$R_{11}$ and $R_{12}$ are each independently selected from: hydrogen, alkyl, cycloalkyl, alkoxyl, aryl, heterocyclyl, heteroaryl, —(CH$_2$)$_n$C(O)R$_9$, alkylamino and cycloalkylaminocarbonyl; or $R_{11}$ and $R_{12}$, together with the N atom to which they are bonded, form a 5-, 6-, 7- or 8-membered heterocyclyl, optionally having one or more additional heteroatoms selected from: O, N and S;

R' is heterocyclyl or cycloalkyl;

where alkyl or cycloalkyl is unsubstituted or substituted by one or two of the same or different groups selected from: halogen, hydroxy, carboxy, acetoxy, amino, cycloalkyl, alkoxy, aryloxy, alkoxy carbonyl, amino carbonyl, alkylamino, dialkylamino, cycloalkylamino, cycloalkylalkylamino, heterocyclylalkylamino, heteroarylamino, heteroarylalkylamino, dialkylaminoalkylamino, aminoaryl, aryl, heteroaryl and heterocyclyl;

heterocyclyl is unsubstituted or substituted by one or two of the same or different groups selected from: halogen, hydroxy, alkoxy, oxo, alkyl, cycloalkyl, cycloalkylalkyl, amino, aminoalkyl, hydroxyalkyl, heterocyclylalkyl, heteroarylalkyl, aralkyl, alkylaminoalkyl, formyl, alkylcarbonyl, alkoxycarbonyl, aralkoxycarbonyl, cycloalkylcarbonyl, arylcarbonyl, heteroarylcarbonyl, —SH, —S-alkyl, —S(O)$_2$-alkyl, —S(O)$_2$-aryl, aryl, alkylheteroaryl, cycloalkylheteroaryl, alkylamino and alkylheteroarylamino;

aryl is unsubstituted or substituted by one or two of the same or different groups selected from: halogen, nitro, alkyl, trifluoromethyl, alkoxy, amino, mono- or di-alkylamino, heteroarylalkyl and aralkyl;

heteroaryl is unsubstituted or substituted by one or two of the same or different groups selected from: halogen, alkyl, cycloalkyl, nitro and amino;

U is O;

V is CH$_2$, CHCH$_3$ or C(CH$_3$)$_2$ or NH;

W is S(O)$_m$; and m is the integer 0, 1 or 2;

in all its stereoisomeric and tautomeric forms and mixtures thereof in all ratios, and its pharmaceutically acceptable salts, pharmaceutically acceptable solvates, pharmaceutically acceptable polymorphs and prodrugs.

The present invention also provides novel tricyclic compounds represented by the following general formula 1':

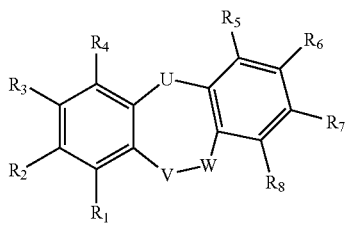

wherein $R_1$, $R_2$, $R_3$, $R_4$, $R_5$, $R_6$, $R_7$ and $R_8$ are each independently selected from: hydrogen, halogen, hydroxy, alkyl, cycloalkyl, alkenyl, alkoxy, cyano, nitro, trifluoromethyl, aryl, heterocyclyl, heteroaryl, alkyl sulfonyl, heterocyclylsulfonyl, heteroarylsulfonyl, sulfonamide, —S(O)$_2$—NH-alkyl, —S(O)$_2$—NH-cycloalkyl, —S(O)$_2$—NH-heterocyclyl, —S(O)$_2$—NH-heteroaryl, —S(O)$_2$—NH-aryl, —NH—S(O)$_2$-alkyl, —NH—S(O)$_2$-cycloalkyl, —NH—S(O)$_2$-aryl, —NH—S(O)$_2$-heterocyclyl, —NH—S(O)$_2$-heteroaryl, —(CH$_2$)$_n$C(O)R$_9$, —C(O)NR$_{11}$R$_{12}$, —NR$_{11}$R$_{12}$, hydrazine and N=R';

n is the integer 0, 1 or 2;

$R_9$ is hydrogen, halogen, alkyl, cycloalkyl, aralkyl, trifluoromethyl, aralkyl, OR$_{10}$, aryl or heterocyclyl;

$R_{10}$ is hydrogen, alkyl, cycloalkyl, trifluoromethyl, aralkyl, aryl or heterocyclyl;

$R_{11}$ and $R_{12}$ are each independently selected from: hydrogen, alkyl, cycloalkyl, alkoxy, aryl, heterocyclyl, heteroaryl, —(CH$_2$)$_n$C(O)R$_9$, alkylamino and cycloalkylaminocarbonyl; or $R_{11}$ and $R_{12}$, together with the N atom to which they are bonded, form a 5-, 6-, 7- or 8-membered heterocyclyl, optionally having one or more additional heteroatoms selected from: O, N and S;

R' is selected from: heterocyclyl and cycloalkyl;

U is C(O), CR$_{13}$R$_{14}$ or NR$_{15}$;

$R_{13}$ is H, alkyl, cycloalkyl or alkenyl;

$R_{14}$ is H, OH, OR$_{13}$ or OCOR$_{13}$;

$R_{15}$ is H, alkyl, cycloalkyl, alkenyl, C(O)R$_{13}$, C(O)OR$_{13}$ or alkylaminocarbonyl;

where alkyl or cycloalkyl is unsubstituted or substituted by one or two of the same or different groups selected from: halogen, hydroxy, carboxy, acetoxy, amino, cycloalkyl, alkoxy, aryloxy, alkoxy carbonyl, amino carbonyl, alkylamino, dialkylamino, cycloalkylamino, cycloalkylalkylamino, heterocyclylalkylamino, heteroarylamino, heteroarylalkylamino, dialkylaminoalkylamino, aminoaryl, aryl, heteroaryl and heterocyclyl;

heterocyclyl is unsubstituted or substituted by one or two of the same or different groups selected from: halogen, hydroxy, alkoxy, oxo, alkyl, cycloalkyl, cycloalkylalkyl, amino, aminoalkyl, hydroxyalkyl, heterocyclylalkyl, heteroarylalkyl, aralkyl, alkylaminoalkyl, formyl, alkylcarbonyl, alkoxycarbonyl, aralkoxycarbonyl, cycloalkylcarbonyl, arylcarbonyl, heteroarylcarbonyl, —SH, —S-alkyl, —S(O)$_2$-alkyl, —S(O)$_2$-aryl, aryl, alkylheteroaryl, cycloalkylheteroaryl, alkylamino and alkylheteroarylamino;

aryl is unsubstituted or substituted by one or two of the same or different groups selected from: halogen, nitro, alkyl, trifluoromethyl, alkoxy, amino, mono- or di-alkylamino, heteroarylalkyl and aralkyl;

heteroaryl is unsubstituted or substituted by one or two of the same or different groups selected from: halogen, alkyl, cycloalkyl, nitro and amino;

V is CH$_2$, CHCH$_3$ or C(CH$_3$)$_2$ or NH;

W is S(O)$_m$; and m is the integer 0, 1 or 2;

with the provisos that (i) when $R_1$, $R_2$, $R_3$, $R_4$, $R_5$, $R_6$, $R_7$ or $R_8$ is C(O)NR$_{11}$R$_{12}$, then $R_{11}$ or $R_{12}$ is other than alkyl substituted by heteroaryl; and (ii) when $R_1$, $R_2$, $R_3$, $R_4$, $R_5$, $R_6$, $R_7$ or $R_8$ is C(O)NR$_{11}$R$_{12}$, where one of $R_{11}$ and $R_{12}$ is H or alkyl and the other is substituted aryl, then W is S(O)$_m$ wherein m is the integer 1 or 2; and (iii) when U is NR$_{15}$, where $R_{15}$ is H or substituted alkyl, then at least one of $R_1$, $R_2$, $R_3$, $R_4$, $R_5$, $R_6$, $R_7$ or $R_8$ is C(O)R$_9$ or C(O)NR$_{11}$R$_{12}$, and (iv) when U is CR$_{13}$R$_{14}$, where $R_{13}$ is alkyl substituted by —NH-alkylaryl or by hydroxyl or is alkenyl and $R_{14}$ is hydrogen or alkoxy, then W is S(O)$_m$ wherein m is the integer 1 or 2;

(v) when U is C(O), then W is S(O)$_m$ wherein m is the integer 1 or 2;

in all its stereoisomeric and tautomeric forms and mixtures thereof in all ratios, and its pharmaceutically acceptable salts, pharmaceutically acceptable solvates, pharmaceutically acceptable polymorphs and prodrugs.

Listed below are definitions which apply to the terms as they are used throughout the specification and the appended claims (unless they are otherwise limited in specific instances), either individually or as part of a larger group. These broad or preferred definitions apply both to the end products of the formula (1a) or (1') (above) and formula (1a) or (1a') (as provided herein below) and, correspondingly, to the starting materials and intermediates required in each case for the preparation. These definitions should not be interpreted in the literal sense as they are not general definitions and are relevant only for this application.

As used herein, the term "alkyl" whether used alone or as part of a substituent group, refers to the radical of saturated aliphatic groups, including straight or branched-chain alkyl groups. Furthermore, unless stated otherwise, the term "alkyl" includes unsubstituted alkyl groups as well as alkyl groups, which are substituted by one or more different substituents. In preferred embodiments, a straight chain or branched chain alkyl has 20 or fewer carbon atoms in its backbone (e.g., C$_1$-C$_{20}$ for straight chain, C$_3$-C$_{20}$ for branched chain), and more preferably 15 or fewer carbon atoms. Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, or tert-butyl. Preferred examples of alkyl residue contain from 1 to 6 carbon atoms, more preferably from 1 to 4 carbon atoms such as methyl, ethyl, propyl, isopropyl, n-propyl, t-butyl, n-butyl, sec-butyl and iso-butyl.

The term "cycloalkyl" refers to a saturated mono-, bi- or poly-cyclic ring system containing a specified number of carbon atoms. Preferred cycloalkyls have from 3-10 carbon atoms in their ring structure, and more preferably have 3, 4, 5, 6 or 7 carbon atoms in the ring structure. Examples of cycloalkyl residues containing 3, 4, 5, 6 or 7 ring carbon atoms are cyclopropyl, cyclobutyl, cyclopentyl, cyclohexyl or cycloheptyl. Furthermore, unless stated otherwise, the term 'cycloalkyl' includes unsubstituted cycloalkyl and cycloalkyl which is substituted by one or more identical or different groups selected from any substitution mentioned below for alkyl, including alkyl, alkenyl, aminoalkyl, carbonyl-substituted alkyl, fluoroalkyls such as —$CF_3$ and the like. Cycloalkyl groups comprise saturated cycloalkyl ring systems which do not contain any double bonds within the rings as well as partially unsaturated cycloalkyl ring systems which contain one or more, preferably one, two or three, double bonds within the rings provided that the resulting system is stable and the double bonds are not located in such a manner that an aromatic system results.

Unless stated otherwise, and irrespective of any specific substituents bonded to alkyl groups that are indicated in the definition of the compounds of the formula (1) or (1') (above) and formula (1a) or (1a') (below), alkyl groups can in general be unsubstituted or substituted by one or more (for example 1, 2, 3, 4 or 5) identical or different substituents. Any kind of substituent present in substituted alkyl residues can be present in any desired position provided that the substitution does not lead to an unstable molecule. A substituted alkyl refers to, an alkyl residue in which one or more, for example, 1, 2, 3, 4 or 5 hydrogen atoms are replaced with substituents, for example, halogen, hydroxyl, carbonyl, alkoxyl, cycloalkyl, ester, ether, cyano, amino, amido, imino, sulfhydryl, alkylthio, thioester, sulfonyl, nitro, azido, acyloxy, heterocyclo, aralkyl, or an aryl or heteroaryl group. The carbon backbone of the alkyl group may contain heteroatoms such as oxygen, sulfur or nitrogen. Examples of substituted acyclic alkyls are hydroxymethyl, hydroxyethyl, 2-hydroxyethyl, aminoethyl or morpholinoethyl.

It will be understood by those skilled in the art that the moieties substituted on the hydrocarbon chain can themselves be substituted, if appropriate. For example, the substituents of a substituted alkyl may include substituted and unsubstituted forms of amino, imino, amido, sulfonyl (including sulfonate and sulfonamide), as well as ether, alkylthio, carbonyl (including ketones, aldehydes, carboxylates, and esters), fluoroalkyls such as —$CF_3$, cyano and the like.

The terms "alkenyl" and "alkynyl" refer to unsaturated aliphatic groups analogous in length and possible substitution to the alkyls described above, but that contain at least one double or triple bond, respectively, for example 1, 2 or 3 double bonds and/or triple bonds, provided that the double bonds are not located within a cyclic alkyl group in such a manner that an aromatic system results. Examples of alkenyl groups include vinyl, 1-propenyl, 2-propenyl, 2-butenyl, 2-methyl-1-propenyl, 3-methyl-2-butenyl etc. Examples of alkynyl groups include ethynyl, 2-propynyl, 2-butynyl and 3-butynyl.

Furthermore, unless otherwise stated, the terms "alkenyl" and "alkynyl" include unsubstituted alkenyl and alkynyl groups as well as alkenyl and alkynyl groups which are substituted by one or more (for example 1, 2, 3, 4 or 5), identical or different groups mentioned above for alkyl, for example, aminoalkenyl, aminoalkynyl, amidoalkenyl, amidoalkynyl, iminoalkenyl, iminoalkynyl, thioalkenyl, thioalkynyl, carbonyl-substituted alkenyl or alkynyl, alkenoxyl or alkynoxyl.

As used herein the term "alkoxyl" or "alkoxy" refers to an alkyl group having an oxygen radical attached thereto, wherein alkyl is as defined above. The terms include, therefore, alkoxyl or alkoxy groups which are substituted by one or more identical or different groups mentioned above for alkyl. Representative alkoxyl groups include methoxy, ethoxy, propoxy, tert-butoxy and the like.

As used herein the term "acyl" refers to any group or organic radical such as alkyl (which can be further substituted with an alkyl, alkoxy, cycloalkylamino, hydroxy or halo) or cycloalkyl attached to a carbonyl group, wherein alkyl and cycloalkyl are as defined above.

As used herein the term "aryl" refers to a monocyclic or polycyclic hydrocarbon group having up to 14 ring carbon atoms, preferably up to 10 ring carbon atoms, in which at least one carbocyclic ring is present that has a conjugated π electron system. Suitable examples of ($C_6$-$C_{14}$)-aryl residues include phenyl, naphthyl, biphenyl, fluorenyl or anthracenyl, especially phenyl and naphthyl. Unless stated otherwise, and irrespective of any specific substituents bonded to aryl groups which are indicated in the definition of the compounds of formula (1a) or (1') (above) and formula (1a) or (1a') (below), aryl residues, for example phenyl, naphthyl or fluorenyl, can in general be optionally substituted by one or more substituents, preferably by up to five identical or different substituents selected from the groups consisting of halogen, alkyl, alkenyl, alkynyl, fluoroalkyl such as $CF_3$, hydroxyl, aryloxy, amino, substituted amino, cyano, nitro, thiol, imine, amide, carbonyl (such as carboxyl, formate, carbamide, ester, ketone or aldehyde), sulfhydryl, alkylthio, silyl ether, thiocarbonyl (such as thioester, thioacetate or thioformate), sulfonyl, aminoacid ester and a heterocyclo group, which is saturated, partially unsaturated or aromatic. Aryl residues can be bonded via any desired position, and in substituted aryl residues the substituents can be located in any desired position. For example, in monosubstituted phenyl residues the substituent can be located in the 2-position, the 3-position, the 4-position or the 5-position. If the phenyl group carries two substituents, they can be located in 2,3-position, 2,4-position, 2,5-position, 2,6-position, 3,4-position or 3,5-position.

The term "heteroatom" as used herein means an atom of any element other than carbon or hydrogen. Preferred heteroatoms are nitrogen, oxygen and sulfur. It should be noted that any heteroatom with unsatisfied valences is assumed to have a hydrogen atom to satisfy the valences.

The terms "heterocyclyl", "heterocycle" and "heterocyclo" refer to a saturated, partially unsaturated or aromatic monocyclic or polycyclic heterocyclic, ring system containing 3, 4, 5, 6, 7, 8, 9, 10, 11, 12, 13 or 14 ring atoms of which 1, 2, 3 or 4 are identical or different heteroatoms selected from: nitrogen, oxygen and sulfur. The heterocyclyl group may, for example, have 1 or 2 oxygen atoms and/or 1 or 2 sulfur atoms and/or 1 to 4 nitrogen atoms in the ring. In monocyclic groups, heterocyclyl preferably is a 3-membered, 4-membered, 5-membered, 6-membered or 7-membered ring, more preferably a 5- or 6-membered ring. Suitable examples of such heterocyclyl groups are piperazinyl, piperidinyl imidazolyl, pyrrolidinyl and morpholinyl. In polycyclic groups, heterocyclyl may comprise either fused rings in which two or more carbons are common to two adjoining rings, or bridged rings in which rings are joined through non-adjacent atoms. In polycyclic groups, heterocyclyl preferably comprises two fused rings (bicyclic), one of which is a 5- or 6-membered heterocyclic ring and the other of which is a 5- or 6-membered heterocyclic ring. Exemplary bicyclic and tricyclic heterocyclic groups include benzoxazolyl, quinolyl, isoquinolyl, carbazolyl, indolyl, isoindolyl, phenoxazinyl, benzothiazolyl, benzimidazolyl, benzoxadiazolyl and benzofurazanyl.

The ring heteroatoms can be present in any desired number and in any position with respect to each other provided that the resulting heterocyclic system is known in the art and is stable and suitable as a subgroup in a drug substance. Preferred are heterocyclyl groups having 1 or 2 identical or different heteroatoms selected from: nitrogen, oxygen and sulfur. Examples of such heterocyclyl groups are: pyrrolyl, furyl, thiophenyl, imidazolyl, oxazolyl, isoxazolyl, thiazolyl, isothiazolyl, triazolyl, pyrazolyl, pyridinyl, pyrazinyl, pyridazinyl, pyrimidinyl, azepinyl, tetrahydrothiophenyl, tetrahydrofuranyl, morpholinyl, thiomorpholinyl, tetrahydropyranyl, lactams, pyrrolidinyl, azetidinyl, piperidinyl, piperazinyl and the like.

The heterocyclyl group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be 1-pyrrolidinyl (=pyrrolidino), 2-pyrrolidinyl or 3-pyrrolidinyl, and imidazolyl can be 1-imidazolyl, 2-imidazolyl, 4-imidazolyl or 5-imidazolyl.

Heterocyclyl comprises saturated heterocyclic ring systems which do not contain any double bonds within the rings, as well as unsaturated heterocyclic ring systems which contain one or more, preferably up to 5 double bonds within the rings provided that the resulting system is stable. Unsaturated rings may be non-aromatic or aromatic. Aromatic heterocyclyl groups may also be referred to by the customary term "heteroaryl" for which all the definitions and explanations above and below relating to heterocyclyl apply.

Unless stated otherwise, and irrespective of any substituents bonded to heterocyclyl groups which are indicated in the definition of the compounds of formula (1a) or (1') (above) and formula (1a) or (1a') (below), the heterocyclyl group can be unsubstituted or substituted on ring carbon atoms with one or more substituents, preferably up to five identical or different substituents. Each suitable ring nitrogen atom in a heterocyclyl group can independently of the other be unsubstituted, i.e. carry a hydrogen atom, or can be substituted. Suitable examples of substituents for the ring carbon and ring nitrogen atoms are: ($C_1$-$C_8$)-alkyl, in particular ($C_1$-$C_4$)-alkyl, alkoxy, halogen, hydroxyl, hydroxy-($C_1$-$C_4$)-alkyl such as, for example, hydroxymethyl or 1-hydroxyethyl or 2-hydroxyethyl, alkenyl, alkynyl, fluoroalkyl such as $CF_3$, aryloxy, amino, cyano, nitro, thiol, imine, amide or carbonyl (such as carboxyl, formate, carbamide, an ester, ketone or aldehyde), silyl ether, thiocarbonyl (such as thioesters, a thioacetate or a thioformate), sulfonyl, aminoacid ester, heterocyclyl, aryl or the like. The substituents can be present at one or more positions provided that a stable molecule results.

As used herein the term "aralkyl" refers to an alkyl group substituted with an aryl or heteroaryl group, wherein the terms alkyl, aryl and heteroaryl are as defined above. Exemplary aralkyl groups include —$(CH_2)_p$-phenyl, —$(CH_2)_p$-pyridyl, —$(CH_2)_p$-imidazolyl, —$(CH_2)_p$-thiophenyl and —$(CH_2)_p$-furyl, wherein p is an integer from 1 to 3.

The term "halogen" refers to fluorine, chlorine, bromine or iodine, preferably fluorine, chlorine or bromine.

As used herein the terms, mono- or di-substituted amino refers to an amino group substituted by one or two groups which may be the same or different. For instance, mono-substituted amino means an amino group in which only one hydrogen atom is replaced with a substituent. Disubstituted amino means an amino group in which both the hydrogen atoms are replaced with the same or different substituents.

The substituents on the amino group are independently selected from: alkyl, haloalkyl, hydroxyalkyl, alkoxyalkyl, acyl, haloacyl, heterocyclylalkyl, heteroaryalkyl, aminoalkyl, alkoxyaralkyl and the like. It will be understood by those skilled in the art that the moieties on the amino group can themselves be substituted, if appropriate.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

In one embodiment, the present invention provides novel tricyclic compounds represented by the formula 1 above, wherein $R_7$ is alkyl, —$(CH_2)_nC(O)R_9$ or —$C(O)NR_{11}R_{12}$; where n, $R_9$, $R_{10}$, $R_{11}$ and $R_{12}$ are as defined above.

In another embodiment, the present invention provides novel tricyclic compounds represented by the formula 1' above, wherein $R_7$ is alkyl, —$(CH_2)_nC(O)R_9$ or —$C(O)NR_{11}R_{12}$; where n, $R_9$, $R_{10}$, $R_{11}$ and $R_{12}$ are as defined above; and with the provisos that (i) when $R_7$ is $C(O)NR_{11}R_{12}$, then $R_{11}$ or $R_{12}$ is other than alkyl substituted by heteroaryl; and (ii) when $R_7$ is $C(O)NR_{11}R_{12}$, where one of $R_{11}$ and $R_{12}$ is H or alkyl and the other is substituted aryl, then W is $S(O)_m$, wherein m is the integer 1 or 2, and (iii) when U is $CR_{13}R_{14}$, where $R_{13}$ or $R_{14}$ is alkyl substituted by —NH-alkylaryl, or by hydroxyl or is alkenyl and $R_{14}$ is hydrogen or alkoxy, then W is $S(O)_m$, wherein m is the integer 1 or 2;

(iv) when U is $C(O)$, then W is $S(O)_m$ wherein m is the integer 1 or 2;

in all its stereoisomeric and tautomeric forms and mixtures thereof in all ratios, and its pharmaceutically acceptable salts, pharmaceutically acceptable solvates, pharmaceutically acceptable polymorphs and prodrugs.

In another embodiment, the present invention provides novel tricyclic compounds represented by the following formula 1a:

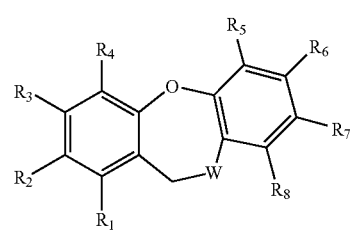

1a wherein $R_1$, $R_2$, $R_3$, $R_4$, $R_5$, $R_6$ and $R_8$ are each independently selected from: hydrogen, halogen, hydroxy, alkyl, alkenyl, cycloalkyl, alkoxy, cyano, nitro, trifluoromethyl, aryl, heterocyclyl, heteroaryl, alkylsulfonyl, heterocyclylsulfonyl, heteroarylsulfonyl, —$S(O)_2$—NH-heterocyclyl, —$S(O)_2$—NH-heteroaryl, sulfonamide, —$S(O)_2$—NH-alkyl, —$S(O)_2$—NH-cycloalkyl, —$S(O)_2$—NH-aryl, —NH—$S(O)_2$-alkyl, —NH—$S(O)_2$-cycloalkyl, —NH—$S(O)_2$-aryl, —NH—$S(O)_2$-heterocyclyl, —NH—$S(O)_2$-heteroaryl, —$(CH_2)_nC(O)R_9$, $NR_{11}R_{12}$, hydrazine and N=R';

$R_7$ is alkyl, —$(CH_2)_nC(O)R_9$ or —$C(O)NR_{11}R_{12}$;

$R_9$ is hydrogen, halogen, alkyl, cycloalkyl, trifluoromethyl, $OR_{10}$, aryl or heterocyclyl;

$R_{10}$ is hydrogen, alkyl, cycloalkyl, trifluoromethyl, aryl or heterocyclyl;

$R_{11}$ and $R_{12}$ are each independently selected from: hydrogen, alkyl, cycloalkyl, alkylamino, aryl, heteroaryl, heterocyclyl, —$(CH_2)_nC(O)R_9$ and cycloalkylaminoalkylcarbonyl; or $R_{11}$ and $R_{12}$, together with the N atom to which they are bonded, form a 5-, 6-, 7- or 8-membered heterocyclyl, optionally having one or more additional heteroatoms selected from: O, N and S;

R' is heterocyclyl or cycloalkyl;

n is the integer 0, 1 or 2;

where alkyl or cycloalkyl is unsubstituted or substituted by one or two of the same or different groups selected from: halogen, hydroxy, alkylcarboxy, amino, cycloalkyl, alkoxy, aryloxy, alkoxylcarbonyl, arylalkoxycarbonyl, aminocarbonyl, alkylamino, dialkylamino, cycloalkylamino, cycloalkyl alkylamino, heterocyclyl alkylamino, heteroaryl, heteroarylamino, heteroarylalkylamino, dialkylamino alkylamino, aryl, amino aryl, heteroaryl and heterocyclyl;

heterocyclyl is unsubstituted or substituted by one or two of the same or different groups selected from: halogen, hydroxy, alkoxy, oxo, alkyl, cycloalkyl, cycloalkyl alkyl, aryl, hydroxyalkyl, amino, aminoalkyl, alkylaminoalkyl, heterocyclyl alkyl, heteroaryl alkyl, aralkyl, alkylheteroaryl, cycloalkylheteroaryl, formyl, alkylcarbonyl, alkoxycarbonyl, aryl alkoxycarbonyl, cycloalkylcarbonyl, arylcarbonyl, heteroarylcarbonyl, —SH, —S-alkyl, —$S(O)_2$-alkyl, —$S(O)_2$-aryl, alkylheteroaryl, cycloalkylheteroaryl, alkylamino and alkylheteroarylamino;

aryl is unsubstituted or substituted by one or two of the same or different groups selected from: halogen, nitro, alkyl, trifluoromethyl, alkoxy, amino, mono- or di-alkylamino, heteroaryl alkyl and aralkyl;

heteroaryl is unsubstituted or substituted by one or two of the same or different groups selected from: halogen, alkyl, cycloalkyl, nitro and amino;

W is $S(O)_m$; and m is the integer 0, 1 or 2;

in all its stereoisomeric and tautomeric forms and mixtures thereof in all ratios, and its pharmaceutically acceptable salts, pharmaceutically acceptable solvates, pharmaceutically acceptable polymorphs and prodrugs.

In one embodiment of a compound of formula 1 or 1a, the terms 'alkyl', 'cycloalkyl', 'alkoxy', 'alkenyl', and 'aryl' are limited by their respective carbon content as follows: 'Alkyl' when used alone is '$C_1$-$C_{12}$ alkyl' and when used as part of a substituent group is '$C_1$-$C_4$ alkyl', 'cycloalkyl' is '$C_3$-$C_6$ cycloalkyl', 'alkoxy' is '$C_1$-$C_4$ alkoxy', 'alkenyl' is '$C_2$-$C_6$ alkenyl', and 'aryl' is '$C_6$-$C_{10}$ aryl'.

In further embodiments of any of the compounds of formula (1a) or (1a), the groups $R_1$, $R_2$, $R_3$, $R_4$, $R_5$, $R_6$, $R_7$ and $R_8$ may, independently of each other, have the following definitions. Hence, one or more of the groups $R_1$, $R_2$, $R_3$, $R_4$, $R_5$, $R_6$, $R_7$ and $R_8$ may have the preferred definitions given below:

$R_1$ is hydrogen, $C_1$-$C_4$ alkyl or halogen;

$R_2$ is hydrogen, halogen, amino, nitro, cyano, heterocyclyl, heterocyclyl $C_1$-$C_4$alkylheterocyclyl, amino $C_1$-$C_4$ alkylheterocyclyl, aryl $C_1$-$C_4$ alkylheterocyclyl, heteroarylbenzyl $C_1$-$C_4$ alkylheterocyclyl, heteroaryl $C_1$-$C_4$ alkylheterocyclyl, di($C_1$-$C_4$ alkyl)benzylheterocyclyl, $C_3$-$C_6$ cycloalkylheterocyclyl, $C_3$-$C_6$ cycloalkylheteroaryl, heteroarylcarbonylheterocyclyl, heterocyclylsulfonyl, —$S(O)_2$—NH-heterocyclyl, $C_1$-$C_4$ alkylsulfonyl, $C_1$-$C_4$ alkoxy, $C_3$-$C_6$ cycloalkyl$C_1$-$C_4$alkyl, —$NR_{11}R_{12}$, $NHR_{16}$ or N=heterocyclyl;

$R_3$ is hydrogen, $NR_{11}R_{12}$ or $NHR_{16}$;

$R_4$ and $R_5$ are each independently selected from: hydrogen, halogen, $C_1$-$C_4$ alkyl, nitro, amino, halo$C_1$-$C_4$alkylamino and heterocyclyl $C_1$-$C_4$ alkylamino;

$R_6$ and $R_8$ are each independently selected from: hydrogen, $C_1$-$C_4$ alkyl and halogen;

$R_7$ is hydroxy $C_1$-$C_4$ alkyl, chloro $C_1$-$C_4$ alkyl, cyano $C_1$-$C_4$ alkyl, formyl, —$(CH_2)_nC(O)OR_{10}$ or $CONHR_{16}$;

$R_{10}$ is hydrogen, $C_1$-$C_4$ alkyl, amino $C_1$-$C_4$ alkyl, heterocyclyl $C_1$-$C_4$ alkyl, aryl, heteroaryl or heterocyclyl;

$R_{11}$ and $R_{12}$ are each independently selected from: hydrogen, $C_1$-$C_4$ alkyl, hydroxy $C_1$-$C_4$ alkyl, halo$C_1$-$C_4$ alkyl, amino$C_1$-$C_4$ alkyl, aryl$C_1$-$C_4$ alkyl, $C_3$-$C_6$cycloalkyl$C_1$-$C_4$alkyl, $C_6$-$C_{10}$ aryl, heterocyclyl or heteroaryl; or $R_{11}$ and $R_{12}$, together with the N atom to which they are bonded, form a 6- or 7-membered, heterocyclyl, optionally having one or more additional N or O heteroatoms;

$R_{16}$ is formyl, $C_1$-$C_4$ alkyl, $C_3$-$C_6$cycloalkyl, heterocyclyl$C_1$-$C_4$alkyl, heteroaryl$C_1$-$C_4$alkyl, heteroarylamino $C_1$-$C_4$ alkyl, di($C_1$-$C_4$)alkylamino$C_1$-$C_4$ alkyl, amino$C_1$-$C_4$ alkyl, heterocyclyl $C_1$-$C_4$alkylamino$C_1$-$C_4$ alkyl, halo$C_1$-$C_4$ alkyl, di($C_1$-$C_4$)alkyl amino $C_1$-$C_4$ alkyl amino $C_1$-$C_4$alkyl, carboxy ($C_1$-$C_4$)alkyl, hydroxy $C_1$-$C_4$ alkyl, $C_1$-$C_4$ alkylcarbonyl, trifluoromethylcarbonyl, di($C_1$-$C_4$alkyl)amino $C_1$-$C_4$alkylcarbonyl, $C_3$-$C_6$ cycloalkylamino$C_1$-$C_4$alkylcarbonyl, halo $C_1$-$C_4$alkylcarbonyl, hydroxy $C_1$-$C_4$ alkylcarbonyl, $C_1$-$C_4$ alkylcarbonyl, $C_1$-$C_4$ alkyl amino$C_1$-$C_4$alkylcarbonyl, $C_6$-$C_{10}$ aryl carbonyl, benzyloxycarbonyl, halo carbonyl $C_1$-$C_4$alkylcarbonyl, amino carbonyl $C_1$-$C_4$alkylcarbonyl, $C_1$-$C_4$alkoxycarbonyl $C_1$-$C_4$alkylcarbonyl, $C_1$-$C_4$alkylcarbonyloxy $C_1$-$C_4$alkylcarbonyl or heterocyclyl $C_1$-$C_4$ alkylcarbonyl;

n is the integer 0, 1 or 2;

where heterocyclyl is unsubstituted or substituted by one or two of the same or different groups selected from: halogen, hydroxy, $C_1$-$C_4$ alkoxy, oxo, $C_1$-$C_4$ alkyl, $C_3$-$C_6$ cycloalkyl, $C_3$-$C_6$ cycloalkyl $C_1$-$C_4$ alkyl, $C_6$-$C_{10}$ aryl, hydroxy $C_1$-$C_4$ alkyl, amino, amino $C_1$-$C_4$ alkyl, $C_1$-$C_4$ alkylamino $C_1$-$C_4$ alkyl, heterocyclyl $C_1$-$C_4$ alkyl, heteroaryl $C_1$-$C_4$alkyl, $C_6$-$C_{10}$ aryl $C_1$-$C_4$ alkyl, $C_1$-$C_4$ alkylheteroaryl, $C_3$-$C_{10}$ cycloalkylheteroaryl, formyl, $C_1$-$C_4$alkylcarbonyl, $C_1$-$C_4$ alkoxycarbonyl, $C_6$-$C_{10}$ aryl $C_1$-$C_4$ alkoxycarbonyl, $C_6$-$C_{10}$ arylcarbonyl, $C_3$-$C_{10}$ cycloalkylcarbonyl, heteroarylcarbonyl, —SH, —S—$C_1$-$C_4$ alkyl, —$S(O)_2$—$C_1$-$C_4$ alkyl, —$S(O)_2$—$C_6$-$C_{10}$ aryl, $C_1$-$C_4$ alkylheteroaryl, $C_3$-$C_{10}$ cycloalkylheteroaryl, $C_1$-$C_4$ alkylamino and $C_1$-$C_4$ alkylheteroarylamino;

aryl is unsubstituted or substituted by one or two of the same or different groups selected from: halogen, nitro, $C_1$-$C_4$alkyl, trifluoromethyl, $C_1$-$C_4$ alkoxy, amino, mono- or di-$C_1$-$C_4$ alkylamino, heteroaryl $C_1$-$C_4$ alkyl and $C_6$-$C_{10}$ar$C_1$-$C_4$ alkyl; and heteroaryl is unsubstituted or substituted by one or two of the same or different groups selected from: halogen, $C_1$-$C_4$ alkyl, $C_3$-$C_4$ cycloalkyl, nitro and amino.

In a further embodiment, a compound of formula (1a) or (1a) is a compound in which $R_2$ is hydrogen, halogen, nitro, amino, cyano, $C_1$-$C_4$alkyl, $C_1$-$C_4$alkoxy, morpholinyl, [1,4]diazepanyl, 4-cyclopropyl-2-oxo-piperazinyl, piperazinyl, N-formyl piperazinyl, $C_1$-$C_4$ alkylcarbonyl piperazinyl, $C_1$-$C_4$alkyl piperazinyl, hydroxy $C_1$-$C_4$alkyl piperazinyl, $C_1$-$C_4$alkyl sulfonyl piperazinyl, $C_3$-$C_6$ cycloalkyl piperazinyl, benzyl piperazinyl, $C_1$-$C_4$ alkoxycarbonyl piperazinyl, $C_6$-$C_{10}$ aryl $C_1$-$C_4$ alkoxycarbonyl piperazinyl, $C_6$-$C_{10}$ arylcarbonyl piperazinyl, amino$C_1$-$C_4$alkyl piperazinyl, substituted phenyl $C_1$-$C_4$alkyl piperazinyl, imidazolylbenzyl $C_1$-$C_4$alkyl piperazinyl, $C_3$-$C_6$cycloalkyl thiadiazolylpiperazinyl, pyrrolyl carbonylpiperazinyl, furanyl$C_1$-$C_4$ alkylpiperazinyl, dimethylaminobenzyl piperazinyl, thiophenyl$C_1$-$C_4$ alkylpiperazinyl, morpholinyl$C_1$-$C_4$alkyl piperazinyl, $C_1$-$C_4$alkyl sulfonyl, piperazinylsulfonyl, isooxazolylaminosulfonyl, formyl amino, $C_1$-$C_4$ alkylamino, dimethyl amino, $C_1$-$C_4$ alkylcarbonylamino, dimethylamino $C_1$-$C_4$alkylcarbonylamino, $C_3$-$C_6$ cycloalkylamino$C_1$-$C_4$alkylcarbonyl amino, hydroxy $C_1$-$C_4$alkylcarbonylamino, $C_1$-$C_4$alkylcarbonyloxy $C_1$-$C_4$alkylcarbonylamino, chloro $C_1$-$C_4$alkylcarbonylamino, morpholinyl $C_1$-$C_4$alkylcarbonylamino, trifluoromethylcarbonylamino, benzyloxycarbonylamino, piperazinyl$C_1$-$C_4$alkylamino, morpholinyl$C_1$-$C_4$alkylamino, phenylalkylamino, imidazolylamino $C_1$-$C_4$ alkyl amino, imidazolyl $C_1$-$C_4$ alkyl amino, dimethylamino $C_1$-$C_4$ alkylamino, isobutylamino, amino $C_1$-$C_4$ alkylamino, morpholinyl $C_1$-$C_4$alkylamino $C_1$-$C_4$ alkylamino, morpholinyl $C_1$-$C_4$ alkylamino, $C_3$-$C_6$ cycloalkyl$C_1$-$C_4$alkylamino, chloro $C_1$-$C_4$alkylamino, dimethylamino$C_1$-$C_4$ alkylamino $C_1$-$C_4$ alkylamino, carboxy $C_1$-$C_4$ alkylamino, hydroxy $C_1$-$C_4$ alkylamino, di(hydroxy $C_1$-$C_4$ alkyl)amino, chloro $C_1$-$C_4$alkylamino, di(chloro$C_1$-$C_4$alkyl)amino, benzyloxycarbonyl$C_1$-$C_4$alkylamino, $NR_{11}R_{12}$ or pyrrolidin-2ylidene;

$R_{11}$ and $R_{12}$ are each independently selected from: hydrogen, $C_1$-$C_4$ alkyl, morpholinyl$C_1$-$C_4$alkyl, $C_6$-$C_{10}$ aryl $C_1$-$C_4$ alkyl, $C_3$-$C_6$cycloalkyl$C_1$-$C_4$alkyl, hydroxy $C_1$-$C_4$ alkyl, chloro $C_1$-$C_4$alkyl, $C_6$-$C_{10}$ aryl, heterocyclyl and heteroaryl; where heterocyclyl is substituted with $C_1$-$C_4$ alkyl; and aryl is substituted with one or two of the same or different groups selected from: halogen, trifluoromethyl, $C_1$-$C_4$ alkyl, $C_1$-$C_4$ alkoxy and mono- or di-substituted amino;

$R_3$ is hydrogen, amino, $C_1$-$C_4$alkylamino, amino $C_1$-$C_4$alkylamino, unsubstituted piperazinyl or piperazinyl substituted by $C_1$-$C_4$alkyl;

$R_4$ is hydrogen or halogen; $R_5$ is hydrogen or $C_1$-$C_4$ alkyl; and $R_7$ is C(O)O$C_1$-$C_4$ alkyl, C(O)OH, $CH_2$C(O)O$C_1$-$C_4$ alkyl, $CH_2$C(O)OH, formyl, hydroxy $C_1$-$C_4$ alkyl, chloro $C_1$-$C_4$ alkyl, cyano $C_1$-$C_4$ alkyl or —C(O)NH $C_3$-$C_6$ cycloalkyl.

In a further embodiment, a compound of formula (1) or (1a) is a compound in which $R_2$ is amino, formylamino, $C_1$-$C_4$alkylamino, $C_1$-$C_4$alkylcarbonylamino, chloro $C_1$-$C_4$alkylcarbonylamino, hydroxy $C_1$-$C_4$alkylcarbonylamino, $C_1$-$C_4$alkyl carbonyloxy $C_1$-$C_4$alkylcarbonylamino, carboxy$C_1$-$C_4$alkylamino, di(chloro$C_1$-$C_4$alkyl)amino, di(hydroxy$C_1$-$C_4$alkyl)amino, acetamide, propionamide, morpholinyl, [1,4]diazepanyl, unsubstituted piperazinyl or piperazinyl substituted by at least one group selected from: $C_1$-$C_4$alkyl, $C_3$-$C_6$cycloalkyl, formyl, $C_1$-$C_4$alkylcarbonyl, hydroxy $C_1$-$C_4$alkyl, $C_1$-$C_4$alkylsulfonyl, benzyl, oxo, $C_1$-$C_4$ alkoxycarbonyl, benzyloxycarbonyl, unsubstituted $C_6$-$C_{10}$ arylcarbonyl or $C_6$-$C_{10}$ arylcarbonyl substituted by at least one group selected from: $C_1$-$C_4$alkyl, $C_1$-$C_4$alkoxy, halogen and trifluoromethyl;

$R_3$ is hydrogen;

$R_4$ is halogen; $R_5$ is $C_1$-$C_4$ alkyl; and $R_7$ is C(O)O$C_1$-$C_4$ alkyl, C(O)OH, $CH_2$C(O)O$C_1$-$C_4$ alkyl or $CH_2$C(O)OH.

In yet another embodiment, a compound of formula (1a) or (1a) is a compound in which $R_1$ and $R_2$ are hydrogen;

$R_3$ is amino, amino $C_1$-$C_4$alkylamino, unsubstituted piperazinyl or piperazinyl substituted by $C_1$-$C_4$alkyl;

$R_4$ is chloro, bromo or fluoro;

$R_5$ is methyl or ethyl;

$R_6$ and $R_8$ are hydrogen; and $R_7$ is C(O)O$C_1$-$C_4$ alkyl, C(O)OH.

In yet another embodiment, a compound of formula (1a) or (1a) is a compound in which $R_1$ is hydrogen;

$R_2$ is unsubstituted piperazinyl or piperazinyl substituted by $C_1$-$C_4$alkyl, $C_3$-$C_6$cycloalkyl, formyl, $C_1$-$C_4$ alkylcarbonyl, hydroxy $C_1$-$C_4$alkyl, $C_1$-$C_4$alkylsulfonyl, benzyl, oxo, $C_1$-$C_4$ alkoxycarbonyl, benzyloxycarbonyl, unsubstituted $C_6$-$C_{10}$ arylcarbonyl or $C_6$-$C_{10}$ arylcarbonyl substituted by $C_1$-$C_4$alkyl;

$R_3$ is hydrogen;

$R_4$ is chloro, bromo or fluoro;

$R_5$ is methyl or ethyl; and $R_6$ and $R_8$ are hydrogen.

In yet another embodiment, a compound of formula (1a) or (1a) is a compound in which W is $SO_2$.

In another embodiment, the present invention provides novel tricyclic compounds represented by the following formula 1a':

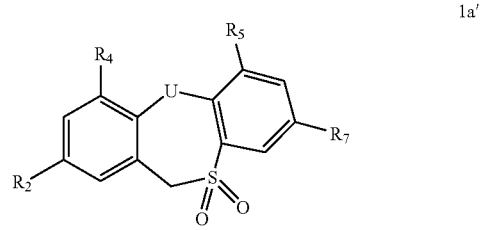

wherein $R_2$ is hydrogen, halogen, hydroxy, alkyl, cycloalkyl, alkoxy, cyano, nitro, trifluoromethyl, aryl, heterocyclyl, heteroaryl, —$(CH_2)_n$C(O)$R_9$ or $NR_{11}R_{12}$;

$R_4$ and $R_5$ are each independently selected from: hydrogen, halogen, hydroxy, trifluoromethyl, alkyl, cycloalkyl, alkenyl, alkoxy, aryl, heteroaryl and heterocyclyl;

$R_7$ is —$(CH_2)_nC(O)R_9$;

$R_9$ is hydrogen, halogen, alkyl, cycloalkyl, aralkyl, trifluoromethyl, $OR_{10}$, aryl or heterocyclyl;

$R_{10}$ is hydrogen, alkyl, cycloalkyl, trifluoromethyl, aryl or heterocyclyl;

$R_{11}$ and $R_{12}$ are each independently selected from: hydrogen, alkyl, cycloalkyl, alkylamino, aryl, heteroaryl, heterocyclyl, —$(CH_2)_nC(O)R_9$ and cycloalkylaminoalkylcarbonyl; or $R_{11}$ and $R_{12}$, together with the N atom to which they are bonded, form a 5-, 6-, 7- or 8-membered heterocyclyl, optionally having one or more additional heteroatoms selected from: O, N and S;

U is C(O), $CR_{13}R_{14}$ or $NR_{15}$;

$R_{13}$ is H, alkyl, cycloalkyl or alkenyl;

$R_{14}$ is H, OH, $OR_{13}$ or $OCOR_{13}$;

$R_{15}$ is H or alkyl; and n is the integer 0, 1 or 2;

where alkyl or cycloalkyl is unsubstituted or substituted by one or two of the same or different groups selected from: halogen, hydroxy, alkylcarboxy, amino, cycloalkyl, alkoxy, aryloxy, alkoxylcarbonyl, arylalkoxycarbonyl, aminocarbonyl, alkylamino, dialkylamino, cycloalkylamino, cycloalkylalkylamino, heterocyclylalkylamino, heteroaryl, heteroarylamino, heteroarylalkylamino, dialkylaminoalkylamino, aryl, aminoaryl, heteroaryl and heterocyclyl;

heterocyclyl is unsubstituted or substituted by one or two of the same or different groups selected from: halogen, hydroxy, alkoxy, oxo, alkyl, cycloalkyl, cycloalkyl alkyl, aryl, hydroxyalkyl, amino, aminoalkyl, alkylaminoalkyl, heterocyclylalkyl, heteroarylalkyl, aralkyl, alkylheteroaryl, cycloalkylheteroaryl, formyl, alkylcarbonyl, alkoxycarbonyl, cycloalkylcarbonyl, arylcarbonyl, heteroarylcarbonyl, —SH, —S-alkyl, —$S(O)_2$-alkyl, —$S(O)_2$-aryl, alkylheteroaryl, cycloalkylheteroaryl, alkylamino and alkylheteroarylamino;

aryl is unsubstituted or substituted by one or two of the same or different groups selected from: halogen, nitro, alkyl, trifluoromethyl, alkoxy, amino, mono- or di-alkylamino, heteroarylalkyl and aralkyl;

heteroaryl is unsubstituted or substituted by one or two of the same or different groups selected from: halogen, alkyl, cycloalkyl, nitro and amino;

in all its stereoisomeric and tautomeric forms and mixtures thereof in all ratios, and its pharmaceutically acceptable salts, pharmaceutically acceptable solvates, pharmaceutically acceptable polymorphs and prodrugs.

In one embodiment of a compound of formula 1' or 1a', the terms 'alkyl', 'cycloalkyl', 'alkoxy', 'alkenyl', and 'aryl' are limited by their respective carbon content as follows: 'Alkyl' when used alone is '$C_1$-$C_{12}$ alkyl' and when used as part of a substituent group is '$C_1$-$C_4$ alkyl', 'cycloalkyl' is '$C_3$-$C_6$ cycloalkyl', 'alkoxy' is '$C_1$-$C_4$ alkoxy', 'alkenyl' is '$C_2$-$C_6$ alkenyl', and 'aryl' is '$C_6$-$C_{10}$ aryl'.

In embodiments of any of the compounds of formula (1') or (1a'), the groups $R_2$, $R_4$, $R_5$, $R_7$ and U may, independently of each other, have the following definitions. Hence one or more of the groups $R_2$, $R_4$, $R_5$, $R_7$ and U may have the preferred definitions given below:

$R_2$ is hydrogen, nitro, amino, $C_1$-$C_4$alkylamino or formylamino;

$R_4$ is hydrogen or chloro;

$R_5$ is hydrogen or methyl;

$R_7$ is $C(O)OC_1$-$C_4$alkyl or C(O)OH;

U is NH, CO, CHOH or $CH_2$.

In an even further preferred embodiment, the present invention provides tricyclic compounds selected from the following:

2-Amino-4-chloro-6-methyl-10,10-dioxo-10,11-dihydro-5-oxa-10lambda*6*-thia-dibenzo[a,d]cycloheptene-8-carboxylic acid methyl ester;

2-Amino-4-chloro-6-methyl-10,10-dioxo-10,11-dihydro-5-oxa-10lambda*6*-thia-dibenzo[a,d]cycloheptene-8-carboxylic acid;

2-Amino-4-chloro-6-methyl-10,10-dioxo-10,11-dihydro-5-oxa-10lambda*6*-thia-dibenzo[a,d]cycloheptene-8-carboxylic acid sodium salt;

4-Chloro-2-(2-chloro-acetylamino)-6-methyl-10,10-dioxo-10,11-dihydro-5-oxa-10lambda*6*-thia-dibenzo[a,d]cycloheptene-8-carboxylic acid methyl ester;

4-Chloro-2-(2-hydroxy-acetylamino)-6-methyl-10,10-dioxo-10,11-dihydro-5-oxa-10lambda*6*-thia-dibenzo[a,d]cycloheptene-8-carboxylic acid methyl ester;

2-(2-Acetoxy-acetylamino)-4-chloro-6-methyl-10,10-dioxo-10,11-dihydro-5-oxa-10lambda*6*-thia-dibenzo[a,d]cycloheptene-8-carboxylic acid methyl ester;

4-Chloro-6-methyl-10,10-dioxo-2-propionylamino-10,11-dihydro-5-oxa-10lambda*6*-thia-dibenzo[a,d]cycloheptene-8-carboxylic acid methyl ester;

4-Chloro-2-formylamino-6-methyl-10,10-dioxo-10,11-dihydro-5-oxa-10lambda*6*-thia-dibenzo[a,d]cycloheptene-8-carboxylic acid;

4-Chloro-2-formylamino-6-methyl-10,10-dioxo-10,11-dihydro-5-oxa-10lambda*6*-thia-dibenzo[a,d]cycloheptene-8-carboxylic acid sodium salt;

4-Chloro-2-formylamino-6-methyl-10,10-dioxo-10,11-dihydro-5-oxa-10lambda*6*-thia-dibenzo[a,d]cycloheptene-8-carboxylic acid methyl ester;

4-Chloro-2-formylamino-6-methyl-10,10-dioxo-10,11-dihydro-5-oxa-10lambda*6*-thia-dibenzo[a,d]cycloheptene-8-carboxylic acid ethyl ester;

4-Chloro-2-formylamino-6-methyl-10,10-dioxo-10,11-dihydro-5-oxa-10lambda*6*-thia-dibenzo[a,d]cycloheptene-8-carboxylic acid isopropyl ester;

2-[Bis-(2-chloro-ethyl)amino]-4-chloro-6-methyl10,10-dioxo-10,11-dihydro-5-oxa-10lambda*6*-thia-dibenzo[a,d]-cycloheptene-8-carboxylic acid methyl ester;

2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carboxylic acid methyl ester;

4-Chloro-6-methyl-2-piperazin-1-yl-11H-5-oxa-10-thia-dibenzo[a,d]cycloheptene-8-carboxylic acid methyl ester hydrochloride;

4-Chloro-6-methyl-10-oxo-2-piperazin-1-yl-10,11-dihydro-5-oxa-10lambda*4*-thia-dibenzo[a,d]cycloheptene-8-carboxylic acid methyl ester hydrochloride;

4-Chloro-6-methyl-10,10-dioxo-2-piperazin-1-yl-10,11-dihydro-5-oxa-10lambda*6*-thia-dibenzo[a,d]-cycloheptene-8-carboxylic acid methyl ester hydrochloride;

4-Chloro-6-methyl-10,10-dioxo-2-piperazin-1-yl-10,11-dihydro-5-oxa-10lambda*6*-thia-dibenzo[a,d]cycloheptene-8-carboxylic acid methyl ester mesylate;

4-Chloro-6-methyl-10,10-dioxo-2-piperazin-1-yl-10,11-di-hydro-5-oxa-10lambda*6*-thia-dibenzo[a,d]cyclohep-tene-8-carboxylic acid;

4-Chloro-6-methyl-10,10-dioxo-2-piperazin-1-yl-10,11-di-hydro-5-oxa-10lambda*6*-thia-dibenzo[a,d]cyclohep-tene-8-carboxylic acid mesylate;

4-Chloro-2-(4-formyl-piperazin-1-yl)-6-methyl-10,10-di-oxo-10,11-dihydro-5-oxa-10lambda*6*-thia-dibenzo[a,d]cycloheptene-8-carboxylic acid methyl ester;

2-(4-Acetyl-piperazin-1-yl)-4-chloro-6-methyl-10,10-di-oxo-10,11-dihydro-5-oxa-10lambda*6*-thia-dibenzo[a,d]cycloheptene-8-carboxylic acid methyl ester;

4-Chloro-2-[4-(2-hydroxy-ethyl)-piperazin-1-yl]-6-methyl-10,10-dioxo-10,11-dihydro-5-oxa-10lambda*6*-thia-dibenzo[a,d]cycloheptene-8-carboxylic acid methyl ester;

2-(4-Benzyl-piperazin-1-yl)-4-chloro-6-methyl-10,10-di-oxo-10,11-dihydro-5-oxa-10lambda*6*-thia-dibenzo[a,d]cycloheptene-8-carboxylic acid methyl ester;

4-Chloro-6-methyl-2-[4-(2-methyl-benzoyl)-piperazin-1-yl]-10,10-dioxo-10,11-dihydro-5-oxa-10lambda*6*-thia-dibenzo[a,d]cycloheptene-8-carboxylic acid methyl ester;

4-Chloro-2-(4-methanesulfonyl-piperazin-1-yl)-6-methyl-10,10-dioxo-10,11-dihydro-5-oxa-10lambda*6*-thia-dibenzo[a,d]cycloheptene-8-carboxylic acid methyl ester;

4-(4-Chloro-8-methoxycarbonyl-6-methyl-10,10-dioxo-10,11-dihydro-5-oxa-10lambda*6*-thia-dibenzo[a,d]cyclo-hepten-2-yl)-piperazine-1-carboxylic acid benzyl ester;

4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carboxylic acid methyl ester hydrochloride;

4-Chloro-6-methyl-10,10-dioxo-2-piperazin-1-yl-10,11-di-hydro-5-oxa-10lambda*6*-thia-dibenzo[a,d]cyclohep-tene-8-carboxylic acid isopropyl ester;

4-Chloro-2-[1,4]diazepan-1-yl-6-methyl-10,10-dioxo-10,11-dihydro-5-oxa-10lambda*6*-thia-dibenzo[a,d]cyclo-heptene-8-carboxylic acid methyl ester hydrochloride;

4-Chloro-6-methyl-2-morpholin-4-yl-10,10-dioxo-10,11-dihydro-5-oxa-10lambda*6*-thia-dibenzo[a,d]cyclohep-tene-8-carboxylic acid methyl ester;

3-(2-Amino-ethylamino)-4-Chloro-6-methyl-10,10-dioxo-10,11-dihydro-5-oxa-10lambda*6*-thia-dibenzo[a,d]cy-cloheptene-8-carboxylic acid methyl ester hydrochloride;

4-Chloro-6-methyl-10,10-dioxo-3-piperazin-1-yl-10,11-di-hydro-5-oxa-10lambda*6*-thia-dibenzo[a,d]cyclohep-tene-8-carboxylic acid methyl ester hydrochloride;

(4-Chloro-6-methyl-10,10-dioxo-2-piperazin-1-yl-10,11-di-hydro-5-oxa-10lambda*6*-thia-dibenzo[a,d]cyclohep-tene-8-yl)-acetic acid methyl ester hydrochloride;

4-Chloro-6-methyl-10,10-dioxo-2-piperazin-1-yl-10,11-di-hydro-5-oxa-10lambda*6*-thia-dibenzo[a,d]cyclohep-tene-8-carbaldehyde;

[4-Chloro-2-(4-ethyl-piperazin-1-yl)-6-methyl-10,10-di-oxo-10,11-dihydro-5-oxa-10lambda*6*-thia-dibenzo[a,d]cycloheptene-8-yl]-methanol;

4-Chloro-6-methyl-10,10-dioxo-2-piperazin-1-yl-10,11-di-hydro-5-oxa-10lambda*6*-thia-dibenzo[a,d]cyclohep-tene-8-carboxylic acid cyclopropylamide hydrochloride;

2-Amino-4-chloro-6-methyl-10,10-dioxo-10,11-dihydro-5H-10lambda*6*-thia-5-aza-dibenzo[a,d]-cycloheptene-8-carboxylic acid methylester;

4-Chloro-2-formylamino-6-methyl-10,10-dioxo-10,11-di-hydro-5H-10-lambda*6*-thia-5-aza-dibenzo[a,d]-cyclo-heptene-8-carboxylic acid methyl ester;

5-10,10-Trioxo-10,11-dihydro-5H-10-lamda*6*-thia-dibenzo[a,d]cycloheptene-8-carboxylic acid methyl ester;

5-Hydroxy-10,10-dioxo-10,11-dihydro-5H-10lambda*6*-thia-dibenzo[a,d]cycloheptene-8-carboxylic acid methyl ester; and 10,10-Dioxo-10,11-dihydro-5H-10lambda*6*-thia-dibenzo[a,d]cycloheptene-8-carboxylic acid methyl ester;

All the compounds of the present invention also include all stereoisomeric forms and mixtures thereof in all ratios and their pharmaceutically acceptable salts, solvates and polymorphs. Furthermore, all the compounds of the present invention are a subject of the present invention in the form of their prodrugs and other derivatives, for example in the form of their esters and amides.

According to a further feature of the present invention there are provided processes for the synthesis of compounds of the present invention of general formula (1a) or (1'), more particularly the compounds of the general formula (1a) or (1a').

One such process for the preparation of a compound of formula (1a) or (1a')

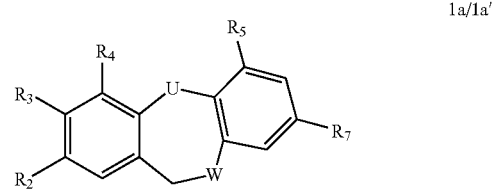

wherein U is O and W is SO$_2$, SO or S (formula (1a) or U is NH and W is SO$_2$ (formula (1a')); R$_2$, R$_3$, R$_4$, R$_5$ and R$_7$ are as defined above, comprises subjecting a compound of formula E:

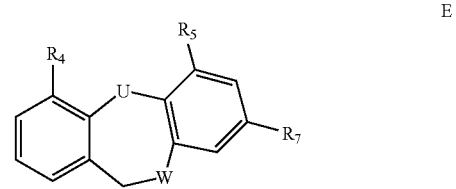

wherein U is O and W is SO$_2$, SO or S (formula (1a) or U is NH and W is SO$_2$ (formula (1a'), R$_4$, R$_5$ and R$_7$ are as defined above, to nitration using any standard procedure known in the art to obtain a nitro derivative of general formula E1 (major component) or E1' (minor component):

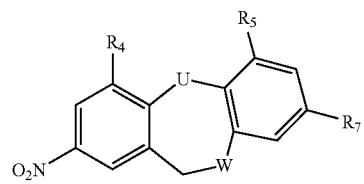

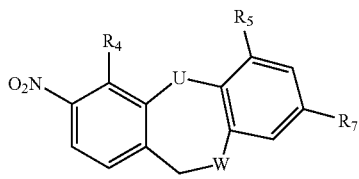

wherein U is O or NH, and W, $R_4$, $R_5$ and $R_7$ are as defined above.

The resulting nitro derivative of the general formula E1 or E1' may be subjected to reduction by using any conventional reduction method known to one skilled in the art, to obtain an amino derivative of the general formula E2 or E2', respectively:

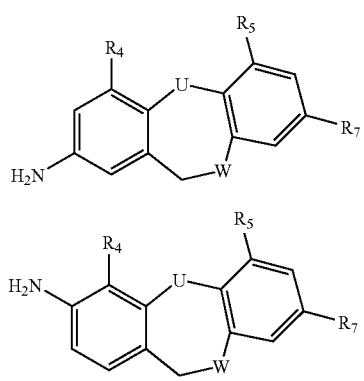

wherein U is O or NH, and W, $R_4$, $R_5$ and $R_7$ are as defined above.

In the process described above, W is preferably $SO_2$.

The amino derivative of the general formula E2 or E2' may further be functionalised/derivatised at the primary amino group, and/or at an amino group located at any other position of the compound, by subjecting it to a series of reactions to obtain various derivatives, which are also incorporated in the general formula (1a) or (1'). The resulting compound may be converted into a pharmaceutically acceptable salt or prodrug.

The amino derivative of the general formula E2 or E2' or any other compound of the formula 1, 1', 1a or 1a', in which $R_7$ represents alkyl carboxylate, may be subjected to alkaline hydrolysis to obtain an acid and then may be reacted with an amine to form a substituted or unsubstituted amide. The resulting compound may optionally be converted into a pharmaceutically acceptable salt.

The amino derivative of the general formula E2 or E2' or any other compound of the formula 1, 1', 1a or 1a', in which $R_7$ represents alkyl carboxylate, may be subjected to hydrolysis followed by standard reduction reactions to form a —$CH_2OH$ derivative, which further may be oxidized to —CHO. The resulting compound may optionally be converted into a pharmaceutically acceptable salt or prodrug.

The amino derivative of the general formula E2 or E2' or any other compound of the formula 1, 1', 1a or 1a', in which $R_7$ represents —$CH_2OH$ may be subjected to standard reactions to convert $R_7$ into —$CH_2Cl$, which further can be converted to —$CH_2CN$, which in turn can be converted to —$CH_2COOH$ by hydrolysis and which may further be esterified to form an ester such as —$CH_2COOC_1$-$C_4$alkyl. The resulting compound may optionally be converted into a pharmaceutically acceptable salt or prodrug.

The compound of formula E (above) is prepared by either a) subjecting a compound of formula D

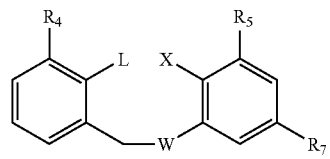

wherein W is $SO_2$, SO or S, and $R_4$, $R_5$ and $R_7$ are as defined herein above, L is $NO_2$ or $NH_2$, and X is halogen, to reduction where L is $NO_2$ to convert the $NO_2$ into $NH_2$ and then cyclisation to obtain the cyclic compound of the general formula E (wherein $R_4$, $R_5$ and $R_7$ are as defined herein above; and U is NH), or b) subjecting a compound of the general formula D (wherein $R_4$, $R_5$ and $R_7$ are as defined herein above; L is protected hydroxy group; and X is halogen) to deprotection to obtain the corresponding hydroxy compound, subjecting the hydroxyl compound to cyclisation to obtain a compound of the general formula E (wherein $R_4$, $R_5$ and $R_7$ are as defined herein above; and U is O).

In a preferred embodiment, W in the compound of formula D above is $SO_2$.

The compound of the formula D (above) may be obtained by alkylating an appropriately substituted o-halo mercaptobenzoic acid of the formula A:

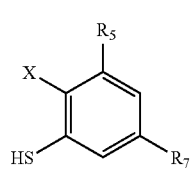

wherein X is a halogen, $R_7$ is an alkyl carboxylate, $R_5$ is as defined above, with an appropriately substituted 1-halomethyl-2-(protected)hydroxybenzene or 1-halomethyl-2-nitrobenzene of formula B:

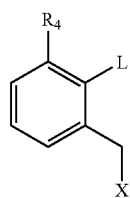

wherein X is a halogen, L is either protected hydroxy or nitro, $R_4$ is as defined above, to obtain a sulfanyl compound of the formula C:

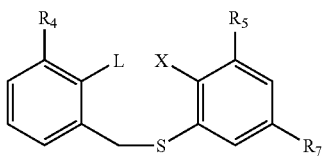

wherein X is halogen and L is a protected hydroxy group, such as t-butyl-dimethylsilyloxy or nitro, $R_7$ is alkyl carboxylate, $R_4$ and $R_5$ are as defined above; and optionally oxidizing the compound of formula C to its sulfoxide or sulfonyl derivative.

The compounds of the present invention can be prepared in a number of ways using methods well known to the skilled person. Examples of methods to prepare the present compounds are described below and illustrated in Scheme I but not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted. Clearly, such factors will also influence the choice of reagent to be used in the synthetic steps.

The reagents, reactants and intermediates used in the following processes are either commercially available or can be prepared according to standard literature procedures known in the art. The starting compounds and the intermediates used for the synthesis of compounds of the present invention, are referred to with general symbols namely A, A-i, A-ii, A-iii, A-iv, B, B-i, B-ii, C, D, E, E1, E1', G-i. P, Q, Q1, Q2, E2 and E2' of which the compounds designated as A, B, C, D, E, E1, E1', P, Q, Q1, Q2, Q3, E2 and E2' are the key intermediates. The key intermediates B, C, D, E, E1, E1', E2 and E2' may represent more than one type of compound depending on the definition of the U group. For instance:

1. In the intermediates of general formula B, C and D, the substituent L may represent a group selected from amino, nitro and a protected hydroxy group, wherein the protective group may be selected from t-butyl-dimethylsilyl (TBDMS), acetyl, and the like;

2. In the intermediate of general formula E, E1, E1', E2 and E2' the U group may be selected from O or NH.

Throughout the process description, the corresponding substituent groups in the various formulae representing starting compounds and intermediates have the same meanings as that for the compounds of formula (1a) or (1a') unless stated otherwise.

A general route for the synthesis of compounds of the present invention involves: alkylation of an appropriately substituted o-bromo mercaptobenzoic acid (A) with an appropriately substituted (2-halomethylphenoxy) tert-butyldimethylsilane (B), followed by oxidation of the resulting sulfanyl derivative (C) to its sulfonyl derivative (D). The sulfonyl derivative (D), thus obtained may then be subjected to deprotection of the silyl ether group followed by in situ cyclisation and a series of reaction steps (understood by those skilled in the art) for suitable modification of the functional groups, to obtain a desired compound of the invention, more particularly a compound of the general formula (1a) or (1a'). Alternatively, the sulfanyl derivative (C) may be subjected to a series of reactions involving desilylation and cyclisation, followed by nitration which may result in partial oxidation of the ring sulfur atom into its sulfoxide (Q1) which may be converted to a desired compound of the invention, more particularly to a compound of the general formula (1a) or (1a') by standard procedures known to those skilled in the art.

Alternatively, alkylation of an appropriately substituted o-bromo mercaptobenzoic acid (A) may be carried out with an appropriately substituted 1-halomethyl-2-nitrobenzene (B), to obtain a sulfanyl derivative (C) which may then be oxidized to its sulfonyl derivative (D). The resulting sulfonyl derivative (D), wherein L is $NO_2$ may be subjected to reduction with an appropriate reducing agent for the conversion of nitro to amino group, followed by cyclisation and a series of reaction steps (understood by those skilled in the art) for suitable modification of the functional groups, to obtain a desired compound of the invention, more particularly a compound of the general formula (1a) or (1a').

Preferred processes for the preparation of compounds of the present invention are set forth in the following Scheme I:

Process 1: Preparation of key intermediates of general formula E2 or E2':

Step (i): Preparation of the Compounds of General Formula C:

A thiol compound of the general formula A (wherein $R_5$ is as defined herein above; $R_7$ represents alkyl carboxylate; X represents halogen, preferably Br) may be subjected to a nucleophilic substitution, more particularly to an S alkylation, with a compound of the general formula B (wherein $R_4$ is as defined herein above; X represents halogen, preferably Br; and L represents a protected hydroxy group such as t-butyl-dimethylsilyloxy), in the presence of a base in an aprotic solvent, over a time period of 0.5 h to 10 h, at a temperature range of 0° C. to ambient, in the presence or absence of an inert atmosphere using gases such as $N_2$, Ar, He, and processed in a manner known to one skilled in the art to obtain the sulfanyl derivative, a compound of the general formula C (wherein $R_4$ and $R_5$ are as defined herein above; $R_7$ represents alkyl carboxylate; X represents halogen, preferably Br; and L represents a protected hydroxy group such as the t-butyl-dimethylsilyloxy group). When the thiol compound of the general formula A is alkylated with the compound of general formula B (wherein L represents $NO_2$), the key intermediate of formula C (wherein $R_4$ and $R_5$ are as defined herein above; $R_7$ represents alkyl carboxylate; X represents halogen, preferably Br; and L represents $NO_2$) is obtained.

The base used in the above substitution reaction may be an organic or an inorganic base. The organic base may be selected from triethylamine, pyridine, lutidine, collidine or a mixture thereof. The inorganic base may be selected from sodium hydroxide, potassium hydroxide, sodium carbonate, potassium carbonate, sodium hydride, potassium hydride, sodamide, n-butyllithium. The amount of base used may range from 1 to 5 equivalents, preferably 1 to 3 equivalents of the starting compound of general formula A.

The aprotic solvent, in which the above substitution reaction is carried out, may be selected from a hydrocarbon such as hexane, benzene, toluene, xylene; or a halogenated hydrocarbon such as dichloroethane, chloroform; or an ether such as tetrahydrofuran (THF), dioxane, diethyl ether, t-butyl methyl ether; or any other solvent such as DMF or DMSO suitable for carrying out the substitution reaction.

Step (ii): Conversion of the Compounds of Formula C to the Compounds of Formula D:

The compounds of the general formula C, as obtained in the above step (i) (wherein $R_4$ and $R_5$ are as defined herein above, $R_7$ represents alkyl carboxylate; L represents t-butyl-dimethylsilyloxy or $NO_2$; and X represents halogen, preferably Br), may be oxidized using an oxidizing agent selected from hydrogen peroxide; m-chloroperbenzoic acid (m-CPBA), potassium perchlorate or OXONE™, preferably m-CPBA, in the presence of an organic solvent selected from a halogenated hydrocarbon such as dichloromethane and a protic solvent such as methanol, ethanol and the like, at a temperature range of 0° C. to reflux, over a time period of 1 h to 8 h, and further processed in a manner known to one skilled in the art to obtain the corresponding sulfonyl derivative, a compound of the general formula D (wherein $R_4$ and $R_5$ are as defined herein above; $R_7$ represents alkyl carboxylate; L represents t-butyl-dimethylsilyloxy or $NO_2$; and X represents halogen, preferably Br).

The compound of formula D (wherein L represents $NO_2$) may be subjected to reduction with an appropriate reducing agent to obtain its corresponding amine derivative, a compound of formula D (wherein $R_4$ and $R_5$ are as defined herein above; $R_7$ represents alkyl carboxylate; L represents $NH_2$; and X represents halogen, preferably Br).

The reduction reaction may be carried out using various reduction methods known to one skilled in the art, for example, by catalytic hydrogenation in presence of a catalyst such as Raney Nickel, palladium-carbon, platinum-carbon, rhodium-carbon. Other reduction methods such as those involving use of sodium borohydride, sodium cyanoborohydride, tin-hydrochloric acid or iron-hydrochloric acid, may also be used for carrying out the reduction reaction. However, the reduction method involving catalytic hydrogenation using Raney Nickel as the catalyst, is the preferred method.

The organic solvent used for carrying out the reduction reaction may be selected from N,N-dimethylformamide (DMF), tetrahydrofuran (THF), ethyl acetate, ethanol, methanol, toluene, benzene, diethyl ether, dioxane; and DMF being the preferred solvent.

Step (iii): Conversion of the Compounds of Formula D to the Compounds of Formula E.

The compound of the general formula D as obtained in the above step (ii) (wherein $R_4$ and $R_5$ are as defined herein above; $R_7$ represents alkyl carboxylate; L represents $NH_2$; and X represents halogen, preferably Br) may undergo cyclisation in the presence of an inorganic base such as sodium hydride. The cyclisation reaction may be carried out in an aprotic solvent such as DMF, in the presence or absence of an inert atmosphere, at a temperature range of 0° C. to 100° C., over a time period of 2 h to 24 h to obtain the cyclic intermediate, a compound of the general formula E (wherein $R_4$ and $R_5$ are as defined herein above; $R_7$ represents alkyl carboxylate; and U represents NH).

SCHEME I

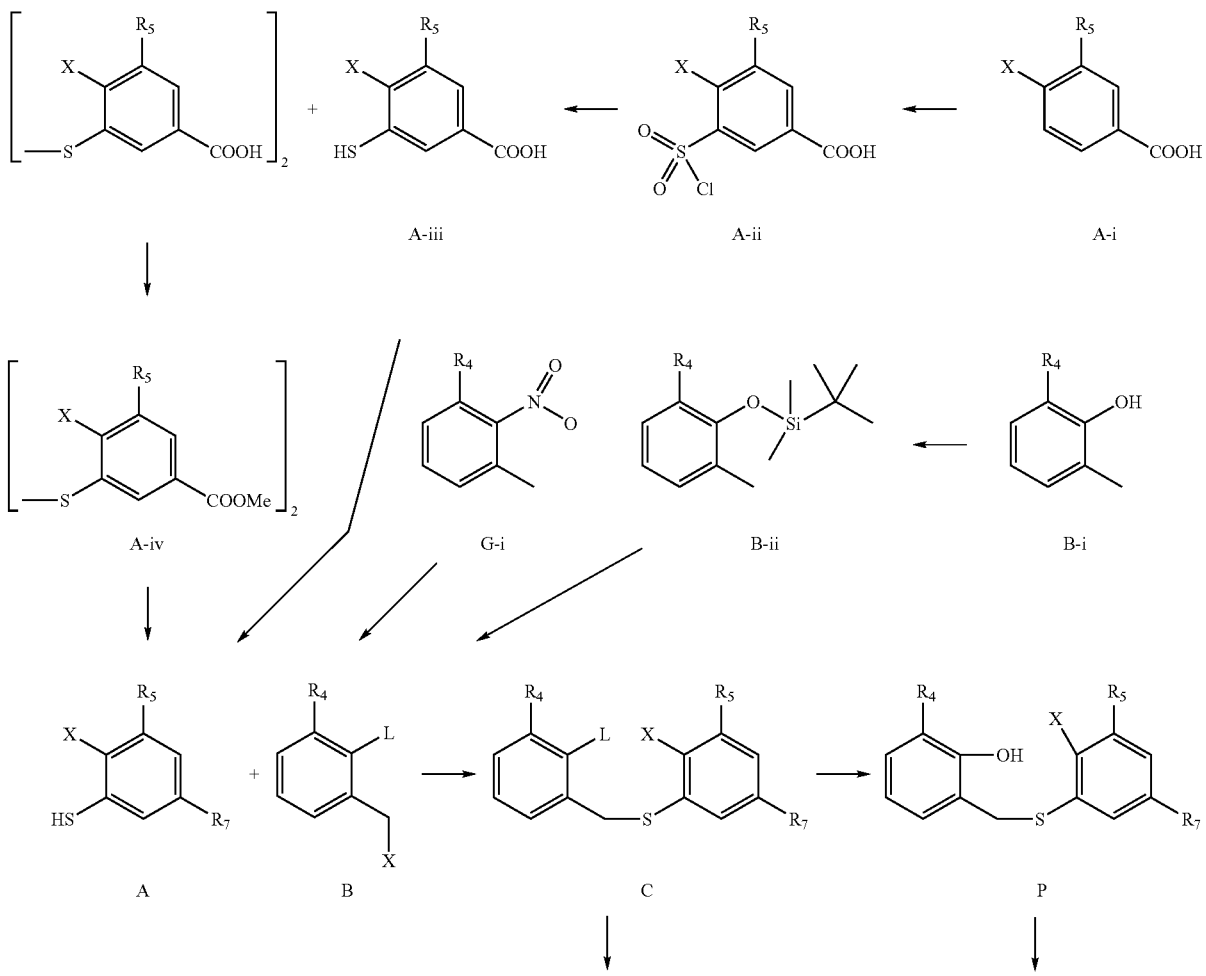

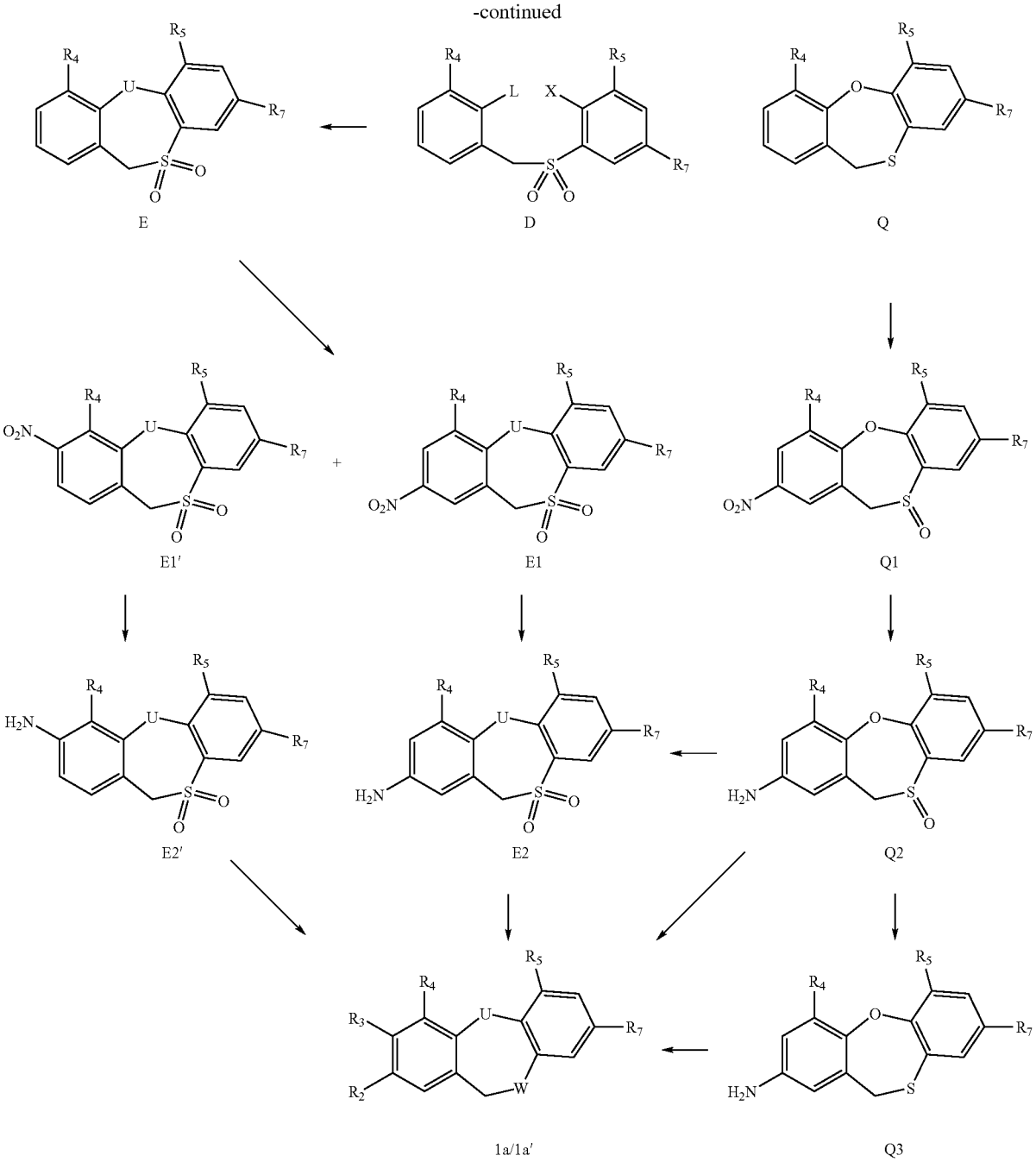

1a/1a'

$R_2$, $R_3$, $R_4$, $R_5$, $R_7$, U and W are as described in 1a or 1a'

Alternatively, the compound of the general formula D (wherein $R_4$ and $R_5$ are as defined herein above; $R_7$ represents alkyl carboxylate; L represents t-butyl-dimethylsilyloxy; and X represents halogen, preferably Br) may be subjected to deprotection of the silyl ether group using a suitable deprotecting reagent such as tetraalkylammonium fluoride to obtain the corresponding hydroxy compound which may also undergo in situ cyclisation to obtain the cyclic intermediate, a compound of the general formula E (wherein $R_4$ and $R_5$ are as defined herein above; $R_7$ represents alkyl carboxylate; and U represents O).

Step (iv): Conversion of the Compounds of Formula E to the Compounds of Formula E1 or E1'.

The compound of general formula E as obtained in the above step (ii) (wherein $R_4$ and $R_5$ are as defined herein above; $R_7$ represents alkyl carboxylate) may be subjected to nitration using nitric acid-sulfuric acid as per any standard nitration procedure known in the art. For instance, the nitration reaction may be carried out at a temperature range of 0° C. to 40° C., over a time period of 1 h to 20 h to obtain the corresponding nitro derivative, a compound of the general formula E1 (wherein $R_4$ and $R_5$ are as defined herein above;

$R_2$ represents $NO_2$; and $R_7$ represents alkyl carboxylate) or E1' (wherein $R_4$ and $R_5$ are as defined herein above; $R_3$ represents $NO_2$; and $R_7$ represents alkyl carboxylate).

Step (v): Conversion of the Compounds of Formula E1 or E1' to the Compounds of Formula E2 or E2'.

The nitro group in the compound of formula E1 or E1' as obtained in the above step (iv) (wherein $R_4$ and $R_5$ are as defined herein above; $R_2$ or $R_3$ represents $NO_2$ and $R_7$ represents alkyl carboxylate) may be subjected to reduction by using a suitable reducing agent in an organic solvent at ambient temperature and worked up in a manner known to one skilled in the art, to obtain the corresponding amino derivative, a compound of the general formula E2 (wherein $R_4$ and $R_5$ are as defined herein above; $R_2$ represents $NH_2$; and $R_7$ represents alkyl carboxylate) or E2' (wherein $R_4$ and $R_5$ are as defined herein above; $R_3$ represents $NH_2$; and $R_7$ represents alkyl carboxylate).

The reduction reaction may be carried out using various reduction methods known to one skilled in the art, for example, by catalytic hydrogenation in presence of a catalyst such as Raney Nickel, palladium-carbon, platinum-carbon, Rhodium-carbon. Other reduction methods such as those involving use of sodium borohydride, sodium cyanoborohydride, tin-hydrochloric acid (Sn—HCl) or iron-hydrochloric acid (Fe—HCl), may also be used for carrying out the reduction reaction. However, the reduction method involving catalytic hydrogenation using Raney Nickel as the catalyst, is the preferred method. The organic solvent used for carrying out the reduction reaction may be selected from dimethylformamide (DMF), tetrahydrofuran (THF), ethyl acetate, ethanol, methanol, toluene, benzene, diethyl ether, dioxane; and DMF being the preferred solvent.

Process 2: Preparation of the Key Intermediates of General Formulae P, Q, Q1, Q2, Q3 and E2:

Step (i): Preparation of the Key Intermediate of General Formula P:

A compound of the general formula C as obtained in Process 1-step (i) (wherein $R_4$ and $R_5$ are as defined herein above; $R_7$ represents alkyl carboxylate; L represents t-butyl-dimethylsilyloxy; and X represents halogen, preferably Br) may be subjected to deprotection of the silyl ether group by treating the said compound with a suitable deprotecting reagent in an appropriate organic solvent in the presence or absence of an inert atmosphere using a gas such as nitrogen at a temperature range of 0° C. to reflux over a time period of 0.5 h to 3 h (as reported in Tetrahedron, 1985, 41, 3257) to obtain the hydroxy intermediate, a compound of the general formula P (wherein $R_4$ and $R_5$ are as defined herein above; $R_7$ represents alkyl carboxylate; and X represents halogen, preferably Br).

The deprotecting agent used in the above step may be selected from a chemoselective reagent such as tetraalkylammonium halide, preferably tetrabutylammonium fluoride, and any other suitable deprotecting agent such as hydrogen fluoride (HF), HF-pyridine, acetic acid, trifluoroacetic acid (TFA), hydrochloric acid.

The organic solvent in which the deprotection (desilylation) reaction is carried out may be selected from tetrahydrofuran (THF), methanol, methylene dichloride, chloroform, benzene, toluene and any other suitable solvent.

Step (ii): Conversion of the Compound of Formula P to the Compound of Formula Q:

The compound of the general formula P as obtained in the above step (i) (wherein $R_4$ and $R_5$ are as defined herein above; $R_7$ represents alkyl carboxylate; and X represents halogen, preferably Br) may undergo cyclisation in the presence of a base such as potassium carbonate. The cyclisation may be carried out in an aprotic solvent such as DMF, in the presence or absence of an inert atmosphere, at a temperature range of 0° C. to 100° C., over a time period of 2 h to 24 h to obtain the cyclic intermediate, a compound of the general formula Q (wherein $R_4$ and $R_5$ are as defined herein above; $R_7$ represents alkyl carboxylate).

Step (iii): Conversion of the Compound of Formula Q to the Compound of Formula Q1:

The compound of general formula Q as obtained in the above step (ii) (wherein $R_4$ and $R_5$ are as defined herein above; $R_7$ represents alkyl carboxylate) may be subjected to nitration using nitric acid-sulfuric acid as per any standard nitration procedure known in the art. For instance, the nitration reaction may be carried out at a temperature range of 0° C. to 40° C., over a time period of 1 h to 20 h to obtain the corresponding nitro derivative, a compound of the general formula Q1 (wherein $R_4$ and $R_5$ are as defined herein above; $R_2$ represents $NO_2$; and $R_7$ represents alkyl carboxylate). This reaction may also result in the partial oxidation of the ring sulfur atom into its sulfoxide.

Step (iv): Conversion of the Compound of Formula Q1 to the Compound of Formula Q2:

The nitro group in the compound of formula Q1 as obtained in the above step (iii) (wherein $R_4$ and $R_5$ are as defined herein above; $R_2$ represents $NO_2$; and $R_7$ represents alkyl carboxylate) may be subjected to reduction by using a suitable reducing agent in an organic solvent at ambient temperature and worked up in a manner known to one skilled in the art, to obtain the corresponding amino derivative, a compound of the general formula Q2 (wherein $R_4$ and $R_5$ are as defined herein above; $R_2$ represents $NH_2$; and $R_7$ represents alkyl carboxylate).

The reduction reaction may be carried out using various reduction methods known to one skilled in the art, for example, by catalytic hydrogenation in presence of a catalyst such as Raney nickel, palladium-carbon, platinum-carbon, Rhodium-carbon. Other reduction methods such as those involving use of sodium borohydride, sodium cyanoborohydride, tin-hydrochloric acid (Sn—HCl) or iron-hydrochloric acid (Fe—HCl), may also be used for carrying out the reduction reaction. However, the reduction method involving catalytic hydrogenation using Raney nickel as the catalyst, is the preferred method.

The organic solvent used for carrying out the said reduction reaction may be selected from dimethylformamide (DMF), tetrahydrofuran (THF), ethyl acetate, ethanol, methanol, toluene, benzene, diethyl ether, dioxane; and DMF being the preferred solvent.

Step (vi): Conversion of the Compounds of Formula Q2 to the Compounds of Formula Q3:

The compounds of the general formula Q2, as obtained in the above step (i) (wherein $R_4$ and $R_5$ are as defined herein above; $R_2$ represents $NH_2$; and $R_7$ represents alkyl carboxylate; W is SO;), may be reduced using standard procedures to obtain the compounds of the general formula Q3 (wherein $R_4$ and $R_5$ are as defined herein above; $R_2$ represents $NH_2$; and $R_7$ represents alkyl carboxylate; W is S;).

Step (vi): Conversion of the Compounds of Formula Q2 to the Compounds of Formula E2:

The compounds of the general formula Q2, as obtained in the above step (i) (wherein $R_4$ and $R_5$ are as defined herein above; $R_2$ represents $NH_2$; and $R_7$ represents alkyl carboxylate), may be oxidized using an oxidizing agent selected from hydrogen peroxide; m-chloroperbenzoic acid (m-CPBA), potassium perchlorate and OXONE™, preferably m-CPBA, in the presence of an organic solvent selected from a halogenated hydrocarbon such as dichloromethane and a protic solvent such as methanol, ethanol and the like, at a temperature range of 0° C. to reflux, over a time period of 1 h to 8 h, and further processed in a manner known to one skilled in the art to obtain the corresponding sulfonyl derivative, a compound of the general formula (1a) or (1a') (wherein $R_4$ and $R_5$ are as defined herein above; $R_2$ represents $NH_2$; and $R_7$ represents alkyl carboxylate).

Process 3: Conversion of the Key Intermediates of Formulae E, E1, E1', Q2, Q3, E2 and E2' to the Respective Acids.

The key intermediates, the compounds of the general formulae E, E1, E1', Q2, Q3, E2 and E2' as obtained according to the above described processes (wherein $R_2$, $R_3$, $R_4$, $R_5$ and U are as defined herein above; $R_7$ represents a carboxylate ester group such as alkylcarboxylate or cycloalkylcarboxylate or substituted cycloalkyl carboxylate group, preferably the methyl carboxylate) may be subjected to hydrolysis using acidic conditions or alkaline conditions, more preferably using an alkali such as sodium hydroxide, in a solvent or a solvent mixture such as THF-water at a temperature range of 0° C. to 60° C., over a time period of 0.5 h to 10 h, and worked up in a manner known to one skilled in the art to obtain the corresponding carboxylic acids represented by the general formulae E, E1, E1', Q2, Q3, E2 and E2' (wherein $R_2$, $R_3$, $R_4$, $R_5$ and U are as defined herein above; $R_7$ represents —COOH).

Process 4: Derivatisation of the Key Intermediate of Formula Q2, Q3, E2 and E2'.

It will be appreciated by one skilled in the art that compounds which fall within the general formula Q2, Q3, E2 and E2', may in some instances, be functionalised to obtain further derivatives.

Any one of the compounds represented by the general formula Q2, Q3, E2 and E2', in Scheme-I (wherein $R_4$ and $R_5$ are as defined herein above; $R_2$ or $R_3$ represents $NH_2$; $R_7$ represents carboxylic acid or alkyl carboxylate group; U is O or NH) may further be functionalised/derivatised at the primary amino group ($R_2$ or $R_3$) by subjecting it to a series of reactions known in the literature to obtain various derivatives, represented by the general formula (1a) or (1a').

The compounds represented by the general formula Q2, Q3, E2 and E2', in Scheme-I (wherein $R_4$ and $R_5$ are as defined herein above; $R_2$ or $R_3$ represents $NH_2$; $R_7$ represents carboxylic acid; U is O or NH) and the amino derivatives (mentioned above) may further be functionalised/derivatised by reacting with suitable amines to obtain substituted or unsubstituted amide.

The compounds represented by the general formula Q2, Q3, E2 and E2', and the derivatives obtained in above step, in which $R_7$ represents alkyl carboxylate, may be subjected to hydrolysis followed by standard reduction reactions to form the —$CH_2OH$ derivatives which may be oxidized to obtain the formyl derivative.

The derivatives obtained in above step in which $R_7$ represents —$CH_2OH$ may be subjected to standard reactions to form —$CH_2Cl$, which further can be converted to —$CH_2CN$ using NaCN, which can be converted to —$CH_2COOH$ by hydrolysis and to —$CH_2COOC_1$-$C_4$alkyl by esterification.

These derivatives may subsequently be converted into their organic or inorganic salts, like the methane sulfonic acid salts, by treatment with methane sulfonic acid in a dry solvent like ethyl acetate, dioxane, diethyl ether, methanol, ethanol or any other suitable solvent and processed in a manner known to one skilled in the art.

Process 5: Preparation of the Thiol Compound of General Formula A:

Step (i): Preparation of Compounds of the General Formulae A-i and A-ii:

An appropriately substituted aryl halide, preferably an appropriately substituted 4-halo-benzoic acid of general formula A-i (wherein $R_5$ is as defined herein above; $R_7$ represents COOH; and X represents halogen, preferably Br) may be, treated with chlorosulfonic acid at a temperature range of 40° C. to 140° C., for a time period of 4 h to 24 h by following a standard procedure to obtain the corresponding chlorosulfonyl derivative, a compound of general formula A-ii (wherein $R_5$ is as defined herein above; $R_7$ represents COOH; and X represents halogen, preferably Br).

The compound of formula A-i may be either commercially available or be obtained by subjecting an appropriately substituted 4-nitro-benzoic acid to a sequence of reactions namely reduction, diazotisation and a Sandmeyer reaction. For example, the nitro group in the 4-nitrobenzoic acid may be reduced to the corresponding amine by catalytic hydrogenation or transfer hydrogenation, with ammonium formate in presence of a catalyst such as Pd, Pt, Pd—C, Raney-Ni, in an organic solvent such as ethyl acetate, methanol, ethanol, isopropanol, DMF, or a mixture thereof. This reduction may also be carried out by any conventional method known in the art, such as that involving use of Zn and HCl or $CoCl_2$ (Ind. J. Chem., 1994, 33B, 758) or $NaBH_4$. The resulting amino compound may then be subjected to diazotisation followed by a Sandmeyer reaction to obtain the desired compound of general formula A-i (wherein $R_5$ is as defined herein above; $R_7$ represents COOH; and X represents halogen, preferably Br).

Step (ii): Conversion of the Compounds of Formula A-ii to the Compounds of Formula A-iii:

A compound of the general formula A-ii as obtained in the above step (i) (wherein $R_5$ is as defined herein above; $R_7$ represents COOH; and X represents halogen, preferably Br) may be subjected to reduction under acidic condition, preferably the reduction reaction may be carried out using glacial acetic acid-stannous chloride in HCl—$H_2O$ (4:1 v/v) with stirring, at a temperature of 80° C. for a time period of 1 h to obtain a thiol compound of general formula A-iii ($R_5$ is as defined herein above; $R_7$ represents COOH; and X represents halogen, preferably Br). In the process of this reaction a disulfide is also obtained as a major by-product, which may be converted to its thiol compound of formula A-iii by subjecting it to reductive cleavage using triphenylphosphine in aqueous methanol as reported in (Synthesis, 59, 1974) or by procedures known to one skilled in the art.

Step (iii): Conversion of the Compound of Formula A-iii (and its Disulfide) to the Compound of Formula A (and the Compound of Formula A-iv):

The thiol compound of formula A-iii as obtained in the above step (ii), (wherein $R_5$ is as defined herein above; $R_7$ represents COOH; and X represents halogen, preferably Br) and its disulfide may be esterified by refluxing with an appropriate alcohol such as methanol in the presence of a mineral acid such as sulphuric acid or hydrochloric acid or by any other standard method known in the art, for example, treating the compound of formula A-iii with thionyl chloride and an appropriate alcohol such as methanol, to obtain the corresponding ester of general formula A (wherein $R_5$ is as defined herein above; $R_7$ represents alkyl carboxylate; and X represents halogen, preferably Br) along with its dimer ester of the general formula A-iv. The most preferred method may involve treating the mixture of the compound of formula A-iii and its dimer in a solvent such as methanol with a mixture of 15% MeOH-conc. $H_2SO_4$ added dropwise under reflux and with stirring for a time period of 6 h to 24 h.

The aryl disulfide ester of the general formula A-iv may be converted to the compound of general formula A using a reported procedure (Synthesis, 59, 1974), more specifically it involves the reduction of compound of formula A-iv using triphenylphosphine or sodium borohydride or sodium cyanoborohydride etc, at an ambient temperature with stirring for a time period of 15 h in a protic solvent mixture such as methanol:water (4:1 v/v) and it may be further processed in a manner known to one skilled in the art.

Process 6-1: Preparation of Compounds of the General Formula B:

Step (i): Preparation of Compound of Formula B-ii:

The hydroxy group in an appropriately substituted o-cresol of general formula B-i (wherein $R_4$ is as defined herein above) may be protected using any standard procedure known in the art. Thus, the compound of general formula B-i may be treated with a suitable hydroxy protecting reagent, to obtain the corresponding hydroxy protected derivative of general formula B-ii (wherein $R_4$ is as defined herein above). Suitable examples of hydroxy protecting reagent are: acetyl chloride, acetic anhydride, benzoyl chloride, benzoic anhydride, benzyl chloroformate, hexamethyldisilazane, trimethylsilyl chloride, t-butyldimethylsilyl chloride etc. According to the present invention, preferred protecting groups are acetyl or t-butyldimethyl silyl group, more preferably, t-butyldimethyl silyl group. Accordingly, the compound of formula B-i may be treated with t-butyl dimethylsilyl chloride, to obtain the t-butyldimethylsilyloxy derivative of general formula B-ii (wherein $R_4$ is as defined herein above) in accordance with methods known in the art Step (ii): Conversion of the Compound of Formula B-ii to the Compound of Formula B:

The compound of formula B-ii, as obtained in the above step-i (wherein $R_4$ is as defined herein above) may be treated with a conventional halogenating reagent known in the art so that the methyl group in the compound of formula B-ii is converted to a methyl halide group. Thus, the compound of formula B-ii may be subjected to a halogenation reaction in accordance with methods known in the art which involves treating the said compound with a suitable halogenating agent, such as N-bromosuccinimide (NBS) in the presence of an oxidising agent, such as benzoyl peroxide or 2,2'-azobisisobutyronitrile (AIBN) in a solvent such as $CCl_4$, over a time period of 2 h to 24 h, to obtain the compound of general formula B (wherein $R_4$ is as defined herein above; X represents halogen, preferably Br; and L represents t-butyldimethyl silyloxy group).

Process 6-2: Preparation of the Compound of Formula B from the Compound of Formula G-i:

The compound of general formula B (wherein $R_4$ is as defined herein above; X represents halogen, preferably Br; and L represents $NO_2$) may also be synthesized by subjecting an appropriately substituted compound of general formula G-i (wherein $R_4$ is as defined herein above) to halogenation in a manner similar to that described in Process 6-1-Step (ii).

Process 7: Preparation of a Compound of the General Formula (1a')

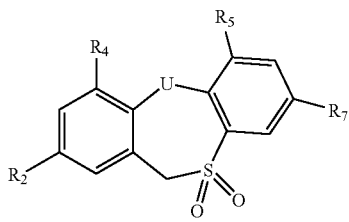

wherein U is C(O), CHOH or $CH_2$; $R_2$, $R_4$, $R_5$ and $R_7$ are as defined above, comprises subjecting a compound of formula M:

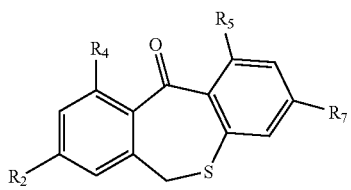

wherein $R_2$, $R_4$, $R_5$ and $R_7$ are as defined above, to oxidation process using any standard procedure known in the art. Compound M can be prepared by the reported procedure (J. Med. Chem., 21, 10, 1035, (1978)). The resultant compound may be subjected to standard reduction processes to obtain compounds of formula (1a') wherein U is CHOH or $CH_2$; $R_2$, $R_4$, $R_5$ and $R_7$ are as defined above.

It will be appreciated by those skilled in the art that the compounds of the present invention may also be utilized in the form of their pharmaceutically acceptable salts or solvates thereof. The pharmaceutically acceptable salts of the compounds of the present invention are in particular salts which are non-toxic, or which can be used physiologically.

Thus, when the compounds of the present invention represented by the general formula (1a) or (1'), more particularly by the general formula (1a) or (1a') contain one or more basic groups, i.e. groups which can be protonated, they can form an addition salt with a non-toxic inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art.

Thus, when the compounds of the present invention represented by the general formula (1a) or (1'), more particularly by the general formula (1a) or (1a') contain an acidic group they can form an addition salt with a suitable base. For example, such salts of the compounds of the present invention may include their alkali metal salts such as Li, Na, and K salts, or alkaline earth metal salts like Ca, Mg salts, or aluminium salts, or salts with ammonia or salts of organic bases such as lysine, arginine, guanidine, diethanolamine, choline, tromethamine.

The pharmaceutically acceptable salts of the present invention can be synthesized from the subject compound, which contains a basic or an acidic moiety, by conventional chemical methods. Generally the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, THF, dioxane or mixtures of these solvents.

The present invention furthermore includes all solvates of the compounds of the formula (1a) or (1'), more particularly of the formula (1a) or (1a') for example hydrates, and the solvates formed with other solvents of crystallization, such as alcohols, ethers, ethyl acetate, dioxane, DMF, or a lower alkyl ketone, such as acetone, or mixtures thereof.

The present invention also includes all the derivatives of the compounds of formula (1a) or (1'), more particularly of the general formula (1a) or (1a'), for example the esters, prodrugs and other physiologically acceptable derivatives.

Various polymorphs of compounds of general formula (1a) or (1'), more particularly of the general formula (1a) or (1a'), forming part of this invention may be prepared by crystallization of compounds of formula E2, (1), (1'), (1a) or (1a'), under different conditions. The different conditions are, for example, using different commonly used solvents or their mixtures for crystallization; crystallization at different temperatures; various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

With respect to the compounds of formula (1a) or (1'), more particularly to the compounds of the general formula (1a) or (1a'), the present invention also includes all stereoisomeric forms and mixtures thereof in all ratios and their pharmaceutically acceptable salts.

The present compounds are TNF-α inhibitors and find use in therapies for disorders associated with abnormal TNF-α activity, comprising: inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegener's granulomatosis, meningitis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, ankylosing spondylitis, and skin delayed-type hypersensitivity disorders, Alzheimer's disease, systemic lupus erythematosus, allergic asthma.

The present compounds are also interleukin (IL-1, IL-6, IL-8) inhibitors and find use in therapies for disorders associated with abnormal interleukin (IL-1, IL-6, IL-8) activity, comprising: rheumatoid arthritis, osteoarthritis and other autoimmune conditions.

The term "treating", "treat" or "treatment" as used herein includes preventive (prophylactic) and palliative treatment.

By "pharmaceutically acceptable" is meant that the carrier, diluent, excipients, and/or salt must be compatible with the other ingredients of the formulation, and not deleterious to the recipient thereof.

The expression "prodrug" refers to compounds that are drug precursors, which following administration, release the drug in vivo via some chemical or physiological process e.g., a prodrug on being brought to the physiological pH or through an enzyme action is converted to the desired drug form.

A primary aspect of this invention is a method for treating a mammal (e.g., a human) having a disease or condition with underlying TNF-α involvement by administering a therapeutically effective amount of a compound of the general formula (1a) or (1'), more particularly by the general formula (1a) or (1a'), or a prodrug thereof, or a pharmaceutically acceptable salt of the compound or of the prodrug to the mammal.

Another aspect of this invention is directed to a method for preventing and/or minimizing damage resulting from abnormal TNF-α activity, by administering to an affected mammal, (e.g., a female or male human), a therapeutically effective amount of a compound of the general formula (1a) or (1'), more particularly of the general formula (1a) or (1a'), or a prodrug thereof, or a pharmaceutically acceptable salt of the compound or the prodrug.

In another aspect of this invention a compound of general formula (1a) or (1a'), is administered locally.

The present invention also envisages the use of a compound of the general formula (1a) or (1'), more particularly of the general formula (1a) or (1a'), a prodrug thereof, or a pharmaceutically acceptable salt of the compound or of the prodrug in combination with other pharmaceutically active compounds. For instance, a pharmaceutical composition, comprising a compound of the general formula (1a) or (1'), more particularly of the general formula (1a) or (1a'), or a pharmaceutically acceptable salt or prodrug thereof, can be administered to a mammal, in particular a human, with any other TNF-α inhibitor or any other pharmaceutically active compound known to be useful in treating one of the above mentioned disorders, in mixtures with one another or in the form of pharmaceutical preparations.

The present invention furthermore relates to pharmaceutical compositions that contain an effective amount of at least one compound of the general formula (1a) or (1'), more particularly of the general formula (1a) or (1a'), and/or its physiologically tolerable salts and/or its prodrugs in addition to a customary pharmaceutically acceptable carrier, and to a process for the production of a pharmaceutical, which comprises bringing at least one compound of formula (1a) or (1a'), into a suitable administration form using a pharmaceutically suitable and physiologically tolerable excipient and, if appropriate, further suitable active compounds, additives or auxiliaries.

The present invention also relates to a method for the preparation of a medicament for the treatment or prevention of disorders associated with increased TNF-α activity characterized in that at least one compound of the general formula (1a) or (1'), more particularly of the general formula (1a) or (1a'), is used as the pharmaceutically active substance.

The compounds of the present invention are particularly useful as anti-inflammatory agents. The present invention accordingly relates to the use of a compound of the general formula (1a), (1'), (1a) or (1a'), where provisos (ii) and (iii) in formula (1') are not applicable, for the manufacture of a medicament for the prevention or treatment of inflammation.

The compounds of the present invention are also useful for the treatment of rheumatoid arthritis. The present invention accordingly relates to the use of a compound of the general formula (1a), (1'), (1a) or (1a'), for the manufacture of a medicament for the prevention or treatment of rheumatoid arthritis, juvenile rheumatoid arthritis, psoriatic arthritis, osteoarthritis, refractory rheumatoid arthritis, chronic non-rheumatoid arthritis, osteoporosis/bone resorption.

In the methods of treatment using the pharmaceutical compositions described above, the following are preferred administration routes, modes, etc.

The pharmaceuticals can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

The pharmaceutical preparations according to the invention are prepared in a manner known per se and familiar to one skilled in the art. Pharmaceutically acceptable inert inorganic and/or organic carriers and/or additives can be used in addition to the compound(s) of the general formula (1a), (1'), (1a) or (1a'), and/or its (their) physiologically tolerable salts and/or its (their) prodrugs. For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, preferably about 5 to 70%, most preferably from about 10 to about 30% by weight of the compounds of the formula (1a) or (1a'), and/or their physiologically tolerable salts and/or their prodrugs. The amount of the active ingredient of the formula (1a) or (1a'), and/or its physiologically tolerable salts and/or its prodrugs in the pharmaceutical preparations normally is from about 5 to 500 mg. The dose of the compounds of this invention, which is to be administered, can cover a wide range. The dose to be administered daily is to be selected to suit the desired effect. About 20 to 1,000 mg are preferably administered daily per patient. A preferred dosage is about 0.001 to 100 mg/kg/day of the compound of formula (1a) or (1a'), or a prodrug thereof. An especially preferred dosage is about 0.01 to 50 mg/kg/day of a compound of formula (1a) or (1a'), a prodrug thereof, or a pharmaceutically acceptable salt of the compound or of the prodrug. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredients of the general formula (1a), (1'), (1a) or (1a'), and/or their physiologically acceptable salts and/or prodrugs and carrier substances, the pharmaceutical preparations can contain additives such as, for example, fillers, antioxidants, dispersants, emulsifiers, defoamers, flavors, preservatives, solubilizers or colorants. They can also contain two or more compounds of the general formula (1a), (1'), (1a) or (1a'), and/or their physiologically tolerable salts and/or their prodrugs. Furthermore, in addition to at least one compound of the general formula (1a), (1'), (1a) or (1a'), and/or its physiologically tolerable salts and/or its prodrugs, the pharmaceutical preparations can also contain one or more other therapeutically or prophylactically active ingredients.

It is understood that modifications that do not substantially affect the activity of the various embodiments of this invention are included within the invention disclosed herein. Accordingly, the following examples are intended to illustrate but not to limit the present invention.

The invention is explained in detail in the examples given below and should not be construed to limit the scope of the invention:

It is understood that modifications that do not substantially affect the activity of the various embodiments of this invention are included within the invention disclosed herein. Accordingly, the following examples are intended to illustrate but not to limit the present invention.

The invention is explained in detail in the examples given below and should not be construed to limit the scope of the invention:

The following abbreviations are used herein:

| | |
|---|---|
| DMF | N,N-dimethylformamide |
| DMSO | dimethylsulfoxide |
| THF | tetrahydrofuran |
| Pet. ether | petroleum ether |
| HBr | hydrogen bromide |
| HCl | hydrochloric acid |

EXAMPLE 1

2-Amino-4-chloro-6-methyl-10,10-dioxo-10,11-dihydro-5-oxa-10lambda*6*-thia-dibenzo[a,d]cyclo-heptene-8-carboxylic acid methyl ester A solution of compound of Example 1j (38 g, 0.75 mol) in DMF (500 mL) was added to a suspension of activated Raney Ni (22 g) in DMF (50 mL) and was subjected to hydrogenation (100 psi pressure and 25° C.) for 4 h. The reaction mixture was filtered through celite bed and concentrated under vacuum. Chloroform (400 mL) was added to the residue with stirring. The crystalline solid obtained was filtered and washed with chloroform, dried to obtain the title compound. Yield: 29 g, (92.45%); mp: 258-260° C.; $^1$H NMR (DMSO-d$_6$, 300 MHz): δ 2.60 (s, 3H, CH$_3$), 3.85 (s, 3H, OCH$_3$), 5.07 (s, 2H, CH$_2$), 5.64 (s, 2H, NH$_2$), 6.61 (d, 2H, Ar), 8.06 (s, 1H, Ar), 8.12 (s, 1H, Ar); MS: m/e (ES+) 368 (M+1); analysis: C$_{16}$H$_{14}$ClNO$_5$S requires C, 52.25; H, 3.84; N, 3.81; Cl, 9.64; S, 8.72. found: C, 52.37; H, 3.75; N, 3.26; Cl, 9.87; S, 8.95%.

EXAMPLE 1a

4-Amino-3-methyl-benzoic acid

To a solution of 3-methyl-4-nitro-benzoic acid (100 g, 0.55 mol) in DMF (500 mL), suspension of activated Raney Ni (50 g) in DMF (50 mL) was added and was subjected to hydrogenation (200 psi pressure and 25° C.) for 6 h. The reaction mixture was filtered through celite bed and was concentrated to one third of the total volume. The reaction mixture was poured into water (1300 mL) with stirring. The solid was filtered, washed with water and dried to obtain the title compound. Yield: 70 g (84%); $^1$H NMR (DMSO-d$_6$, 300 MHz): δ 2.03 (s, 3H, CH$_3$), 5.60 (s, 2H, NH$_2$), 6.56 (d, 1H, Ar), 7.46 (d, 1H, Ar), 7.49 (s, 1H, Ar); MS: m/e (ES−) 150 (M−1).

EXAMPLE 1b

4-Bromo-3-methyl-benzoic acid

A suspension of compound of Example 1a (73 g, 0.483 mol) in water (411 mL) and 47% HBr (486 mL) was stirred at 25° C. for 1 h and then the reaction mixture was cooled to −2° C. A solution of sodium nitrate (32 g, 0.463 mol) in water (100 mL) was added to the reaction mixture over a period of 15 min, maintaining the temperature at −1° C. to −2° C. The reaction mixture was stirred at −1° C. to −2° C. for 1.5 h. The reaction mixture was added slowly to a suspension of copper (I)bromide (73 g, 0.508 mol) in water (73 mL) and aqueous HBr (73 mL). The reaction mixture was stirred at 25° C. for 1 h and then digested at 70° C. for 1 h. The solid was filtered, washed with water till the pH of the filtrate was 7 and dried to obtain the title compound. Yield: 94 g (90%); $^1$H NMR (DMSO-d$_6$, 300 MHz): δ 2.37 (s, 3H, CH$_3$), 7.64 (m, 2H, Ar), 7.87 (s, 1H, Ar); MS: m/e (ES−) 214 (M−1).

EXAMPLE 1c

4-Bromo-3-chlorosulfonyl-5-methyl-benzoic acid

Chlorosulfonic acid (150 mL, 2.18 mol) was added slowly to compound of Example 1b (74 g, 0.344 mol) at 0° C. The reaction mixture was refluxed for 4.5 h and then was poured into ice-cold water (1500 mL) with stirring. The solid was filtered, washed with water till filtrate was neutral and dried to obtain the title compound. Yield: 72.40 g (66.8%); $^1$H NMR (DMSO-d$_6$, 300 MHz): δ 2.40 (s, 3H, CH$_3$), 7.80 (s, 1H, Ar), 8.30 (s, 1H, Ar); MS: m/e (ES−) 315 (M−1).

EXAMPLE 1d

Dimer of 4-Bromo-3-mercapto-5-methyl-benzoic acid

A solution of stannous chloride (196 g, 0.86 mol) in concentrated hydrochloric acid (250 mL) and water (55 mL) was added to a stirred suspension of compound of Example 1c (68 g, 0.217 mol) in acetic acid (580 mL) at 80° C., over a period of 20 min. The reaction mixture was stirred at 80° C. for 4 h. The reaction mixture was cooled, poured into water (500 mL) with stirring and digested at 80° C. for 30 min. The solid was filtered, washed with water till filtrate was neutral and dried to obtain the title compound. Yield: 48 g (90%); $^1$H NMR (DMSO-d$_6$, 300 MHz): δ 2.40 (s, 3H, CH$_3$), 7.70 (s, 1H, Ar), 7.84 (s, 1H, Ar); MS: m/e (ES−) 491 (M−1).

EXAMPLE 1e

Dimer of 4-bromo-3-mercapto-5-methyl-benzoic acid methyl ester

Thionyl chloride (130 mL, 1.82 mol) was added slowly to the compound of Example 1d (48 g, 0.198 mol) at 0° C. The reaction mixture was refluxed for 18 h. Excess thionyl chloride was distilled out from the reaction mixture. The reaction mixture was cooled to 0° C. and methanol (200 mL) was added slowly over a period of 15 min. The reaction mixture was refluxed for 1 h. Methanol was removed from the reaction mixture under reduced pressure, and water (500 mL) was added and stirred for 15 min. The solid precipitated was filtered, washed with water and dried to obtain the title compound. Yield: 47 g (93%); $^1$H NMR (DMSO-d$_6$, 300 MHz): δ 2.42 (s, 3H, CH$_3$), 3.77 (s, 3H, OCH$_3$), 7.78 (s, 1H, Ar), 7.89 (s, 1H, Ar); MS: m/e (EI) 520 (M+).

EXAMPLE 1f

4-Bromo-3-mercapto-5-methyl-benzoic acid methyl ester

Triphenyl phosphine (34 g, 0.126 mol) was added to a suspension of compound of Example 1e (47 g, 0.09 mol) in methanol (1000 mL) and water (300 mL). The reaction mixture was stirred at 25° C. for 2 h. Methanol was removed under reduced pressure, water (500 mL) was added and extracted using ethyl acetate (3×300 mL). The combined organic layer was washed with water (300 mL), brine (200 mL), dried and purified by column chromatography (silica gel, 1% ethyl acetate in pet. ether 60-80° C.) to obtain the title compound. Yield: 43 g (92%); $^1$H NMR (CDCl$_3$, 300 MHz): δ 2.44 (s, 3H, CH$_3$), 3.89 (s, 3H, OCH$_3$), 4.07 (s, 1H, SH), 7.63 (s, 1H, Ar), 7.84 (s, 1H, Ar); MS: m/e (ES−) 260 (M−1).

EXAMPLE 1g

4-Bromo-3-[2-(tert-butyl-dimethyl-silanyloxy)-3-chloro-benzylsulfanyl]-5-methyl-benzoic acid methyl ester Triethyl amine (36 mL, 0.263 mol) was added to a solution of (2-bromomethyl-6-chloro-phenoxy)-tert-butyl-dimethyl-silane (72 g, 0.214 mol) [prepared from 6-chloro cresol by protecting the hydroxy group with t-butyldimethylsilane followed by bromination using N-bromosuccinimide] and compound of Example 1f (43 g, 0.164 mol) in chloroform (600 mL) at 5° C. over a period of 20 min. The reaction mixture was stirred at 25° C. for 30 min. The reaction mixture was washed with water (2×200 mL) and brine (100 mL). The solvent was removed under reduced pressure and to the oily mass obtained, methanol (300 mL) was added with stirring. The crystalline solid obtained was filtered, washed with methanol and dried to obtain the title compound. Yield: 70 g, (83%); $^1$H NMR (CDCl$_3$, 300 MHz): δ 0.28 (s, 6H, 2CH$_3$), 1.03 (s, 9H, 3CH$_3$), 2.45 (s, 3H, CH$_3$), 3.89 (s, 3H, OCH$_3$), 4.19 (s, 2H, CH$_2$), 6.89 (t, 1H, Ar), 7.24 (t, 1H, Ar), 7.32 (d, 1H, Ar), 7.61 (s, 1H, Ar), 7.69 (s, 1H, Ar); MS: m/e (ES−) 515 (M−1).

EXAMPLE 1h

4-Bromo-3-[2-(tert-butyl-dimethyl-silanyloxy)-3-chloro-phenyl methane sulfonyl]-5-methyl-benzoic acid methyl ester m-Chlorobenzoic acid (127 g, 0.33 mol) was added in three portions at an interval of 10 min to a solution of compound of Example 1g (70 g, 0.135 mol) in dichloromethane (700 mL) at 15° C. and stirred further at 25° C. for 16 h. The reaction mixture was filtered. The solvent was removed from the filtrate under reduced pressure and the residue was stirred in saturated bicarbonate solution (2×200 mL). The solid was filtered, washed with water and dried to obtain the title compound. Yield: 72.8 g (97%); $^1$H NMR (CDCl$_3$, 300 MHz): δ 0.22 (s, 6H, 2CH$_3$), 0.99 (s, 9H, 3CH$_3$), 2.56 (s, 3H, CH$_3$), 3.89 (s, 3H, OCH$_3$), 4.75 (s, 2H, CH$_2$), 6.81 (t, 1H, Ar), 7.13 (d, 1H, Ar), 7.26 (d, 1H, Ar), 8.11 (s, 1H, Ar), 8.29 (s, 1H, Ar); MS: m/e (CI) 549 (M+1).

EXAMPLE 1i

4-Chloro-6-methyl-10,10-dioxo-10,11-dihydro-5-oxa-10lambda*6*-thia-dibenzo[a,d]cycloheptene-8-carboxylic acid methyl ester A solution of tetrabutyl ammonium fluoride (90 g, 0.283 mol) in tetrahydrofuran (250 mL) was added dropwise to a solution of compound of Example 1h (72 g, 0.135 mol) in tetrahydrofuran (350 mL) over a period of 25 min under nitrogen, at 5° C. The reaction mixture was stirred at 5° C. for 30 min. Solvent was removed under reduced pressure and water (250 mL) was added. The solid was filtered and washed with water (2000 mL). The crude product was purified by column chromatography (silica gel, methanol in chloroform) to obtain the title compound. Yield: 37.0 g (87%); $^1$H NMR (CDCl$_3$, 300 MHz): δ 2.71 (s, 3H, CH$_3$), 3.91 (s, 3H, OCH$_3$), 4.72 (s, 2H, CH$_2$), 7.25 (d, 1H, Ar), 7.33 (d, 1H, Ar), 7.45 (d, 1H, Ar), 8.09 (s, 1H, Ar), 8.46 (s, 1H, Ar); MS: m/e (EI) 352 (M+).

EXAMPLE 1j

4-Chloro-6-methyl-2-nitro-10,10-dioxo-10,11-dihydro-5-oxa-10lambda*6*-thia-dibenzo[a,d]cycloheptene-8-carboxylic acid methyl ester Concentrated sulfuric acid (240 mL, 4.2 mol) was added to a solution of compound of Example 1I (37 g, 0.105 mol) in concentrated nitric acid (1100 mL, 17.34 mol) at 5° C. The reaction mixture was stirred at 5° C. for 25 min, and then at 40° C. for 4.5 h. Reaction mixture was quenched into ice water (2500 mL), the solid precipitated was filtered, washed with water till filtrate was neutral to pH and dried to obtain the title compound. Yield: 38 g (90.91%); $^1$H NMR (CDCl$_3$, 300 MHz): δ 2.7 (s, 3H, CH$_3$), 3.90 (s, 3H, OCH$_3$), 4.79 (s, 2H, CH$_2$), 8.10 (s, 1H, Ar), 8.22 (s, 1H, Ar), 8.38 (s, 1H, Ar), 8.48 (s, 1H, Ar); MS: m/e (ES-) 396 (M-1).

EXAMPLE 2

2-Amino-4-chloro-6-methyl-10,10-dioxo-10,11-dihydro-5-oxa-10lambda*6*-thia-dibenzo[a,d]cycloheptene-8-carboxylic acid A solution of sodium hydroxide (0.32 g, 7.13 mmol) in water (5 mL) was added to a solution of Example 1 (1 g, 2.71 mmol) in methanol (30 mL). The reaction mixture was stirred at 60° C. for 1.5 h, the solvent was removed under vacuum and water (20 mL) was added. The reaction mixture was acidified to pH 3 using 10% aqueous hydrochloric acid. The precipitate was filtered and washed with water, dried to obtain the title compound. Yield: 0.85 g, (89%); $^1$H NMR (DMSO-d$_6$, 300 MHz): δ 2.61 (s, 3H, CH$_3$), 5.66 (s, 2H, CH$_2$), 6.64 (d, 2H, Ar), 8.03 (s, 1H, Ar), 8.12 (s, 1H, Ar); MS: m/e (ES-) 352 (M-1).

EXAMPLE 3

2-Amino-4-chloro-6-methyl-10,10-dioxo-10,11-dihydro-5-oxa-10lambda*6*-thia-dibenzo[a,d]cycloheptene-8-carboxylic acid sodium salt A solution of sodium hydroxide (0.018 g, 0.47 mmol) in water (0.2 mL) was added to a solution of Example 2 (0.167 g, 0.47 mmol) in methanol (5 mL) and stirred at 25° C. for 15 min. The solvent was removed under vacuum, and dried to obtain the title compound. Yield: 0.16 g, (91%); $^1$H NMR (DMSO-d$_6$, 300 MHz): δ 2.55 (s, 3H, CH$_3$), 4.92 (s, 2H, CH$_2$), 5.57 (s, 2H, NH$_2$), 6.60 (m, 2H, Ar), 7.90 (s, 1H, Ar), 8.10 (s, 1H, Ar); MS: m/e (ES-) 352 (M-Na); analysis: C$_{15}$H$_{11}$ClNNaO$_5$S.2H$_2$O requires C, 43.75; H, 3.67; N, 3.40; Cl, 8.61; S, 7.79. found: C, 44.20; H, 3.34; N, 3.49; Cl, 9.25; S, 8.36%.

EXAMPLE 4

4-Chloro-2-(2-chloro-acetylamino)-6-methyl-10,10-dioxo-10,11-dihydro-5-oxa-10lambda*6*-thia-dibenzo[a,d]cycloheptene-8-carboxylic acid methyl ester Chloroacetylchloride (3.3 mL, 40.8 mmol) was added to the solution of compound of Example 1 (5 g, 13.6 mmol) in dichloromethane (100 mL) at 20° C. Pyridine (6.6 mL, 81.6 mmol) was added and the reaction mixture was stirred for 2 h. The solvent was removed under vacuum and water (200 mL) was added. The solid obtained was filtered, washed with water and purified by stirring in ethyl acetate (200 mL) at reflux condition for 30 min. The solid was filtered and dried to obtain the title compound. Yield: 4.86 g (80.1%); mp 292-293° C.; $^1$H NMR (DMSO-d$_6$, 300 MHz): δ 2.64 (s, 3H, CH$_3$), 3.86 (s, 3H, OCH$_3$), 4.27 (s, 2H, CH$_2$), 5.34 (s, 2H, CH$_2$), 7.67 (s, 1H, Ar), 7.88 (s, 1H, Ar), 8.11 (s, 1H, Ar), 8.15 (s, 1H, Ar), 10.70 (s, 1H, NH); MS: m/e (ES+) 445 (M+1); analysis: C$_{18}$H$_{15}$Cl$_2$NO$_6$S requires C, 48.66; H, 3.40; N, 3.15; Cl, 15.96; S, 7.22. found: C, 48.09; H, 3.37; N, 3.38; Cl, 16.37; S, 7.72%.

EXAMPLE 5

4-Chloro-2-(2-hydroxy-acetylamino)-6-methyl-10,10-dioxo-10,11-dihydro-5-oxa-10lambda*6*-thia-dibenzo[a,d]cycloheptene-8-carboxylic acid methyl ester (A)

2-(2-Acetoxy-acetylamino)-4-chloro-6-methyl-10,10-dioxo-10,11-dihydro-5-oxa-10lambda*6*-thia-dibenzo[a,d]cycloheptene-8-carboxylic acid methyl ester (B) Sodium acetate (0.054 g, 0.658 mmol) in water (5 mL) was added to solution of compound of Example 4 (0.18 g, 0.405 mmol) in DMF (5 mL) at 25° C. and then the reaction mixture was stirred at 80° C. for 6 h. The solvent was removed under vacuum, water (15 mL) was added and extracted using ethyl acetate (3×30 mL). Combined organic layer was washed with water (2×100 mL), brine (100 mL) and dried over anhydrous sodium sulfate. The solvent was removed under vacuum and crude product was purified by column chromatography (silica gel) to obtain the title compound (B) (1% methanol in chloroform) and compound (A) (2% methanol in chloroform).

Compound (A): Yield: 0.05 g; mp 276-278° C.; $^1$H NMR (DMSO-d$_6$, 300 MHz): δ 2.65 (s, 3H, CH$_3$), 3.68 (s, 3H, OCH$_3$), 4.0 (d, 2H, CH$_2$), 5.28 (s, 2H, CH$_2$), 5.68 (t, 1H, OH), 7.90 (s, 1H, Ar), 7.96 (s, 1H, Ar), 8.11 (s, 1H, Ar), 8.15 (s, 1H, Ar), 10.08 (s, 1H, NH); MS: m/e (ES−) 424 (M−1); analysis: C$_{18}$H$_{16}$ClNO$_7$S requires C, 50.77; H, 3.79; N, 3.29; Cl, 8.33; S, 7.53. found: C, 49.86; H, 3.80; N, 3.23; Cl, 8.72; S, 7.12%.

Compound (B): Yield: 0.030 g; mp: 180-182° C.; $^1$H NMR (DMSO-d$_6$, 300 MHz): δ 2.09 (s, 3H, CH$_3$), 2.63 (s, 3H, CH$_3$), 3.84 (s, 3H, OCH$_3$), 4.64 (s, 2H, CH$_2$), 5.29 (s, 2H, CH$_2$), 7.67 (d, 1H, Ar), 7.83 (s, 1H, Ar), 8.09 (d 1H, Ar), 8.14 (d, 1H, Ar); MS: m/e (ES+) 468 (M+1); analysis: C$_{20}$H$_{18}$ClNO$_8$S requires C, 51.34; H, 3.88; N, 2.99; Cl, 7.58; S, 6.85. found: C, 49.30; H, 3.79; N, 2.80; Cl, 7.63; S, 6.40%.

EXAMPLE 6

4-Chloro-6-methyl-10,10-dioxo-2-propionylamino-10,11-dihydro-5-oxa-10lambda*6*-thia-dibenzo[a,d]cycloheptene-8-carboxylic acid methyl ester A solution of oxalyl chloride (0.17 mL, 2.03 mmol) and propionic acid (0.15 mL, 2.03 mmol) in dichloromethane (20 mL) was stirred for 1 h. Compound of Example 1 (0.5 g, 1.35 mmol) in DMF (5 mL) was added to the reaction mixture at 25° C. and stirred for 18 h. The solvent was removed under vacuum, water (25 mL) was added and the solid precipitated was filtered. The crude product was purified by column chromatography (silica gel, 1% methanol in chloroform) to obtain the title compound. Yield: 0.28 g, (60%); mp: 226-228° C.; $^1$H NMR (DMSO-d$_6$, 300 MHz): δ 1.06 (t, 3H, CH$_3$), 2.33 (q, 2H, CH$_2$), 2.64 (s, 3H, CH$_3$), 3.85 (s, 3H, OCH$_3$), 5.30 (s, 2H, CH$_2$), 7.66 (d, 1H, Ar), 7.88 (s, 1H, Ar), 8.10 (s, 1H, Ar), 8.15 (s, 1H, Ar), 10.26 (s, 1H, NH); MS: m/e (EI) 423 (M+); analysis: C$_{19}$H$_{18}$ClNO$_6$S requires C, 53.66; H, 4.28; N, 3.30; Cl, 8.32; S, 7.56. found: C, 53.38; H, 4.27; N, 3.48; Cl, 8.64; S, 7.75%.

EXAMPLE 7

4-Chloro-2-formylamino-6-methyl-10,10-dioxo-10,11-dihydro-5-oxa-10lambda*6*-thia-dibenzo[a,d]cycloheptene-8-carboxylic acid Sodium formate (0.308 g, 4.58 mmol) was added to a solution of compound of Example 2 (0.8 g, 2.26 mmol) in formic acid 85% (8 mL) and refluxed for 2 h. The reaction mixture was diluted using water (20 mL) and the solid obtained was filtered, washed with water and dried. The product was purified by crystalisation using DMF/methanol to obtain the title compound. Yield: 0.78 g, (91%); $^1$H NMR (DMSO-d$_6$, 300 MHz): δ 2.64 (s, 3H, CH$_3$), 5.31 (s, 2H, CH$_2$), 7.70 (s, 1H, Ar), 7.87 (s, 1H, Ar), 7.93 (s, 1H, Ar), 8.08 (s, 1H, Ar), 8.31 (s, 1H, CHO), 10.57 (s, 1H, NH); MS: m/e (ES−) 380 (M−1);

EXAMPLE 8

4-Chloro-2-formylamino-6-methyl-10,10-dioxo-10,11-dihydro-5-oxa-10lambda*6*-thia-dibenzo[a,d]cycloheptene-8-carboxylic acid sodium salt A solution of sodium hydroxide (0.0108 g, 0.27 mmol) in water (0.1 mL) was added to the solution of Example 7 (0.104 g, 0.27 mmol) in methanol (5 mL) and stirred at 25° C. for 15 min, the solvent was removed and dried to obtain the title compound. Yield: 0.11 g, (100%); $^1$H NMR (DMSO-d$_6$, 300 MHz): δ 2.58 (s, 3H, CH$_3$), 5.16 (s, 2H, CH$_2$), 7.69 (d, 1H, Ar), 7.87 (d, 1H, Ar), 7.95 (s, 1H, Ar), 8.11 (s, 1H, Ar), 8.30 (s, 1H, CHO), 10.78 (s, 1H, NH); MS: m/e (ES−) 380 (M-Na); analysis: C$_{16}$H$_{11}$ClNNaO$_6$S.2H$_2$O requires C, 43.70; H, 3.44; N, 3.81; Cl, 8.06; S, 7.29. found: C, 42.88; H, 3.19; N, 3.04; Cl, 8.69; S, 7.67%.

EXAMPLE 9

4-Chloro-2-formylamino-6-methyl-10,10-dioxo-10,11-dihydro-5-oxa-10lambda*6*-thia-dibenzo[a,d]cycloheptene-8-carboxylic acid methyl ester Sodium formate (7.29 g, 0.108 mol) was added to a suspension of compound of Example 1 (20 g, 0.054 mol) in formic acid (200 mL) and refluxed for 1.5 h. The reaction mixture was cooled and poured into ice water (800 mL). The solid precipitated was filtered, washed with water and dried. The crude product was purified by column chromatography (silica gel, 1% methanol in chloroform) to obtain the title compound. Yield: 18 g, (83%); mp 258-262° C. (decomposed); $^1$H NMR (DMSO-d$_6$, 300 MHz): δ 2.64 (s, 3H, CH$_3$), 3.86 (s, 3H, OCH$_3$), 5.25 (s, 2H, CH$_2$, trans minor isomer), 5.33 (s, 2H, CH$_2$, cis major isomer), 7.33 (d, 1H, Ar, trans minor isomer), 7.50 (d, 1H, Ar, trans minor isomer), 7.69 (d, 1H, Ar, cis major isomer), 7.86 (d, 1H, Ar, cis major isomer), 8.10 (s, 1H, Ar), 8.15 (s, 1H, Ar), 8.30 (s, 1H, CHO, cis major isomer), 8.80 (d, 1H, CHO, trans minor isomer), 10.40 (d, 1H, NH, trans minor isomer), 10.57 (s, 1H, NH, cis major isomer); MS: m/e (ES−) 394 (M−1); analysis: C$_{17}$H$_{14}$ClNO$_6$S requires C, 51.54; H, 3.56; N, 3.54; Cl, 8.96; S, 8.10. found: C, 51.96; H, 3.63; N, 3.60; Cl, 9.43; S, 8.50%.

EXAMPLE 10

4-Chloro-2-formylamino-6-methyl-10,10-dioxo-10,11-dihydro-5-oxa-10lambda*6*-thia-dibenzo[a,d]cycloheptene-8-carboxylic acid ethyl ester Sodium formate (0.075 g, 1.1 mmol) was added to a suspension of 2-amino-4-chloro-6-methyl-10,10-dioxo-10,11-dihydro-5-oxa-10lambda*6*-thia-dibenzo[a,d]cycloheptene-8-carboxylic acid ethyl ester (0.420 g, 1.1 mmol) [prepared by hydrolysis of compound of Example 1 and followed by esterification with ethanol/H$_2$SO$_4$] in formic acid (25 mL) and refluxed for 1.5 h. The reaction mixture was cooled and poured into ice water (100 mL). The solid precipitated was filtered, washed with water and dried. The crude product was purified by column chromatography (silica gel, 1% methanol in chloroform) to obtain the title compound. Yield: 0.21 g (47%); mp 202-204° C.; $^1$H NMR (DMSO-d$_6$, 300 MHz): δ 1.31 (t, 3H, OCH$_2$CH$_3$), 2.64 (s, 3H, CH$_3$), 4.31 (q, 2H, OCH$_2$CH$_3$), 5.25 (s, 2H, CH$_2$, trans minor isomer), 5.33 (s, 2H, CH$_2$, cis major isomer), 7.34 (d, 1H, Ar, trans minor isomer), 7.50 (d, 1H, Ar, trans minor isomer), 7.69 (d, 1H, Ar, cis major isomer), 7.86 (d, 1H, Ar, cis major isomer), 8.10 (s, 1H, Ar), 8.15 (s, 1H, Ar), 8.31 (s, 1H, CHO, cis major isomer), 8.80 (d, 1H, CHO, trans minor isomer), 10.43 (d, 1H, NH, trans minor isomer), 10.57 (s, 1H, NH, cis major isomer); MS: m/e (ES−) 408 (M−1); analysis: $C_{18}H_{16}ClNO_6S$ requires C, 52.75; H, 3.93; N, 3.42; Cl, 8.65; S, 7.82. found: C, 52.47; H, 3.86; N, 3.36; Cl, 8.81; S, 7.67%.

EXAMPLE 11

4-Chloro-2-formylamino-6-methyl-10,10-dioxo-10,11-dihydro-5-oxa-10lambda*6*-thia-dibenzo[a,d]cycloheptene-8-carboxylic acid isopropyl ester Sodium formate (0.040 g, 0.581 mmol) was added to a suspension of 2-amino-4-chloro-6-methyl-10,10-dioxo-10,11-dihydro-5-oxa-10lambda*6*-thia-dibenzo[a,d]cycloheptene-8-carboxylic acid isopropyl ester (0.23 g, 0.581 mmol) [prepared by hydrolysis of compound of Example 1 and followed by esterification using isopropanol/$H_2SO_4$] in formic acid (20 mL) and refluxed for 1.5 h. The reaction mixture was cooled and poured into ice water (100 mL). The solid precipitated was filtered, washed with water and dried. The crude product was crystallised with ethylacetate/pet. ether 60-80° C. to obtain the title compound. Yield: 0.12 g (48%); mp: 212-215° C.; $^1$H NMR (DMSO-$d_6$, 300 MHz): δ 1.30 (d, 6H, OCH(CH$_3$)$_2$, 2.64 (s, 3H, CH$_3$), 5.12 (m, 1H, OCH(CH$_3$)$_2$), 5.25 (s, 2H, CH$_2$, trans minor isomer), 5.32 (s, 2H, CH$_2$, cis major isomer), 7.33 (d, 1H, Ar, trans minor isomer), 7.50 (d, 1H, Ar, trans minor isomer), 7.69 (d, 1H, Ar, cis major isomer), 7.86 (d, 1H, Ar, cis major isomer), 8.10 (s, 1H, Ar), 8.15 (s, 1H, Ar), 8.30 (s, 1H, CHO, cis major isomer), 8.80 (d, 1H, CHO, trans minor isomer), 10.40 (d, 1H, NH, trans minor isomer), 10.57 (s, 1H, NH, cis major isomer); MS: m/e (ES−) 422 (M−1); analysis: $C_{19}H_{18}ClNO_6S$ requires C, 53.84; H, 4.28; N, 3.30; Cl, 8.36; S, 7.56. found: C, 54.27; H, 4.45; N, 2.94; Cl, 8.76; S, 7.77%.

EXAMPLE 12

2-[Bis-(2-chloro-ethyl)amino]-4-chloro-6-methyl10,10-dioxo-10,11-dihydro-5-oxa-10lambda*6*-thia-dibenzo[a,d]-cycloheptene-8-carboxylic acid methyl ester Sodium borohydride (2.90 g, 0.072 mol) was portionwise added to a stirred solution of chloroacetic acid (12.08 g, 0.12 mol) in benzene (300 mL) and dry tetrahydrofuran (30 mL) under nitrogen atmosphere at 10° C. The reaction mixture was stirred for 1 h till no further evolution of hydrogen gas was observed. Compound of Example 1 (4.7 g, 0.012 mol) was added to the reaction mixture and the mixture was refluxed for 3 h. 10% sodium bicarbonate solution (100 mL) was added to the reaction mixture and extracted with ethyl acetate (3×100 mL). Combined organic layer was washed with water (2×100 mL), brine (100 mL) and dried over anhydrous sodium sulfate. Solvent was removed under vacuum and the crude product obtained was crystallized using ethyl acetate/hexane to obtain the title compound. Yield: 3.30 g (52%); mp: 190-191° C.; $^1$H NMR (CDCl$_3$, 300 MHz): δ 2.80 (s, 3H, CH$_3$), 3.82 (s, 8H, 4CH$_2$), 3.90 (s, 3H, OCH$_3$), 5.20 (s, 2H, CH$_2$), 6.90 (d, 1H, Ar), 7.10 (d, 1H, Ar), 8.1 (s, 1H, Ar), 8.45 (s, 1H, Ar); MS: m/e (ES+) 492 (M+1); analysis: $C_{20}H_{20}Cl_3NO_5S$ requires C, 48.75; H, 4.09; N, 2.84; Cl, 21.58; S, 6.51. found: C, 48.75; H, 3.93; N, 2.58; Cl, 21.85; S, 6.73%.

EXAMPLE 13

2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carboxylic acid methyl ester Ethylene oxide (120 mL) was added to a stirred solution of compound of Example 1 (4.5 g, 12.26 mmol) in acetic acid (50 mL), water (50 mL) and THF (20 mL) mixture at −70° C., over a period of 1 h and then stirred at 25° C. for 14 h. The reaction mixture was cooled; pH was adjusted to 7 using 10% aqueous solution of sodium bicarbonate. The reaction mixture was extracted with ethyl acetate (3×250 mL). Combined organic layer was washed with brine (2×100 mL) and dried over sodium sulphate. Solvent was removed and the resulting crude product was purified by column chromatography (silica gel, ethyl acetate/pet ether) to obtain the title compound. Yield: 4 g (72%); mp 199-201° C.; $^1$H NMR (DMSO-$d_6$, 300 MHz): δ 2.62 (s, 3H, CH$_3$), 3.40 (t, 4H, 2CH$_2$), 3.51 (t, 4H, 2CH$_2$), 3.85 (s, 3H, OCH$_3$), 4.80 (t, 2H, 2OH), 5.11 (s, 2H, CH$_2$), 6.76 (s, 1H, Ar), 6.83 (s, 1H, Ar), 8.06 (s, 1H, Ar), 8.13 (s, 1H, Ar); MS: m/e (ES+) 456 (M+1).

EXAMPLE 14

4-Chloro-6-methyl-2-piperazin-1-yl-11H-5-oxa-10-thia-dibenzo[a,d]cycloheptene-8-carboxylic acid methyl ester hydrochloride (Compound A)

EXAMPLE 15

4-Chloro-6-methyl-10-oxo-2-piperazin-1-yl-10,11-dihydro-5-oxa-10lambda*4*-thia-dibenzo[a,d]cycloheptene-8-carboxylic acid methyl ester hydrochloride (Compound B)

Aqueous ammonia solution (25%, 30 mL) was added to 2-[bis-(2-chloroethyl)-amino]-4-chloro-6-methyl-10-oxo-10,11-dihydro-5-oxa-10lambda*4*-thia-dibenzo[a,d]-cycloheptene-8-carboxylic acid (3.2 g, 6.9 mmol) [prepared by alkaline hydrolysis of compound of Example 15e] in methanol (120 mL). The reaction mixture was sealed under nitrogen atmosphere, kept at 110° C. for 9 h, cooled and the seal was opened. The reaction mixture was concentrated to remove solvent and ammonia, and azeotroped with toluene once. The product was taken in methanolic HCl solution (45 mL) and stirred at 90° C. for 4 h. The reaction mixture was cooled. The solid separated was filtered, washed with methanol and dried under vacuum to obtain the crude product. The crude product was dissolved in chloroform and treated with aqueous sodium carbonate to obtain the freebase, which was purified by column chromatography (silica gel, 5% methanol in chloroform) to obtain free base of compound A (yield: 0.3 g) and free base of compound B (yield: 0.25 g).

Free base of compound A and free base of compound B were converted to the hydrochloride salt using methanolic HCl to obtain title compound A (Example 14) and title compound B (Example 15).

Compound A

Mp: 256-259° C.; $^1$H NMR (DMSO-$d_6$, 300 MHz): δ 2.53 (s, 3H, CH$_3$), 3.14 (s, 4H, 2CH$_2$), 3.40 (s, 4H, 2CH$_2$), 3.78 (s,

3H, OCH$_3$), 4.32 (s, 2H, CH$_2$), 7.02 (s, 2H, Ar), 7.57 (s, 1H, Ar), 7.58 (s, 1H, Ar) and 9.18 (s, 2H, NH & HCl); MS: m/e (ES+) 405 (M+1, free base).

Compound B

Mp: >320° C.; $^1$H NMR (DMSO-d$_6$, 300 MHz): δ 2.58 (s, 3H, CH$_3$), 3.19 (s, 4H, 2CH$_2$), 3.42 (s, 4H, 2CH$_2$), 3.89 (s, 3H, OCH$_3$), 4.73 (d, 2H, CH$_2$), 7.16 (s, 2H, Ar), 8.01 (s, 1H, Ar), 8.12 (s, 1H, Ar) and 9.18 (s, 2H, NH & HCl); MS: m/e (ES+) 421 (M+1, free base).

EXAMPLE 15a

4-Bromo-3-(3-chloro-2-hydroxy-benzylsulfanyl)-5-methyl-benzoic acid methyl ester The solution of tetrabutyl ammonium fluoride (42.8 g, 0.13 mol) in THF (350 mL) was added dropwise to a solution of compound of Example 1 g (35 g, 0.068 mol) in THF (150 mL) under nitrogen at 5° C. and stirred for 30 min. Solvent was removed from the reaction mixture and ice water (200 mL) was added. The solid separated was filtered, and washed with water (3×100 ml). The crude obtained was purified by column chromatography (silica gel, ethyl acetate/pet. ether) to obtain the title compound. Yield: 24 g, (88%); $^1$H NMR (CDCl$_3$, 300 MHz): δ 2.44 (s, 3H, CH$_3$), 3.87 (s, 3H, OCH$_3$), 4.26 (s, 2H, CH$_2$), 6.81 (t, 1H, Ar), 7.20-7.26 (m, 2H, Ar), 6.81 (t, 1H, Ar), 7.70 (s, 1H, Ar); MS: m/e (EI) 401 (M+).

EXAMPLE 15b

4-Chloro-6-methyl-11H-5-oxa-10-thia-dibenzo[a,d]cycloheptene-8-carboxylic acid methyl ester Sodium hydride (1.65 g, 0.068 mol) was added portionwise to a solution of compound of Example 15a (23 g, 0.057 mol) in DMF (600 mL) and stirred at 80° C. for 10 h. The solvent was removed, and chloroform (300 mL) was added. The organic layer was washed with 10% HCl (2×80 mL), followed by water (100 mL), and brine and dried over anhydrous sodium sulphate. The solvent was removed and the crude product obtained was purified by column chromatography (silica gel, ethyl acetate/pet ether) to obtain the title compound. Yield: 9 g, (49%); $^1$H NMR (CDCl$_3$, 300 MHz): δ 2.50 (s, 3H, CH$_3$), 3.91 (s, 3H, OCH$_3$), 4.21 (s, 2H, CH$_2$), 7.05 (m, 2H, Ar), 7.28 (d, 1H, Ar), 7.60 (d, 2H, Ar); MS: m/e (EI) 320 (M+).

EXAMPLE 15c

4-Chloro-6-methyl-2-nitro-10-oxo-10,11-dihydro-5-oxa-10lambda*4*-thia-dibenzo[a,d]cycloheptene-8-carboxylic acid methyl ester Compound of Example 15b (4.1 g, 12.8 mmol) was added to solution of nitrating mixture (nitric acid 200 mL and sulfuric acid 20 mL) at 0° C. and stirred for 18 h. The reaction mixture was poured slowly with stirring into ice water (200 mL). The solid separated was filtered, washed with water and dried to obtain the title compound. Yield: 2.5 g, (52%); $^1$H NMR (CDCl$_3$, 300 MHz): δ 2.65 (s, 3H, CH$_3$), 3.93 (s, 3H, OCH$_3$), 4.57 (s, 2H, CH$_2$), 8.16 (d, 2H, Ar), 8.35 (d, 2H, Ar); MS: m/e (ES−) 380 (M−1).

EXAMPLE 15d

2-Amino-4-chloro-6-methyl-10-oxo-10,11-dihydro-5-oxa-10lambda*4*-thia-dibenzo[a,d]cycloheptene-8-carboxylic acid methyl ester The solution of compound of Example 15c (3.7 g, 9.7 mmol) in DMF (100 mL) was added to a suspension of activated Raney Nickel (3.7 g) in DMF (10 mL) and was subjected to hydrogenation at 50 psi pressure at 25° C. for 6 h. The reaction mixture was filtered using celite bed and the solvent was removed. The crude product obtained was purified by column chromatography (silica gel, methanol/chloroform) to obtain the title compound. Yield: 2.5 g, (74%); $^1$H NMR (DMSO-d$_6$, 300 MHz): δ 2.56 (s, 3H, CH$_3$), 3.84 (s, 3H, OCH$_3$), 4.61 (q, 2H, CH$_2$), 5.5 (s, 2H, NH$_2$), 6.61 (s, 2H, Ar), 7.97 (s, 1H, Ar); MS: m/e (EI) 351 (M+).

EXAMPLE 15e

2-[Bis-(2-chloroethyl)amino]-4-chloro-6-methyl-10-oxo-10,11-dihydro-5-oxa-10lambda*4*thia-dibenzo[a,d]-cycloheptene-8-carboxylic acid methyl ester Sodium borohydride (1.48 g, 39.22 mmol) was added portionwise to a stirred solution of chloroacetic acid (7.41 g, 78.45 mmol) in benzene (200 mL) and dry THF (20 mL) under nitrogen atmosphere at 10° C. The reaction mixture was stirred for 1.5 h (till no further evolution of hydrogen gas was observed) and compound of Example 15d (2.3 g, 6.54 mmol) was added, and the reaction mixture was refluxed for 6 h. To the reaction mixture, 10% sodium bicarbonate solution (100 mL) was added and extracted with ethyl acetate (3×200 mL). The combined organic layer was washed with water (2×100 mL), brine (100 mL) and dried over anhydrous sodium sulfate. Solvent was removed and the crude product obtained was crystallized using ethyl acetate/hexane to obtain the title compound. Yield: 2.6 g (80%); $^1$H NMR (CDCl$_3$, 300 MHz): δ 2.65 (s, 3H, CH$_3$), 3.62-3.66 (m, 4H, 2CH$_2$), 3.72-3.76 (m, 4H, 2CH$_2$), 3.90 (s, 3H, OCH$_3$), 4.35 (d, J=12.3 Hz, 1H, CH$_A$H$_B$ SO), 4.62 (d, J=12.3 Hz, 1H, CH$_A$H$_B$ SO), 6.51 (d, J=2.98 Hz, 1H, Ar), 6.66 (d, J=3.05 Hz, 1H, Ar), 8.02 (d, J=1.47 Hz, 1H, Ar), 8.33 (d, J=1.78 Hz, 1H, Ar); MS: m/e (ES−) 492 (M−1).

EXAMPLE 16

4-Chloro-6-methyl-10,10-dioxo-2-piperazin-1-yl-10,11-dihydro-5-oxa-10lambda*6*-thia-dibenzo[a,d]-cycloheptene-8-carboxylic acid methyl ester hydrochloride Aqueous ammonia solution (25%, 300 mL) was added to 2-[bis-(2-chloroethyl)-amino]-4-chloro-6-methyl-10,10-dioxo-10,11-dihydro-5-oxa-10lambda*6*-thia-dibenzo[a,d]-cycloheptene-8-carboxylic acid (52 g, 0.109 mol) [prepared by alkaline hydrolysis of compound of Example 12] in methanol (100 mL). The reaction mixture was sealed under nitrogen atmosphere, kept at 110° C. for 9 h, cooled and the seal was opened. The reaction mixture was concentrated to remove solvent and ammonia, and azeotroped with toluene. The product was taken in methanolic HCl solution (300 mL) and stirred at 70° C. for 9 h. The reaction mixture was cooled, solid separated was filtered, washed with methanol and dried under vacuum to obtain the crude product. The crude product was dissolved in chloroform and treated with aqueous sodium carbonate to obtain the free base, which was purified by column chromatography (silica gel, 5% methanol in chloroform) to obtain freebase of the title compound. Yield: 32 g (68%). This was converted to the hydrochloride salt using methanolic HCl. mp: 277-280° C.; $^1$H NMR (DMSO-d$_6$, 300 MHz): δ 2.66 (s, 3H, CH$_3$), 3.19 (m, 4H, 2CH$_2$), 3.40 (m, 4H, 2CH$_2$), 3.85 (s, 3H, OCH$_3$), 5.10 (s, 2H, CH$_2$), 7.10 (s, 1H, Ar), 7.20 (s, 1H, Ar), 8.05 (s, 1H, Ar) and 8.20 (s, 1H, Ar); MS: m/e (ES+) 437 (M+1, free base); analysis: C$_{20}$H$_{22}$Cl$_2$N$_2$O$_5$S requires C, 50.75; H, 4.68; N, 5.92; Cl, 14.98; S, 6.77. found: C, 50.85; H, 4.62; N, 6.14; Cl, 15.30; S, 6.80%.

EXAMPLE 17

4-Chloro-6-methyl-10,10-dioxo-2-piperazin-1-yl-10, 11-dihydro-5-oxa-10lambda*6*-thia-dibenzo[a,d] cycloheptene-8-carboxylic acid methyl ester mesylate A solution of methane sulfonic acid (0.023 mL, 0.3612 mmol) in methanol (1 mL) was added to a solution of 4-chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.15 g, 0.344 mmol) in methanol (10 mL) at 25° C. and stirred for 15 min. The resultant precipitate was filtered, washed using methanol and dried to obtain the title compound. Yield: 0.13 g, (71%); mp 279-281° C.; $^1$H NMR (CDCl$_3$, 300 MHz): δ 2.30 (s, 3H, CH$_3$), 2.63 (s, 3H, CH$_3$), 3.22 (s, 4H, 2CH$_2$), 3.39 (s, 4H, 2CH$_2$), 3.85 (s, 3H, OCH$_3$), 5.17 (s, 2H, CH$_2$), 7.18 (s, 1H, Ar), 7.20 (s, 1H, Ar), 8.09 (s, 1H, Ar), 8.15 (s, 1H, Ar), 8.72 (s, 2H, NH$_2$); MS: m/e (ES+) 437 (M+1, free base); analysis: C$_{21}$H$_{25}$ClN$_2$O$_8$S$_2$ requires C, 47.32; H, 4.73; N, 5.26; Cl, 6.65; S, 12.03. found: C, 47.80; H, 4.93; N, 5.44; Cl, 7.07; S, 11.75%.

EXAMPLE 18

4-Chloro-6-methyl-10,10-dioxo-2-piperazin-1-yl-10, 11-dihydro-5-oxa-10lambda*6*-thia-dibenzo[a,d] cycloheptene-8-carboxylic acid A solution of sodium hydroxide (0.22 g, 5.49 mmol) in water (15 mL) was added to a solution of 4-chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.88 g, 1.83 mmol) in tetrahydrofuran (25 mL). The reaction mixture was stirred at 40° C. for 4 h, the solvent was removed under vacuum. The reaction mixture was acidified to pH 4-5 using 10% aqueous hydrochloric acid. The precipitate was filtered, washed with water and dried to obtain the title compound. Yield: 0.84 g, (98%); $^1$H NMR (DMSO-d$_6$, 300 MHz): δ 2.65 (s, 3H, CH$_3$), 3.26 (s, 4H, 2CH$_2$), 3.43 (s, 4H, 2CH$_2$), 5.16 (s, 2H, CH$_2$), 7.20 (s, 2H, Ar), 8.08 (s, 1H, Ar), 8.18 (s, 1H, Ar); MS: m/e (ES–) 421 (M–1); analysis: C$_{19}$H$_{19}$ClN$_2$O$_5$S.2H$_2$O requires C, 49.73; H, 5.05; N, 6.10; Cl, 7.73; S, 6.99. found: C, 50.27; H, 5.12; N, 6.12; Cl, 7.47; S, 6.92%.

EXAMPLE 19

4-Chloro-6-methyl-10,10-dioxo-2-piperazin-1-yl-10, 11-dihydro-5-oxa-10lambda*6*-thia-dibenzo[a,d] cycloheptene-8-carboxylic acid mesylate A solution of methane sulfonic acid (0.058 mL, 0.852 mmol) in methanol (1 mL) was added to a solution of compound of Example 18 (0.3 g, 0.710 mmol) in methanol (10 mL) at 25° C. and filtered. The solution was stirred for 1 h and the precipitated solid was filtered, washed using methanol and dried to obtain the title compound. Yield: 0.244 g, (66%); mp 278-280° C.; $^1$H NMR (DMSO-d$_6$, 300 MHz): δ 2.31 (s, 3H, CH$_3$), 2.62 (s, 3H, CH$_3$), 3.21 (s, 4H, 2CH$_2$), 3.38 (s, 4H, 2CH$_2$), 5.16 (s, 2H, CH$_2$), 7.19 (s, 1H, Ar), 7.19 (s, 1H, Ar), 8.06 (s, 1H, Ar), 8.13 (s, 1H, Ar), 8.80 (s, 1H, NH); MS: m/e (ES+) 423 (M+1, freebase); analysis: C$_{20}$H$_{23}$ClN$_2$O$_8$S$_2$ requires C, 46.29; H, 4.47; N, 5.40; Cl, 6.83; S, 12.36. found: C, 46.75; H, 4.26; N, 5.37; Cl, 7.33; S, 12.58%.

EXAMPLE 20

4-Chloro-2-(4-formyl-piperazin-1-yl)-6-methyl-10, 10-dioxo-10,11-dihydro-5-oxa-10lambda*6*-thia-dibenzo[a,d]cycloheptene-8-carboxylic acid methyl ester Sodium formate (0.1 g, 1.37 mmol) was added to a solution of 4-chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.3 g, 0.68 mmol) in formic acid (85%, 5 mL), and stirred at 90° C. for 15 h. The reaction mixture was diluted using water (10 mL), extracted using ethyl acetate, washed with water and brine. Solvent was removed and the crude product was purified by column chromatography (silica gel, 1.5% methanol in chloroform) to obtain the title compound. Yield: 0.11 g, (35%); $^1$H NMR (DMSO-d$_6$, 300 MHz): δ 2.62 (s, 3H, CH$_3$), 3.17-3.24 (m, 4H, 2CH$_2$), 3.47 (s, 4H, 2CH$_2$), 3.85 (s, 3H, OCH$_3$), 5.15 (s, 2H, CH$_2$), 7.13 (s, 1H, Ar), 7.17 (s, 1H, Ar), 8.06 (s, 1H, CHO), 8.08 (t, 1H, Ar), 8.14 (d, 1H, Ar); MS: m/e (ES+) 465 (M+1); analysis: C$_{21}$H$_{21}$ClN$_2$O$_6$S.0.5H$_2$O requires C, 53.23; H, 4.64; N, 5.91; Cl, 7.49; S, 6.75. found: C, 53.82; H, 4.48; N, 5.42; Cl, 8.07; S, 7.17%.

EXAMPLE 21

2-(4-Acetyl-piperazin-1-yl)-4-chloro-6-methyl-10, 10-dioxo-10,11-dihydro-5-oxa-10lambda*6*-thia-dibenzo[a,d]cycloheptene-8-carboxylic acid methyl ester Acetyl chloride (0.15 mL, 2.06 mmol) was added to a solution of 4-chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.3 g, 0.68 mmol) in dichloromethane (15 mL) and stirred at 20° C., for 10 min. To this, pyridine (0.33 mL, 4.12 mmol) was added and the mixture was stirred further for 18 h. The solvent was removed from the mixture and water (15 mL) was added. The pH of the reaction mixture was adjusted to 3 using aqueous hydrochloric acid (10%). The solid obtained was filtered and the crude obtained was purified by column chromatography (silica gel, 2% methanol in chloroform) to obtain the title compound. Yield: 0.3 g, (91%); $^1$H NMR (DMSO-d$_6$, 300 MHz): δ 2.02 (s, 3H, CH$_3$), 2.63 (s, 3H, CH$_3$), 3.15 (s, 2H, CH$_2$), 3.17 (s, 2H, CH$_2$), 3.55 (s, 4H, 2CH$_2$), 3.85, (s, 3H, OCH$_3$), 5.16 (s, 2H, CH$_2$), 7.09 (d, 1H, Ar), 7.15 (d, 1H, Ar), 8.08 (t, 1H, Ar), 8.15 (t, 1H, Ar); MS: m/e (ES+) 479 (M+1).

EXAMPLE 22

4-Chloro-2-[4-(2-hydroxy-ethyl)-piperazin-1-yl]-6-methyl-10,10-dioxo-10,11-dihydro-5-oxa-10lambda*6*-thia-dibenzo[a,d]cycloheptene-8-carboxylic acid methyl ester To a solution of 2-[bis-(2-chloroethyl)amino]-4-chloro-6-methyl10,10-dioxo-10,11-dihydro-5-oxa-10lambda*6*-thia-dibenzo[a,d]-cycloheptene-8-carboxylic acid [prepared by hydrolysis of compound of Example 12, 0.5 g, 1.044 mmol], in methanol (8 mL), aminoethanol (0.25 mL, 4.17 mmol) was added and heated to 120° C. in a sealed reactor for 4 h. The reaction mixture was cooled and the solvent was removed under reduced pressure. To the residue, methanolic HCl (20 mL) was added and refluxed for 3 h. Solvent was removed and the reaction mixture was basified to pH 8 using sodium carbonate solution and extracted using ethyl acetate (3×25 mL). The organic layer was washed with water and brine solution, concentrated and the crude product was purified by column chromatography (silica gel, 1% methanol in chloroform) to obtain the title compound. Yield: 0.317 g, (67.13%); $^1$H NMR (DMSO-$d_6$, 300 MHz): δ 2.4 (t, 2H, $CH_2$), 2.48 (s, 4H, $2CH_2$), 2.63 (s, 3H, $CH_3$), 3.17 (s, 4H, $2CH_2$), 3.41 (t, 2H, $CH_2$), 3.86 (s, 3H, $OCH_3$), 4.44 (t, 1H, OH), 5.15 (s, 2H, $CH_2$), 7.04 (s, 1H, Ar), 7.12 (s, 1H, Ar), 8.08 (s, 1H, Ar), 8.15 (s, 1H, Ar); MS: m/e (ES+) 481 (M+1); analysis: $C_{22}H_{25}ClN_2O_6S$ requires C, 54.94; H, 5.24; N, 5.82; Cl, 7.37; S, 6.67. found: C, 54.78; H, 5.34; N, 5.7; Cl, 7.87; S, 6.88%.

EXAMPLE 23

2-(4-Benzyl-piperazin-1-yl)-4-chloro-6-methyl-10,10-dioxo-10,11-dihydro-5-oxa-10lambda*6*-thia-dibenzo[a,d]cycloheptene-8-carboxylic acid methyl ester A mixture of cesium carbonate (0.33 g, 0.82 mmol) and benzyl chloride (0.1 mL, 0.82 mmol) was added to a solution of 4-chloro-6-methyl-10,10-dioxo-2-piperazin-1-yl-10,11-dihydro-5-oxa-10lambda*6*-thia-dibenzo[a,d]cyclo heptene-8-carboxylic acid methyl ester (free base of example 16, 0.3 g, 0.68 mmol) in DMF (10 mL) and heated at 80° C. for 5 h. Reaction mixture was concentrated, water (10 mL) was added and the solid filtered. The crude obtained was purified by column chromatography (silica gel, 1% to 3% methanol in chloroform) to obtain the title compound. Yield: 0.11 g, (30.4%); $^1$H NMR (DMSO-$d_6$, 300 MHz): δ 2.62 (s, 3H, $CH_3$), 3.18 (s, 4H, $2CH_2$), 3.31 (s, 4H, $2CH_2$), 3.50 (s, 2H, $CH_2$), 3.85 (s, 3H, $OCH_3$), 5.14 (s, 2H, $CH_2$), 7.04 (s, 1H, Ar), 7.11 (s, 1H, Ar), 7.3-7.32 (m, 5H, Ar), 8.08 (s, 1H, Ar), 8.14 (s, 1H, Ar); MS: m/e (ES+) 528 (M+1); analysis: $C_{27}H_{27}ClN_2O_5S$ requires C, 61.53; H, 5.16; N, 5.32; Cl, 6.73; S, 6.08. found: C, 61.22; H, 4.99; N, 4.82; Cl, 6.91; S, 6.15%.

EXAMPLE 24

4-Chloro-6-methyl-2-[4-(2-methyl-benzoyl)-piperazin-1-yl]-10,10-dioxo-10,11-dihydro-5-oxa-10lambda*6*-thia-dibenzo[a,d]cycloheptene-8-carboxylic acid methyl ester Carbonyl diimidazole (0.074 g 0.55 mmol) was added to a solution of 2-toluic acid (0.111 g, 0.67 mmol) in DMF (3 mL) and stirred at 22° C. for 1 h. To this, a solution of 4-chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.2 g, 0.45 mmol) in DMF (2 mL) was added and stirred at 22° C. for 1 h. Solvent was removed and ice water (5 mL) was added. The solid separated was filtered, washed with water. The crude product obtained was purified by column chromatography (silica gel, ethyl acetate/pet ether) to obtain the title compound. Yield: 0.093 g (53%); mp: 201-204° C.; $^1$H NMR (DMSO-$d_6$, 500 MHz): δ 2.23 (s, 3H, $CH_3$), 2.64 (s, 3H, $CH_3$), 3.15 (s, 2H, $CH_2$), 3.28 (s, 2H, $CH_2$), 3.34 (s, 2H, $CH_2$), 3.39 (s, 2H, $CH_2$), 3.87 (s, 3H, $OCH_3$), 5.16 (s, 2H, $CH_2$), 7.12 (s, 1H, Ar), 7.16 (s, 1H, Ar), 7.20 (m, 4H, Ar), 8.11 (s, 1H, Ar), 8.16 (s, 1H, Ar); MS: m/e (ES+) 555 (M+1).

EXAMPLE 25

4-Chloro-2-(4-methanesulfonyl-piperazin-1-yl)-6-methyl-10,10-dioxo-10,11-dihydro-5-oxa-10lambda*6*-thia-dibenzo[a,d]cycloheptene-8-carboxylic acid methyl ester Mesyl chloride (0.16 mL, 2.059 mmol) was added to a solution of 4-Chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.3 g, 0.687 mmol) in dichloromethane (20 mL) and stirred at 20° C. for 10 min. To this pyridine (0.3 mL, 4.12 mmol) was added and the reaction mixture was stirred further for 5 h. The reaction mixture was washed using aqueous hydrochloric acid 10% (15 mL), water and then brine solution. Solvent was removed and the crude product obtained was purified by column chromatography (silica gel, 1% methanol in chloroform) to obtain the title compound. Yield: 0.14 g, (38.45%); $^1$H NMR (DMSO-$d_6$, 300 MHz): δ 2.63 (s, 3H, $CH_3$), 2.90 (s, 3H, $CH_3$), 3.22 (s, 4H, $2CH_2$); 3.31 (s, 4H, $CH_2$); 3.85 (s, 3H, $OCH_3$); 5.16 (s, 2H, $CH_2$), 7.13 (d, 1H, Ar), 7.18 (s, 1H, Ar), 8.09 (t, 1H, Ar), 8.15 (d, 1H, Ar); MS: m/e (ES+) 515 (M+1); analysis: $C_{21}H_{23}ClN_2O_7S_2.H_2O$ requires C, 47.32; H, 4.73; N, 5.26; Cl, 6.65; S, 12.03. found: C, 46.86; H, 4.18; N, 4.96; Cl, 7.11; S, 12.57%.

EXAMPLE 26

4-(4-Chloro-8-methoxycarbonyl-6-methyl-10,10-dioxo-10,11-dihydro-5-oxa-10lambda*6*-thia-dibenzo[a,d]cyclohepten-2-yl)-piperazine-1-carboxylic acid benzyl ester Carbonyl diimidazole (0.34 g, 0.021 mmol) was added to a solution of benzyl alcohol (0.2 g, 0.014 mmol) in DMF (3 mL) and stirred at 22° C. for 1 h. To this, a solution of 4-chloro-6-methyl-10,10-dioxo-2-piperazin-1-yl-10,11-dihydro-5-oxa-10lambda*6*-thia-dibenzo[a,d]cycloheptene-8-carboxylic acid methyl ester (free base of example 16, 0.228 g, 0.016 mmol) in DMF (2 mL) was added dropwise and stirred at 22° C. for 1 h. Solvent was removed and ice water (5 mL) was added. The solid separated was filtered, washed with water. Crude was crystallised using ethyl acetate to obtain the title compound. Yield: 0.093 g (53%); mp: 170-173° C.; $^1$H NMR (DMSO-$d_6$, 300 MHz): δ2.47 (s, 3H, $CH_3$), 3.25 (s, 4H, $2CH_2$), 3.52 (s, 4H, $2CH_2$), 3.85 (s, 3H, $OCH_3$), 5.09 (s, 2H, $CH_2$), 5.15 (s, 2H, $CH_2$), 7.09 (s, 1H, Ar), 7.14 (s, 1H, Ar), 7.32 (m, 5H, Ar), 8.09 (s, 1H, Ar), 8.15 (s, 1H, Ar); MS: m/e (ES+) 572 (M+1).

EXAMPLE 27

4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carboxylic acid methyl ester hydrochloride Cyclopropyl amine (0.082 g, 14 mmol) was added to a stirred solution of compound of Example 27a (0.3 g, 5.9 mmol) in dry dimethylformamide (5 mL) under nitrogen atmosphere. The reaction mixture was stirred at 80° C. for 2 h. Solvent was partially removed and the reaction mixture was diluted with water (50 mL). Solid separated was filtered, washed with water and dried. The crude product obtained was purified by column chromatography (silica gel, 1% methanol/chloroform) and then converted to its hydrochloride salt using methanolic-HCl to obtain the title compound. Yield: 0.18 g (58.06%); mp: 205° C. dec.; $^1$H NMR (DMSO-$d_6$, 300 MHz): δ 0.79-0.81 (m, 2H, $CH_2$), 1.07 (bs, 2H, $CH_2$), 2.60 (s, 3H, $CH_3$), 2.89 (bs, 1H, CH), 3.65-3.70 (m, 4H, 2$CH_2$), 3.88 (s, 3H, $OCH_3$), 4.12-4.15 (m, 2H, $CH_2$), 5.37 (s, 2H, $CH_2$), 7.61 (s, 1H, Ar), 7.68 (s, 1H, Ar), 8.15 (s, 1H, Ar), 8.18 (s, 1H, Ar); MS: m/e (ES+) 490 (M+1, free base).

EXAMPLE 27a

4-Chloro-2-[(2-chloro-acetyl)-(2-chloro-ethyl)-amino]-6-methyl-10,10dioxo-10,11-dihydro-5-oxa-10lambda*6*-thia-dibenzo[a,d]-cycloheptene-8-carboxylic acid methyl ester 4-Chloro-2-(2-chloro-ethylamino)-6-methyl-10,10-dioxo-10,11-dihydro-5-oxa-10lambda*6*-thia-dibenzo[a,d]-cycloheptene-8-carboxylic acid methyl ester (prepared by following the method described in example 29a or example 29b, 1.9 gm, 4.4 mmol) was added to chloroacetyl chloride (6 mL) at room temperature. Reaction mixture was then stirred at 90° C. for 1 h. Reaction mixture was cooled and diluted using ice water (100 mL). The solid separated was filtered, washed with water and dried to obtain the title compound. Yield: 1.85 g, (83%); $^1$H NMR (DMSO-$d_6$, 300 MHz): δ 2.60 (s, 3H, $CH_3$), 3.67 (t, 2H, $CH_2$), 3.88 (s, 3H, $OCH_3$), 3.99 (t, 2H, $CH_2$), 4.27 (bs, 2H, $CH_2$), 5.31 (s, 2H, $CH_2$), 7.66 (s, 1H, Ar), 7.80 (s, 1H, Ar), 8.17 (s, 1H, Ar), 8.19 (s, 1H, Ar); MS: m/e (ES+) 505 (M+1).

EXAMPLE 28

4-Chloro-6-methyl-10,10-dioxo-2-piperazin-1-yl-10,11-dihydro-5-oxa-10lambda*6*-thia-dibenzo[a,d]cycloheptene-8-carboxylic acid isopropyl ester hydrochloride Concentrated sulphuric acid (1 mL) was added dropwise to a stirred solution of compound of Example 18 (0.5 g, 1.18 mmol) in dry isopropanol (50 mL) at 90° C. The reaction mixture was stirred at 90° C. for 2 h. Solvent was removed and the residue was taken in chloroform (100 mL) and this was neutralized using sodium carbonate solution (10%). Chloroform layer was washed with water, brine and dried over sodium sulphate. Solvent was removed and the product obtained was converted to hydrochloride salt by using isopropanol/ethereal-HCl to obtain the title compound. Yield: 0.4 g (67.79%); mp: 262-64° C.; $^1$H NMR (DMSO-$d_6$, 300 MHz): δ 1.29 (d, 6H, 2$CH_3$), 2.63 (s, 3H, $CH_3$), 3.18 (bs, 4H, 2$CH_2$), 3.44 (bs, 4H, 2$CH_2$), 5.11 (s, 1H, CH), 5.17 (s, 2H, $CH_2$), 7.19 (s, 2H, Ar), 8.07 (s, 1H, Ar), 8.11 (s, 1H, Ar), 9.45 (bs, 2H, NH, HCl); MS: m/e (ES+) 465 (M+1, free base).

EXAMPLE 29

4-Chloro-2-[1,4]diazepan-1-yl-6-methyl-10,10-dioxo-10,11-dihydro-5-oxa-10lambda*6*-thia-dibenzo[a,d]cycloheptene-8-carboxylic acid methyl ester hydrochloride Ammonia solution (25%, 4 mL) was added to a stirred solution of 4-chloro-2-[(2-chloro-ethyl)-3-(chloro-propyl)-amino]-6-methyl-10,10-dioxo-10,11-dihydro-5-oxa-lambda*6*-thia-dibenzo[a,d]cycloheptene-8-carboxylic acid (1.0 g, 2.1 mmol) [obtained by hydrolysis of compound of Example 29b] in methanol (10 mL). Reaction mixture was sealed under nitrogen atmosphere and stirred at 110° C. for 6.5 h. Solvent was removed, solid obtained was azeotroped using toluene (20 mL). The residue obtained was suspended in methanolic-HCl and refluxed overnight (18 h). Solvent was removed and chloroform (100 mL) was added. The solution was neutralized using sodium carbonate solution (10%). Chloroform layer was washed with water, brine and dried over sodium sulphate. The crude product obtained was purified by column chromatography (silica gel, 4% methanol/chloroform) and then converted to its hydrochloride salt using methanolic-HCl to obtain the title compound. Yield: 0.275 g (29.25%); mp: 270° C. dec.; $^1$H NMR (DMSO-$d_6$, 300 MHz): δ 2.06 (bs, 2H, $CH_2$), 2.63 (s, 3H, $CH_3$), 3.09 (bs, 2H, $CH_2$), 3.19 (bs, 2H, $CH_2$), 3.70 (t, 2H, $CH_2$), 3.85 (bs, 2H, $CH_2$), 3.90 (s, 3H, $OCH_3$), 5.15 (s, 2H, $CH_2$), 6.91 (s, 1H, Ar), 6.99 (s, 1H, Ar), 8.08 (s, 1H, Ar), 8.15 (s, 1H, Ar), 9.06 (bs, 1H, NH); MS: m/e (ES+) 451 (M+1, free base).

EXAMPLE 29a

4-Chloro-2-(3-chloropropylamino)-6-methyl-10,10dioxo-10,11-dihydro-5-oxa-10lambda*6*-thia-dibenzo[a,d]-cycloheptene-8-carboxylic acid methyl ester Powdered sodium-borohydride (0.93 g, 24 mmol) was added in portions at 0° C., to a solution of chloropropionic acid (5.32 g, 49 mmol) in THF (13 mL), and benzene (210 mL). Reaction mixture was warmed to room temperature and stirred for 1 h, and compound of Example 1 (3.0 g, 8.17 mmol) was added. Reaction mixture was refluxed for 3 h. Reaction mixture was cooled and quenched using sodium bicarbonate solution, and extracted with ethylacetate. Organic layer was washed with water (100 mL) and brine (50 mL). The crude product obtained was purified by column chromatography (silica gel, ethylacetate/pet. ether) to obtain the title compound. Yield: 3.7 g (99%); $^1$H NMR (DMSO-$d_6$, 300 MHz): δ 1.96 (q, 2H, $CH_2$), 2.62 (s, 3H, $CH_3$), 3.11 (q, 2H, $CH_2$), 3.72 (t, 2H, $CH_2$), 3.85 (s, 3H, $OCH_3$), 5.12 (s, 2H, $CH_2$), 6.29 (s, 1H, Ar), 6.31 (s, 1H, Ar), 8.07 (s, 1H, Ar), 8.13 (s, 1H, Ar); MS: m/e (EI) 443 (M+).

EXAMPLE 29b

4-Chloro-2-[(2-chloro-ethyl)(3-chloro-propyl)-amino]-6-methyl-10,10dioxo-10,11-dihydro-5-oxa-10lambda*6*-thia-dibenzo[a,d]-cycloheptene-8-carboxylic acid methyl ester Powdered sodium-borohydride (0.33 g, 8.6 mmol) was added in portions at 0° C., to a solution of chloroacetic acid (1.68 g, 17 mmol) in THF (6 mL), and benzene (90 mL). Reaction mixture was warmed to room temperature and stirred for 1 h, and compound of Example 29a (1.3 g, 2.9 mmol) was added. Reaction mixture was refluxed for 3 h. Reaction mixture was cooled and quenched using sodium bicarbonate solution, and extracted with ethylacetate. Organic layer was washed with water (100 mL) and brine (50 mL). The crude product obtained was purified by column chromatography (silica gel, ethylacetate/pet-ether) to obtain the title compound. Yield: 1.25 g (87%); $^1$H NMR (DMSO-$d_6$, 300 MHz): δ 2.00 (t, 2H, $CH_2$), 2.63 (s, 3H, $CH_3$), 3.66 (t, 2H, $CH_2$), 3.69-3.80 (m, 6H, 3×$CH_2$), 3.85 (s, 3H, $OCH_3$), 5.16 (s, 2H, $CH_2$), 6.74 (s, 1H, Ar), 6.85 (s, 1H, Ar), 8.08 (s, 1H, Ar), 8.14 (s, 1H, Ar); MS: m/e (EI) 506 (M+).

EXAMPLE 30

4-Chloro-6-methyl-2-morpholin-4-yl-10,10-dioxo-10,11-dihydro-5-oxa-10lambda*6*-thia-dibenzo[a,d]cycloheptene-8-carboxylic acid methyl ester Catalytic amount of p-toluene sulphonic acid (PTSA) was added to a stirred solution of compound of Example 13 (1 g, 2.19 mmol) in xylene (50 mL). Reaction mixture was refluxed in Dean-Stark apparatus for 6 h and xylene was removed by distillation. Reaction mixture was diluted with 50 mL water, neutralized using 10% sodium bicarbonate solution and extracted using ethyl acetate (3×50 mL), washed with brine (2×10 mL), dried on sodium sulphate. The crude product obtained was purified by column chromatography (silica gel, ethylacetate/pet. ether) to obtain the title compound. Yield: 0.32 g, (33%); mp: >320° C.; $^1$H NMR (DMSO-$d_6$, 300 MHz): δ 2.68 (s, 3H, $CH_3$), 3.15 (s, 4H, 2$CH_2$), 3.74 (s, 4H, 2$CH_2$), 3.90 (s, 3H, $OCH_3$), 4.65 (s, 2H, $CH_2$), 6.76 (s, 1H, Ar), 6.88 (s, 1H, Ar), 8.06 (s, 1H, Ar), 8.44 (s, 1H, Ar); MS: m/e (EI) 437 (M+).

EXAMPLE 31

3-(2-Amino-ethylamino)-4-chloro-6-methyl-10,10-dioxo-10,11-dihydro-5-oxa-10lambda*6*-thia-dibenzo[a,d]cycloheptene-8-carboxylic acid methyl ester hydrochloride (Compound A)

EXAMPLE 32

4-Chloro-6-methyl-10,10-dioxo-3-piperazin-1-yl-10,11-dihydro-5-oxa-10lambda*6*-thia-dibenzo[a,d]cycloheptene-8-carboxylic acid methyl ester hydrochloride (Compound B)

4-Chloro-6-methyl-3-nitro-10,10-dioxo-10,11-dihydro-5-oxa-10lambda*6*-thia-dibenzo[a,d]cycloheptene-8-carboxylic acid methyl ester is the minor component obtained in the scale up of Example 1j, which on processing by the methods described in Example 1 and Example 12 yielded a mixture of 3-(2-chloro-ethyl-amino)-4-chloro-6-methyl-10,10-dioxo-10,11-dihydro-5-oxa-lambda*6*-thia-dibenzo[a,d]cycloheptene-8-carboxylic acid methyl ester and 3-[bis-(2-chloro-ethyl)-amino]-4-chloro-6-methyl-10,10-dioxo-10,11-dihydro-5-oxa-lambda*6*-thia-dibenzo[a,d]cycloheptene-8-carboxylic acid methyl ester. These esters were hydrolysed to obtain the corresponding acids.

Aqueous ammonia (2 mL) was added to a stirred solution containing a mixture of 3-(2-chloro-ethyl-amino)-4-chloro-6-methyl-10,10-dioxo-10,11-dihydro-5-oxa-lambda*6*-thia-dibenzo[a,d]cycloheptene-8-carboxylic acid and 3-[bis-(2-chloro-ethyl)-amino]-4-chloro-6-methyl-10,10-dioxo-10,11-dihydro-5-oxa-lambda*6*-thia-dibenzo[a,d]cycloheptene-8-carboxylic acid [(ratio 98:2), 0.7 g, 1.46 mmol)] in methanol (10 mL). Reaction mixture was sealed under nitrogen atmosphere and stirred at 120° C. for 6.5 h. Reaction mixture was cooled and the solvent was removed. Solid obtained was azeotroped using toluene and then suspended in methanolic-HCl (20 mL) and refluxed for 2 h. Solvent was removed and the residue was suspended in chloroform (50 mL) and neutralized using sodium carbonate solution (10%). Chloroform layer was washed with water, brine and dried over sodium sulphate. The crude product obtained was purified by column chromatography (silica gel, 2% methanol chloroform) to obtain the free base of compound A and free base of compound B.

Free base of compound A and free base of compound B were converted to the hydrochloride salt using methanolic HCl to obtain the title compound A (Example 31) and title compound B (Example 32).

Compound A

Yield: 0.085 g; mp: 202° C. dec.; $^1$H NMR (DMSO-$d_6$, 300 MHz): δ 2.66 (s, 3H, $CH_3$), 2.99 (bs, 2H, $CH_2$), 3.39 (bs, 2H, $CH_2$), 3.86 (s, 3H, $OCH_3$), 5.21 (s, 2H, $CH_2$), 5.31 (s, 2H, $NH_2$), 6.66 (d, 1H, Ar), 7.33 (d, 1H, Ar), 7.98 (bs, 2H, NH, HCl), 8.10 (s, 1H, Ar), 8.11 (s, 1H, Ar); MS: m/e (ES+) 411 (M+1, free base).

Compound B

Yield: 0.29 g; mp: 235-37° C.; $^1$H NMR (DMSO-$d_6$, 300 MHz): δ 2.66 (s, 3H, $CH_3$), 3.08 (bs, 4H, 2$CH_2$), 3.33 (bs, 4H, 2$CH_2$), 3.87 (s, 3H, $OCH_3$), 5.31 (s, 2H, $CH_2$), 7.31 (d, 1H, Ar), 7.64 (d, 1H, Ar), 8.15 (s, 2H, Ar), 9.05 (bs, 2H, NH, HCl); MS: m/e (ES+) 437 (M+1); analysis: $C_{20}H_{22}Cl_2N_2O_5S.H_2O$ requires C, 48.84; H, 4.88; N, 5.69; Cl, 14.44; S, 6.51. found: C, 48.94; H, 4.97; N, 5.73; Cl, 14.62; S, 6.63.

EXAMPLE 33

(4-Chloro-6-methyl-10,10-dioxo-2-piperazine-1-yl-10,11-dihydro-5-oxa-10lambda*6*-thia-dibenzo[a,d]cyclohepten-8-yl)-acetic acid methyl ester hydrochloride Aqueous ammonia (5 mL) was added to a stirred solution of {2-[bis-(2-chloro-ethyl)-amino]-4-chloro-6-methyl-10,10-dioxo-10,11-dihydro-5-oxa-lambda*6*-thia-dibenzo[a,d]cycloheptene-8-yl}-acetic acid (0.4 g, 0.88 mmol) [obtained by hydrolysis of compound of Example 33h] in methanol (20 mL). The reaction mixture was sealed under nitrogen atmosphere and stirred at 120° C. for 6 h. Reaction mixture was cooled and solvent was removed. The residue obtained was azeotroped with toluene and then suspended in methanolic-HCl (20 mL) and refluxed for 3 h and solvent was removed. The residue obtained was suspended in chloroform (50 mL) and neutralized using sodium carbonate solution (10%). Chloroform layer was washed with water, brine and dried over sodium sulphate. The crude product obtained was purified by column chromatography (silica gel, 2% methanol chloroform) to obtain the compound, which was converted to the hydrochloride salt using methanolic HCl to obtain the title compound. Yield: 0.23 g (58%); mp: 280° C. dec.; $^1$H NMR (DMSO-$d_6$, 300 MHz): δ 2.56 (s, 3H, $CH_3$), 3.19 (bs, 4H, $2CH_2$), 3.41 (bs, 4H, $2CH_2$), 3.59 (s, 3H, $OCH_3$), 3.74 (s, 2H, $CH_2$), 5.06 (s, 2H, $CH_2$), 7.17 (s, 2H, Ar), 7.43 (s, 1H, Ar), 7.56 (s, 1H, Ar), 9.17 (bs, 2H, NH, HCl); MS: m/e (ES+) 451 (M+1). analysis: $C_{21}H_{24}Cl_2N_2O_5S$ requires C, 51.75; H, 4.96; N, 5.74; Cl, 14.55; S, 6.58. found: C, 51.47; H, 4.76; N, 6.04; Cl, 14.96; S, 6.89.

EXAMPLE 33a

4-Chloro-6-methyl-10,10-dioxo-10,11-dihydro-5-oxa-10lambda*6*-thia-dibenzo[a,d]cyclohepten-8-yl)methanol Boranedimethylsulphide complex (28 mL, 0.292 mol) was added to a stirred solution of 4-chloro-6-methyl-10,10-dioxo-10,11-dihydro-5-oxa-lambda*6*-thia-dibenzo[a,d]cyclo-heptene-8-carboxylic acid (19.75 g, 0.058 mol) [obtained by hydrolysis of 1i] in dry THF (200 mL) under nitrogen atmosphere at 10° C. The reaction mixture was stirred at 60° C. for 3 h. Reaction mixture was cooled and quenched with methanol, and solvent was removed. The residue was suspended in ethylacetate (200 mL) and washed with water, brine and dried over sodium sulphate. Organic layer was concentrated to obtain the title compound. Yield: 19 g (100%); $^1$H NMR (DMSO-$d_6$, 300 MHz): δ 2.60 (s, 3H, $CH_3$), 4.46 (d, 2H, $CH_2$), 5.17 (s, 2H, $CH_2$), 5.38 (t, 1H, OH), 7.31 (t, 1H, Ar), 7.47 (s, 1H, Ar), 7.55-7.60 (m, 3H, Ar); MS: m/e (EI) 324 (M+).

EXAMPLE 33b

4-Chloro-8-chloromethyl-6-methyl-11-H-5oxa-10-thia.dibenzo-[a,d]cycloheptene-10,10-dioxide Thionyl chloride (80 mL) was added dropwise to a solution of compound of Example 33a (12 g, 37 mmol). Reaction mixture was stirred at room temperature (22° C.) for 2 h. Thionyl chloride was distilled-off and the residue was suspended in chloroform, washed with water (100 mL), brine (100 mL) and dried over sodium sulphate. Organic layer was concentrated to obtain the title compound. Yield: 11.77 g (93%); $^1$H NMR (DMSO-$d_6$, 300 MHz): δ 2.61 (s, 3H, $CH_3$), 4.79 (s, 2H, $CH_2$), 5.21 (s, 2H, $CH_2$), 7.34 (t, 1H, Ar), 7.58 (d, 1H, Ar), 7.60 (d, 1H, Ar), 7.64 (s, 1H, Ar), 7.76 (s, 1H, Ar); MS: m/e (EI) 342 (M+).

EXAMPLE 33c

4-Chloro-6-methyl-10,10-dioxo-10,11-dihydro-5-oxa-lambda*6*-thia-dibenzo[a,d]cyclohepten-8-yl)-acetonitrile Magnesium sulphate (0.113 g, 0.94 mmol) in water (30 mL) was added to a solution of compound of Example 33b (3.24 g, 9.4 mmol) in DMF (200 mL) followed by addition of sodium cyanide (1.024 g, 20.8 mmol). Reaction mixture was stirred at room temperature (22° C.) overnight (18 h). Reaction was quenched, by adding ferric chloride solution, and DMF was removed under vacuum. Residue was suspended in ethyl acetate (100 mL), washed with water (50 mL), brine (50 mL) and dried over sodium sulphate. Organic layer was concentrated to obtain the title compound. Yield: 2.7 g (85.44%); $^1$H NMR (DMSO-$d_6$, 300 MHz): δ 2.61 (s, 3H, $CH_3$), 4.08 (s, 2H, $CH_2$), 5.23 (s, 2H, $CH_2$), 7.35 (t, 1H, Ar), 7.53-7.60 (m, 3H, Ar), 7.67 (s, 1H, Ar); MS: m/e (EI) 333 (M+).

EXAMPLE 33d

4-Chloro-6-methyl-10,10-dioxo-10,11-dihydro-5-oxa-lambda*6*-thia-dibenzo[a,d]cyclohepten-8-yl)-acetic acid Compound of Example 33c (2.5 g, 0.0074 mol) was suspended in mixture of acetic acid (25 mL) and ortho-phosphoric acid (25 mL). Reaction mixture was refluxed for 1.5 h, cooled, and neutralized using 10% sodium bicarbonate solution and extracted with ethyl acetate. Aqueous layer was acidified using dilute HCl and extracted with ethyl acetate. The organic layer was washed with water (50 mL), brine (50 mL) and dried over sodium sulphate. The crude product obtained was purified by column chromatography (silica gel, methanol-chloroform) to obtain the title compound. Yield: 1.98 g, (75.57%); $^1$H NMR (DMSO-$d_6$, 300 MHz): δ 2.58 (s, 3H, $CH_3$), 3.63 (s, 2H, $CH_2$), 5.11 (s, 2H, $CH_2$), 7.32-7.60 (m, 5H, Ar); MS: m/e (EI) 352 (M+).

EXAMPLE 33e

4-Chloro-6-methyl-10,10-dioxo-10,11-dihydro-5-oxa-lambda*6*-thia-dibenzo[a,d]cyclohepten-8-yl)-acetic acid methyl ester Concentrated sulphuric acid (0.66 mL) was added to a stirred solution of compound of Example 33d in dry methanol (100 mL) at reflux temperature. Reaction was refluxed for 6 h. Solvent was removed and the crude was suspended in ethyl acetate. The organic layer was washed with 10% sodium-bicarbonate solution (50 mL), water (100 mL) and dried over sodium sulphate. The crude product obtained was purified by column chromatography (silica gel, methanol-chloroform) to obtain the title compound. Yield: 3.5 g, (67.43%); $^1$H NMR (DMSO-$d_6$, 300 MHz): δ 2.56 (s, 3H, $CH_3$), 3.56 (s, 3H, $OCH_3$), 3.70 (s, 2H, $CH_2$), 5.10 (s, 2H, $CH_2$), 7.32 (t, 1H, Ar), 7.48 (s, 1H, Ar), 7.51-7.57 (m, 3H, Ar); MS: m/e (EI) 366 (M+).

EXAMPLE 33f (4-Chloro-6-methyl-2-nitro-10,10-dioxo-10,11-dihydro-5-oxa-lambda*6*-thia-dibenzo[a,d]cyclohepten-8-yl)-acetic acid Cooled sulphuric acid (6 mL) was added to a solution of compound of Example 33e (2 g, 5.4 mmol) in concentrated nitric acid (30 mL) at 0° C. Reaction mixture was warmed to room temperature (22° C.) and stirred for 1.5 h. The reaction mixture was slowly poured into cold water (100 mL), extracted with ethyl acetate. The organic layer was washed with water (50 mL) and dried over sodium sulphate. Organic layer was concentrated to obtain the title compound. Yield: 1.62 g, (72.32%); $^1$H NMR (DMSO-$d_6$, 300 MHz): δ 2.57 (s, 3H, $CH_3$), 3.66 (s, 2H, $CH_2$), 5.39 (s, 2H, $CH_2$), 7.38 (s, 1H, Ar), 7.52 (s, 1H, Ar), 8.47 (s, 1H, Ar), 8.50 (s, 1H, Ar); MS: m/e (EI) 397 (M+).

EXAMPLE 33g (2-Amino-4-chloro-6-methyl-10,10-dioxol-10,11-dihydro-5-oxa-lambda*6*-thia-dibenzo[a,d]cyclohepten-8-yl)-acetic acid methyl ester Activated Raney-Nickel (1.6 g) was added to a solution of (4-chloro-6-methyl-2-nitro-10,10-dioxo-10,11-dihydro-5-oxa-10lambda*6*-thia-5-aza-dibenzo[a,d]-cyclohepten-8-yl)acetic acid methyl ester (1 g) in DMF (50 mL) [obtained by esterification of compound of Example 33f]. Reaction mixture was kept for hydrogenation at 45 psi for 3 h. Catalyst was removed by filtering over a bed of celite, washed with DMF and concentrated to reduce the volume to half. Reaction mixture was diluted with water, and the solid obtained was filtered, washed with water and dried to obtain the title compound. Yield: 0.4 g (67.79%); mp. 262-64° C.; $^1$H NMR (DMSO-d$_6$, 300 MHz): δ 2.54 (s, 3H, CH$_3$), 3.58 (s, 3H, OCH$_3$), 3.73 (s, 2H, CH$_2$), 5.03 (s, 2H, CH$_2$), 6.7-6.8 (m, 2H, Ar), 7.5-7.6 (m, 2H, Ar); MS: m/e (ES+) 381 (M+1).

EXAMPLE 33h

{2-[Bis-(2-chloro-ethyl)-amino]-4-chloro-6-methyl-10,10-dioxo-10,11-dihydro-5-oxa-10lambda*6*-thia-dibenzo[a,d]cyclohepten-8-yl}-acetic acid methyl ester Powdered sodium borohydride (0.258 g, 7.1 mmol) was added portionwise to a stirred solution of chloroacetic acid (1.37 g, 14 mmol) in benzene (20 mL) and THF (2.5 mL) at 0° C. under nitrogen atmosphere. Reaction mixture was warmed to room temperature (22° C.) and stirred for 1.5 h. To this, compound of Example 33 g (0.5 g, 1.19 mmol) was added. Reaction mixture was refluxed for 3.5 h, cooled and quenched with 10% sodium bicarbonate solution and was extracted using ethylacetate (2×100 mL). The organic layer was washed with water (100 mL), brine (50 mL) and dried over sodium sulphate. The crude product obtained was purified by column chromatography (silica gel, pet ether-chloroform) to obtain the title compound. Yield: 0.46 g (76.66%); $^1$H NMR (CDCl$_3$, 300 MHz): δ 2.63 (s, 3H, CH$_3$), 3.58 (s, 2H, CH$_2$), 3.68 (s, 3H, OCH$_3$), 3.61-3.65 (m, 8H, 4×CH$_2$), 4.64 (s, 2H, CH$_2$), 6.52 (s, 1H, Ar), 6.66 (s, 1H, Ar), 7.34 (s, 1H, Ar), 7.61 (s, 1H, Ar); MS: m/e (ES+) 508 (M+1).

EXAMPLE 34

[4-Chloro-2-(4-ethyl-piperazin-1-yl)-6-methyl-10,10-dioxo-10,11-dihydro-5-oxa-10lambda*6*-thia-dibenzo[a,d]cyclohepten-8-yl]-methanol Boranedimethylsulphide complex (0.85 mL, 8.7 mmol) was added at 10° C. to a stirred solution of 2-(4-acetyl-piperazin-1-yl)-4-chloro-6-methyl-10,10-dioxo-10,11-dihydro-5-oxa-lambda*6*-thia-dibenzo[a,d]cycloheptene-8-carboxylic acid (0.8 g, 1.7 mmol) [obtained by hydrolysis of compound of Example 21] in dry THF (70 mL) under nitrogen atmosphere. The reaction mixture was stirred at 60° C. for 2 h. Reaction mixture was cooled and quenched with methanol and the solvent was removed. Solid was suspended in ethylacetate (100 mL) and washed with water, brine and dried over sodium sulphate. The crude product obtained was purified by column chromatography (silica gel, 2% methanol-chloroform) to obtain the title compound. Yield: 0.5 g (67.74%); mp: 230-32° C.; $^1$H NMR (DMSO-d$_6$, 300 MHz): δ 1.88 (t, 3H, CH$_3$), 2.57 (s, 3H, CH$_3$), 2.86 (t, 2H, CH$_2$), 2.88-2.91 (m, 4H, 2CH$_2$), 3.31-3.41 (m, 4H, 2CH$_2$), 4.45 (d, 2H, CH$_2$), 5.04 (s, 2H, CH$_2$), 5.37 (t, 1H, OH), 7.07 (s, 1H, Ar), 7.13 (s, 1H, Ar), 7.43 (s, 1H, Ar), 7.58 (s, 1H, Ar); MS: m/e (ES+) 437 (M+1).

EXAMPLE 35

4-Chloro-6-methyl-10,10-dioxo-2-piperazin-1-yl-10,11-dihydro-5-oxa-10lambda*6*-thia-dibenzo[a,d]cycloheptene-8-carbaldehyde DMSO (2.6 mL, 37.5 mmol) was added at −70° C. to a solution of oxalyl chloride (0.46 mL, 37.5 mmol) in dichloromethane (10 mL). Reaction mixture was stirred for 5 minutes and to this (4-chloro-6-methyl-10,10-dioxo-2-piperazin-1-yl-10,11-dihydro-5-oxa-10lambda*6*-thia-dibenzo[a,d]-cyclohepten-8-yl)-methanol (0.489 g, 1.19 mmol) [obtained by following the procedure described in Example 34] in dichloromethane (5 mL) was added. Reaction mixture was stirred for 5 minutes and to this triethylamine (8.4 mL, 62.5 mmol) was added. Reaction mixture was warmed to room temperature (22° C.) and stirred for 0.5 h. the reaction mixture was diluted with dichloromethane (200 mL), washed with water (100 mL), brine (50 mL) and dried over sodium sulphate. The crude product obtained was purified by column chromatography (silica gel, ethylacetate-pet ether) to obtain the title compound. Yield: 0.2 g (42%); $^1$H NMR (DMSO-d$_6$, 300 MHz): δ 2.64 (s, 3H, CH$_3$), 3.20 (s, 4H, 2CH$_2$), 3.20 (s, 4H, 2CH$_2$), 5.15 (s, 2H, CH$_2$), 7.14 (d, 2H, Ar), 8.03 (s, 1H, Ar), 8.24 (s, 1H, Ar), 9.97 (s, 1H, CHO); MS: m/e (EI) 406 (M+).

EXAMPLE 36

4-Chloro-6-methyl-10,10-dioxo-2-piperazin-1-yl-10,11-dihydro-5-oxa-10lambda*6*-thia-dibenzo[a,d]cycloheptene-8-carboxylic acid cyclopropylamide hydrochloride 1,1'-Carbonyldiimidazole (0.172 g, 11 mmol) was added at 25° C., to a stirred solution of compound of Example 18 (0.3 g, 7 mmol) in dry DMF (10 mL) under nitrogen atmosphere. The reaction mixture was stirred for 2 h, and cyclopropyl amine (0.06 mL, 8.4 mmol) was added. The reaction mixture was stirred at 25° C. for 2 h. Solvent was partially removed and the reaction mixture was diluted with water (50 mL), The solid separated was filtered, washed with water and dried. The product was converted to its hydrochloride salt using methanolic-HCl to obtain the title compound. Yield: 0.15 g (42.5%); $^1$H NMR (DMSO-d$_6$, 300 MHz): δ 0.56 (s, 2H, CH$_2$), 0.66 (d, 2H, CH$_2$), 2.61 (s, 3H, CH$_3$), 2.82 (bs, 1H, CH), 3.20-3.36 (m, 8H, 4CH$_2$), 5.11 (s, 2H, CH$_2$), 7.14 (d, 1H, Ar), 7.66 (d, 1H, Ar), 8.01 (s, 1H, Ar), 8.13 (s, 1H, Ar), 8.67 (s, 1H, NH); MS: m/e (ES+) 462 (M+1, freebase).

EXAMPLE 37

2-Amino-4-chloro-6-methyl-10,10-dioxo-10,11-dihydro-5H-10lambda*6*-thia-5-aza-dibenzo[a,d]-cycloheptene-8-carboxylic acid methylester Activated Raney-Nickel (0.06 g) was added to a solution of compound of Example 37f (0.3 g, 0.75 mmol) in DMF (50 mL). The reaction mixture was subjected to hydrogenation (30 psi pressure) for 1 h. Catalyst was filtered-off, washed with dimethylformamide and concentrated to reduce the volume to half. The reaction mixture was diluted with water, solid obtained was filtered, washed with water and dried under vacuum to obtain the title compound. Yield: 0.176 g, (63%); mp: 278-280° C.; $^1$H NMR (DMSO-$d_6$, 300 MHz): δ 2.60 (s, 3H, $CH_3$), 3.90 (s, 3H, $OCH_3$), 4.80 (s, 2H, $CH_2$), 5.60 (s, 1H, NH), 6.70 (s, 1H, Ar), 6.75 (s, 1H, Ar), 7.50 (s, 1H, NH), 7.95 (s, 1H, Ar), 8.30 (s, 1H, Ar); MS: m/e (EI) 366 (M+). analysis: $C_{16}H_{15}ClN_2O_4S$ requires C, 52.39; H, 4.12; N, 7.64; Cl, 9.67; S, 8.75; C, 52.29; H, 4.17; N, 7.07; Cl, 9.92; S, 9.02%.

EXAMPLE 37a

1-Bromomethyl-3-chloro-2-nitrobenzene

N-Bromosuccinimide (4.67 g, 26.23 mmol) was added to a stirred solution of 6-methyl-2-chloro-1-nitrobenzene (4.5 g, 26.23 mmol) in distilled carbon-tetrachloride. Benzoyl peroxide (0.01 g) was added to the reaction mixture and the mixture was refluxed for 8 h. The solid separated was filtered. The filtrate was concentrated to get the crude product, which was purified by using column chromatography (silica gel, pet.ether 60-80° C.) to obtain the title compound. Yield: 2.69 g, (41%); MS: m/e (CI) 253 (M+1).

EXAMPLE 37b

4-Bromo-3-(3-chloro-2-nitro-benzylsulfanyl)-5-methyl-benzoic acid methyl ester

Triethylamine (1.16 mL, 8.61 mmol) was added to a stirred solution of compound of Example 37a (2.87 g, 11.78 mmol) and compound of Example 1f (1.5 g, 5.74 mmol) in dry dichloromethane (75 mL). The reaction mixture was stirred at 0° C. for 20 min, was poured in water (100 mL) and extracted with chloroform (2×50 mL). The combined extract was washed with water (50 mL), brine (50 mL) and concentrated under vacuum to obtain the crude product, which was purified by column chromatography (silica gel, 5% ethyl acetate in pet ether 60-80° C.) to obtain the title compound. Yield: 1.93 g, (77.82%); $^1$H NMR (DMSO-$d_6$, 300 MHz): δ 2.55 (s, 3H, $CH_3$), 3.90 (s, 3H, $OCH_3$), 4.25 (s, 2H, $CH_2$), 7.45 (s, 1H, Ar), 7.50-7.60 (m, 2H, Ar), 7.75 (s, 1H, Ar), 7.85 (s, 1H, Ar); MS: m/e (ES−) 431 (M−1).

EXAMPLE 37c

4-Bromo-3-(3-chloro-2-nitro-phenylmethanesulfonyl)-5-methylbenzoic acid methyl ester Metachloroperbenzoic acid (0.9 g, 5.6 mmol) was added in portions to a stirred solution of compound of Example 37b (0.484 g, 1.12 mmol) in dichloromethane (50 mL). The reaction mixture was stirred at 25° C. for 2 h and was concentrated to remove the solvent. The semisolid obtained was stirred with 10% sodium bicarbonate solution (100 mL). The solid obtained was filtered, washed with water (100 mL). The crude product obtained was purified by column chromatography (silica gel, 15% ethyl acetate in pet ether 60-80° C.) to obtain the title compound). Yield: 0.48 g, (92.30%); $^1$H NMR (DMSO-$d_6$, 300 MHz): δ 2.65 (s, 3H, $CH_3$), 3.95 (s, 3H, $OCH_3$), 5.15 (s, 2H, $CH_2$), 7.60 (d, 1H, Ar), 7.70 (t, 1H, Ar), 7.95 (s, 1H, Ar), 8.20 (s, 1H, Ar), 8.35 (s, 1H, Ar); MS: m/e (ES+) 463 (M+1).

EXAMPLE 37d 3-(2-Amino-3-chloro-phenylmethanesulfonyl)-4-bromo-5-methyl benzoic acid methyl ester Activated Raney-Nickel was added to a solution of compound of Example 37c (1.50 g, 3.46 mmol) in dimethylformamide (100 mL). The reaction mixture was subjected to hydrogenation (25 psi pressure) for 2 h. Catalyst was filtered-off, washed with dimethylformamide and concentrated to obtain the crude product, which was then purified by column chromatography (silica gel, 30% ethyl acetate in pet. ether 60-80° C.) to obtain the title compound. Yield: 0.785 g, (56.07%). MS: m/e (ES+) 433 (M+1).

EXAMPLE 37e

4-Chloro-6-methyl-10,10-dioxo-10,11-dihydro-5H-10lambda*6*-thia-5-aza-dibenzo[a,d]-cycloheptene-8-carboxylic acid methylester Sodium hydride (0.234 g, 5.07 mmol) was added in portions to a stirred solution of Example 37d (0.785 g, 1.69 mmol) in dry dimethylformamide (10 mL) at 0° C. The reaction mixture was stirred for 0.5 h. Excess sodium hydride was destroyed using methanol (5 mL). The reaction mixture was diluted with cold water (100 mL), the solid separated was filtered, crystallized using ethyl acetate/pet. ether 60-80° C. to obtain the title compound. Yield: 0.409 g, (64.10%); $^1$H NMR (DMSO-$d_6$, 300 MHz): δ 2.65 (s, 3H, $CH_3$), 3.90 (s, 3H, $OCH_3$), 5.15 (s, 2H, $CH_2$), 7.25 (t, 1H, Ar), 7.65 (d, 1H, Ar), 7.75 (d, 1H, Ar), 7.85 (s, 1H, NH), 8.05 (s, 1H, Ar), 8.35 (s, 1H, Ar); MS: m/e (EI) 351 (M+).

EXAMPLE 37f

4-Chloro-6-methyl-2-nitro-10,10-dioxo-10,11-dihydro-5H-10lambda*6*-thia-5-aza-dibenzo[a,d]-cycloheptene-8-carboxylic acid methylester Cooled sulfuric acid (1 mL) was added to a solution of compound of Example 37e (0.3 g, 0.85 mmol) in concentrated nitric acid (10 mL) at 0° C. The reaction mixture was stirred at 0° C. for 1.5 h. The reaction mixture was slowly poured in cold water (100 mL), solid obtained was filtered, washed with water till pH was neutral. Solid obtained was crystallized using ethyl acetate/pet. ether 60-80° C. to obtain the title compound. Yield: 0.31 g, (91.70%); $^1$H NMR (DMSO-$d_6$, 300 MHz): δ 2.70 (s, 3H, $CH_3$), 3.90 (s, 3H, $OCH_3$), 5.30 (s, 2H, $CH_2$), 8.10 (s, 1H, Ar), 8.15 (s, 1H, Ar), 8.35 (s, 1H, NH), 8.55 (s, 2H, Ar); MS: m/e (EI) 396 (M+).

EXAMPLE 38

4-Chloro-2-formylamino-6-methyl-10,10-dioxo-10,11-dihydro-5H-10-lambda*6*-thia-5-aza-dibenzo[a,d]-cycloheptene-8-carboxylic acid methyl ester Sodium formate (0.074 g, 0.108 mmol) was added to a suspension of compound of Example 37 (0.20 g, 0.547 mmol) in formic acid (2 mL) and refluxed for 1.5 h. The reaction mixture was cooled and poured into ice water (50 mL). The solid precipitated was filtered, washed with water and dried. The crude product was purified by trituration with chloroform/methanol (3:1) to obtain the title compound. Yield: 0.18 g (84%); mp: 280-282° C.; $^1$H NMR (DMSO-$d_6$, 300 MHz): δ 2.48 (s, 3H, $CH_3$), 3.82 (s, 3H, $OCH_3$), 4.91 (s, 2H, $CH_2$, trans minor isomer), 4.97 (s, 2H, CH$_2$, cis major isomer), 7.30 (d, 1H, Ar, trans minor isomer), 7.47 (d, 1H, Ar, trans minor isomer), 7.56 (s, 1H, Ar, cis major isomer), 7.63 (s, 1H, Ar, cis major isomer), 7.89 (s, 1H, Ar), 7.94 (s, 1H, Ar), 8.26 (s, 1H, CHO, cis major isomer), 8.29 (s, 1H, NH), 8.78 (d, 1H, CHO, trans minor isomer), 10.40 (d, 1H, NH, trans minor isomer), 10.46 (s, 1H, NH, cis major isomer); MS: m/e (ES+) 395 (M+1); analysis: C$_{17}$H$_{14}$ClNO$_6$S requires C, 51.72; H, 3.83; N, 7.10; Cl, 8.98; S, 8.12. found C, 51.24; H, 3.80; N, 6.79; Cl, 9.22; S, 7.84%.

EXAMPLE 39

5-10,10-Trioxo-10,11-dihydro-5H-10lambda*6*-thia-dibenzo[a,d]cycloheptene-8-carboxylic acid methyl ester Metachloroperbenzoic acid (1.96 g, 11.4 mmol) was added to a solution of compound of Example 39a (0.65 g, 2.28 mmol) in dichloromethane (20 mL) in two portions at 0° C. and the reaction mixture stirred at 25° C. for 2 h. The reaction mixture was concentrated, treated with sodium bicarbonate solution (50 mL) and extracted with ethyl acetate. The combined organic layer was washed with water, brine, dried, concentrated and purified using flash chromatography (silica gel, 1% methanol in chloroform) to obtain the title compound. Yield: 0.6 g (83%); $^1$H NMR (CDCl$_3$, 300 MHz): δ 4.00 (s, 3H, CH$_3$), 4.82 (s, 2H, CH$_2$), 7.29 (t, 1H, Ar), 7.59 (m, 1H, Ar), 7.85 (d, 1H, Ar), 8.02 (d, 1H, Ar), 8.10 (d, 1H, Ar), 8.35 (d, 1H, Ar), 8.71 (s, 1H, Ar); MS: m/e (EI) 316 (M+).

EXAMPLE 39a

5-Oxo-5,11-dihydro-10-thia-dibenzo[a,d]cycloheptene-8-carboxylic acid methyl ester The title compound was obtained using the reported procedure (J. Med. Chem., 21, 10, 1035, (1978)). Yield: 55%; $^1$H NMR (CDCl$_3$, 300 MHz): δ 3.93 (s, 3H, OCH$_3$), 4.08 (s, 2H, CH$_2$), 7.27 (d, 1H, Ar), 7.36 (t, 1H, Ar), 7.49 (t, 1H, Ar), 7.6 (d, 1H, Ar), 7.85 (d, 1H, Ar), 8.00 (s, 1H, Ar), 8.23 (s, 1H, Ar); MS: m/e (EI) 284 (M+).

EXAMPLE 40

5-Hydroxy-10,10-dioxo-10,11-dihydro-5H-10lambda*6*-thia-dibenzo[a,d]cycloheptene-8-carboxylic acid methyl ester Platinum oxide (0.015 g, 10% w/w) was added to a solution of compound of Example 39 (0.15 g, 0.47 mmol) in ethanol (50 mL) and acetic acid (20 mL). The reaction mixture was subjected to hydrogenation at 100 psi of hydrogen at 65° C. for 11 h. It was cooled to 30° C. and filtered through high flow bed. The mixture was concentrated, diluted with water and extracted with ethyl acetate. The combined organic layer was washed with 10% sodium bicarbonate solution (15 ml), water, brine, concentrated and crystallized with ethyl acetate/pet. ether 60-80° C. to obtain the title compound. Yield: 125 mg (82%); $^1$H NMR (DMSO-d$_6$, 300 MHz): δ 3.87 (s, 3H, OCH$_3$), 5.23 (d, 1H, CH$_a$), 5.53 (d, 1H, CH$_{a'}$), 6.49 (d, 1H, CH$_b$), 6.49 (d, 1H, CH$_{b'}$), 7.33 (m, 2H, Ar), 7.48 (d, 1H, Ar), 7.57 (d, 1H, Ar), 8.00 (d, 1H, Ar), 8.17 (d, 1H, Ar), 8.25 (s, 1H, Ar); MS: m/e (CI) 319 (M+1).

EXAMPLE 41

10,10-Dioxo-10,11-dihydro-5H-10lambda*6*-thia-dibenzo[a,d]cyclo heptene-8-carboxylic acid methyl ester Pd/C (0.015 g, 10% w/w) and catalytic amount of perchloric acid was added to a solution of compound of Example 40 (0.11 g, 0.3 mmol) in acetic acid (60 mL). The reaction mixture was subjected to hydrogenation at 100 psi of hydrogen at 65° C. for 6.5 h. The reaction mixture was cooled to 25° C. and filtered through high flow bed. The filtrate was concentrated, diluted with water and extracted with ethyl acetate. The combined organic layer was washed with water, brine, concentrated and purified using flash chromatography (silica gel, ethyl acetate and pet. ether 60-80° C.) to obtain the title compound. Yield: 0.05 g (47%); $^1$H NMR (CDCl$_3$, 300 MHz): δ 3.90 (s, 3H, OCH$_3$), 4.32 (s, 2H, CH$_2$), 5.21 (s, 2H, CH$_2$) 7.38 (m, 5H, Ar), 8.09 (d, 1H, Ar), 8.61 (s, 1H, Ar); MS: m/e (CI) 303 (M+1).

The efficacy of the present compounds in inhibiting the activity of TNF-α can be determined by a number of pharmacological assays well known in the art and described below. The exemplified pharmacological assays, which follow, have been carried out with the compounds of the present invention and their salts.

In Vitro Screening to Identify Inhibitors of TNF-α

EXAMPLE 42

Primary Screening—Whole Blood Cell Culture Assay

TNF-α production by lipopolysaccharide (LPS) in whole blood was measured according to the method described by Wilson et al (J. Immunol. Methods, 139: 233-240, 1991). Briefly, blood was collected from healthy donors into potassium EDTA vacutainer tubes (Vacutest Plast/Becton Dickinson) and diluted with RPMI 1640 culture medium (Gibco BRL, Pasley, UK) containing 100 U/ml penicillin and 100 µg/ml streptomycin, (100× solution, Sigma Chemical Co. St Louis, Mo.) with no added serum. The white blood cell count was adjusted to 1×10$^6$ cells/ml and 100 µg/well of the diluted blood was transferred into 96-well culture plates. Following cell plating, 79 µl of culture medium and 1 µl of the test compounds (final concentration 1 µM) dissolved in DMSO (dimethylsulfoxide, Sigma, Mo., USA) was added to the cells. The final concentration of DMSO was adjusted to 0.5%. 1 µl of vehicle (0.5% DMSO) was used as control. Rolipram (100 µM) was used as a standard compound. The plates were incubated for 30 min at 37° C. in an atmosphere of 5% CO$_2$. Finally, 20 µl (10 µg/ml) per well of LPS (*Escherchia coli* 0127:B8, Sigma Chemical Co., St. Louis, Mo.) was added, for a final concentration of 1 µg/ml. Plates were incubated at 37° C. for 4.5 h in an atmosphere of 5% CO$_2$. Supernatants were harvested and assayed for TNF-α by ELISA as described by the manufacturer (R&D Systems, MN) or by cytotoxicity bioassay in L929 cells. Percent inhibition of TNF-α release in comparison to the control was calculated.

The results are indicated in Table 1.

TABLE 1

| Example No. | % inhibition of TNF-α release |
|---|---|
| 06 | 89 |
| 09 | 31 |
| 11 | 51 |
| 16 | 41 |
| 24 | 74 |
| 26 | 85 |
| 28 | 70 |
| 29 | 76 |
| 31 | 66 |
| 32 | 96 |
| 33 | 95 |
| 35 | 45 |
| 37 | 33 |
| 38 | 45 |

The results indicate that the compounds of the present invention have inhibitory effects against TNF-α release.

EXAMPLE 43

Secondary Screening—Peripheral Blood Mononuclear Cells (PBMCs)

TNF-α production by LPS in peripheral blood mononuclear cells (PBMC) was measured according to the method described by Henry et al (J. Bioorg. Med. Chem. Lett. 8: 3335-3340, 1998). Briefly, blood was collected from healthy donors into Potassium EDTA vacutainer tubes (Vacutest Plast/Becton Dickinson). PBMC were isolated using gradient centrifugation in Ficoll-Paque solution (Pharmacia). Isolated PBMC were suspended in RPMI 1640 culture medium (Gibco BRL, Pasley, UK) containing 10% fetal bovine serum (FBS) (Hyclone, Utah, USA), 100 U/ml penicillin (Sigma Chemical Co. St Louis, Mo.) and 100 µg/ml streptomycin (Sigma Chemical Co. St Louis, Mo.). The cell concentration was adjusted to $1 \times 10^6$ cells/ml. The viability as determined by trypan blue dye exclusion was uniformly ≧98%. The cell suspension (100 µg) was added to the wells of a 96-well culture plate. Following cell plating, 79 µl of the culture medium and 1 µl of eight different concentrations of the test compounds (final concentration 0.03, 0.1, 0.3, 1, 3, 10, 30, 100 µM) dissolved in DMSO (dimethylsulfoxide, Sigma, Mo., USA) were added to the cells. The final concentration of DMSO was adjusted to 0.5%. The appropriate DMSO concentration was used as control. Rolipram (30 µM) was used as a standard compound. The plates were incubated for 30 min at 37° C. in an atmosphere of 5% $CO_2$. Finally, 20 µl (10 µg/ml) per well of LPS, (*Escherchia coli* 0127:B8, Sigma Chemical Co., St. Louis, Mo.) was added, for a final concentration of 1 µg/ml. The plates were incubated at 37° C. for 4.5 h in an atmosphere of 5% $CO_2$. To determine the cytotoxicity of the test compounds, the cell viability was assessed using MTS (3-(4,5-dimethylthiazol-2-yl)-5-(3-carboxymethoxyphenyl)-2-(4-sulfonyl)-2H-tetrazolium) reagent (Promega) after 4.5 h of incubation. Supernatants were harvested and assayed for TNF-α by ELISA as described by the manufacturer (R&D Systems, MN, BD Biosciences Pharmingen) or by cytotoxicity bioassay in L929 cells. The 50% inhibitory concentration ($IC_{50}$) values were calculated by a nonlinear regression method using GraphPad software (Prism 3.03)

The results are indicated in Table 2.

TABLE 2

| Example No. | $IC_{50}$ (µM) | % toxicity (10 µM), 5 h |
|---|---|---|
| 01 | 8.60 | 12 |
| 5A | 8.60 ± 1.30 | 00 |
| 5B | 9.10 ± 1.6 | 00 |
| 09 | 2.60 | 09 |
| 11 | 21.00 | 25 |
| 15 | 0.55 | 25 |
| 16 | 0.18 | 62 |
| 17 | 0.10 | 66 |
| 20 | 1.10 | 24 |
| 21 | 4.00 | 44 |
| 22 | 0.88 | 16 |
| 24 | 3.87 ± 1.42 | 03 |
| 25 | 0.60 | 18 |
| 26 | 8.05 ± 1.57 | 00 |
| 28 | 10.50 | 15 |
| 29 | 0.51 ± 1.58 | 23 |
| 31 | 0.84 | 21 |
| 32 | 0.16 | 27 |
| 33 | 0.20 | 29 |
| 35 | 1.40 | 07 |
| 38 | 1.20 ± 1.58 | 10 ± 04 |
| 40 | >10.00 | 8 |

The results indicate that the compounds of the present invention have inhibitory effects against TNF-α release with minimal toxicity.

The results indicate that the compounds of the present invention have inhibitory effects against TNF-α release with minimal toxicity.

EXAMPLE 44

Effect on Proinflammatory Cytokines Produced by Synovial Cells Obtained from a Rheumatoid Arthritis (RA) Patient Cytokine production by synovial cells obtained from a rheumatoid arthritis (RA) patient undergoing knee replacement surgery was measured according to the method described by Brennan, F. M. et al (The Lancet. July 29: 244-247, 1989). The synovial membrane tissue was digested in DMEM (Gibco) containing 10% FBS, 100 U/ml penicillin and 100 µg/ml streptomycin, 4 mg/ml collagenase type I (Worthington), 1.5 µg/ml Dnase type I (Sigma) and 15 U/ml heparin and incubated at 37° C. for 3 hours. After incubation, the digested tissue was filtered through a 70-µ membrane and the cells washed 3 times in complete medium (DMEM with 10% FBS). The synovial cells were cultured at $1 \times 10^6$ cells/ml in presence/absence of the test compound for 10 hours. The supernatants were harvested by centrifugation and levels of the cytokines (TNF-α, IL-1β, and IL-6) measured by ELISA. To assess the cytotoxic effect of the test compound, the cellular viability test was performed using MTS reagent.

Results: Compounds of the present invention were found to inhibit proinflammatory cytokines (TNF-α, IL-1β, and IL-6) produced by synovial cells obtained from a RA patient.

EXAMPLE 45

Effect on Proinflammatory Cytokines Released by LPS-Stimulated hPBMCs

The effect of the active molecules on the proinflammatory cytokines; interleukin-1β (IL-1β), interleukin-6 (IL-6) and interleukin-8 (IL-8) was measured using the supernatants generated in the primary screening assay [as described in Example 42]. The levels of these cytokines were estimated by ELISA as described by the manufacturer. (OptiEIA ELISA sets, BD Biosciences, Pharmingen). The 50% inhibitory concentration ($IC_{50}$) values were calculated by a nonlinear regression method using GraphPad software (Prism 3.03).

Results: Compounds of the present invention were found to inhibit proinflammatory cytokines interleukin-1β (IL-1β), interleukin-6 (IL-6) and interleukin-8 (IL-8) released by LPS-stimulated hPBMCs.

In Vivo Studies

EXAMPLE 46

Lipopolysaccharide (LPS)-Induced Tumor Necrosis Factor (TNF)-α Release in BALB/c Mice The protocol described by Fukuda T. et al (Eur. J. Pharmacol., 391: 317-320, 2000) was followed. BALB/c mice were divided into groups of five to ten each. The test compound, suspended in Tween 80-0.5% carboxy methylcellulose (CMC), with a few drops of Tween 80 as wetting agent if necessary, was administered orally (p.o.) to the mice. One hour later, LPS dissolved in sterile, pyrogen-free saline was administered i.p. at the dose of 1 mg/kg. The negative control group received saline as an i.p injection, while all other groups received LPS. Rolipram (30 mg/kg) was used as the standard drug. One and a half hours later, blood was collected in heparin. Plasma was separated by centrifugation at 13000 rpm (Heraeus Biofuge Pico Centrifuge) at room temperature, aliquoted and stored at −70° C. until analysis.

TNF-α levels in the blood samples were assayed using ELISA and % inhibition of TNF-α release compared to the control group was calculated.

The results are indicated in Table 4.

TABLE 4

| Example No. | Dose (mg/kg, po) | % inhibition (Mean ± SE*) | n** |
|---|---|---|---|
| 1 | 10 | 64.86 ± 3.97 | 5 |
| 3 | 100 | 40.72 ± 12.66 | 6 |
| 7 | 100 | 55.84 ± 9.24 | 5 |
| 11 | 100 | 77.87 ± 9.85 | 5 |
| 16 | 100 | 72.19 ± 3.17 | 10 |
| 18 | 100 | 22.66 ± 8.47 | 10 |
| 20 | 30 | 27.87 ± 17.52 | 5 |
| 21 | 30 | 54.56 ± 11.7 | 5 |
| 22 | 100 | 57.66 ± 5.66 | 10 |
| 24 | 30 | 17.56 ± 8.72 | 10 |
| 25 | 30 | 33.57 ± 16.46 | 5 |
| 26 | 100 | 68.68 ± 3.68 | 10 |
| 29 | 100 | 79.08 ± 0.91 | 10 |

*standard error
**number of BALB/c mice used in the experiment

The results indicate that the compounds of the present invention exhibit good in vitro and in vivo TNF-α inhibitory activity.

We claim:
1. A compound of formula (1a):

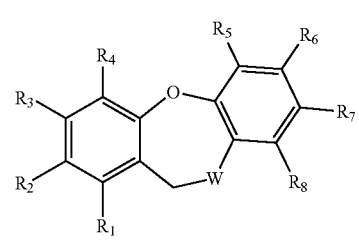

wherein
$R_1$, $R_2$, $R_3$, $R_4$, $R_5$, $R_6$ and $R_8$ are each independently selected from: hydrogen, halogen, hydroxy, alkyl, alkenyl, cycloalkyl, alkoxy, cyano, nitro, trifluoromethyl, aryl, heterocyclyl, heteroaryl, alkylsulfonyl, heterocyclylsulfonyl, heteroarylsulfonyl, —S(O)$_2$—NH-heterocyclyl, —S(O)$_2$—NH-heteroaryl, sulfonamide, —S(O)$_2$—NH-alkyl, —S(O)$_2$—NH-cycloalkyl, —S(O)$_2$—NH-aryl, —NH—S(O)$_2$-alkyl, —NH—S(O)$_2$-cycloalkyl, —NH—S(O)$_2$-aryl, —NH—S(O)$_2$-heterocyclyl, —NH—S(O)$_2$-heteroaryl, $NR_{11}R_{12}$, hydrazine and
$R_7$ is alkyl, —(CH$_2$)$_n$C(O)R$_9$ or —C(O)NR$_{11}$R$_{12}$;
$R_9$ is hydrogen, halogen, alkyl, cycloalkyl, trifluoromethyl, OR$_{10}$, aryl or heterocyclyl;
$R_{10}$ is hydrogen, alkyl, cycloalkyl, trifluoromethyl, aryl or heterocyclyl;
$R_{11}$ and $R_{12}$ are each independently selected from: hydrogen, alkyl, cycloalkyl, alkylamino, aryl, heteroaryl, heterocyclyl, —(CH$_2$)$_n$C(O)R$_9$ and cycloalkylaminoalkylcarbonyl; or $R_{11}$ and $R_{12}$, together with the N atom to which they are bonded, form a 5-, 6-, 7- or 8-membered heterocyclyl, optionally having one or more additional heteroatoms selected from: O, N and S;
R' is heterocyclyl or cycloalkyl;
n is 0, 1 or 2;
where alkyl or cycloalkyl is unsubstituted or substituted by one or two of the same or different groups selected from: halogen, hydroxy, alkylcarboxy, amino, cycloalkyl, alkoxy, aryloxy, alkoxylcarbonyl, arylalkoxycarbonyl, aminocarbonyl, alkylamino, dialkylamino, cycloalkylamino, cycloalkyl alkylamino, heterocyclyl alkylamino, heteroarylamino, heteroarylalkylamino, dialkylamino, alkylamino, aryl, amino aryl, heteroaryl and heterocyclyl;
heterocyclyl is unsubstituted or substituted by one or two of the same or different groups selected from: halogen, hydroxy, alkoxy, oxo, alkyl, cycloalkyl, cycloalkyl alkyl, aryl, hydroxyalkyl, amino, aminoalkyl, alkylaminoalkyl, heterocyclyl alkyl, heteroaryl alkyl, aralkyl, alkylheteroaryl, cycloalkylheteroaryl, formyl, alkylcarbonyl, alkoxycarbonyl, aryl alkoxycarbonyl, cycloalkylcarbonyl, arylcarbonyl, heteroarylcarbonyl, —SH, —S-alkyl, —S(O)$_2$-alkyl, —S(O)$_2$-aryl, alkylheteroaryl, alkylamino and alkylheteroarylamino;
aryl is unsubstituted or substituted by one or two of the same or different groups selected from: halogen, nitro, alkyl, trifluoromethyl, alkoxy, amino, mono- or di-alkylamino, heteroaryl alkyl and aralkyl;
heteroaryl is unsubstituted or substituted by one or two of the same or different groups selected from: halogen, alkyl, cycloalkyl, nitro and amino;

W is S(O)$_m$; and
m is 1 or 2;
in all its stereoisomeric and tautomeric forms and mixtures thereof in all ratios, and its pharmaceutically acceptable salts and solvates.

2. A compound of formula 1a,

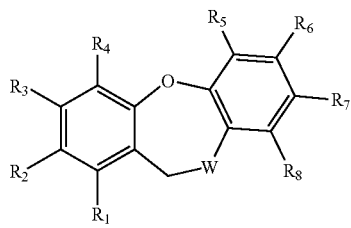

1a wherein
$R_1$ is hydrogen, $C_1$-$C_4$ alkyl or halogen;
$R_2$ is hydrogen, halogen, amino, nitro, cyano, heterocyclyl, heterocyclyl$C_1$-$C_4$alkylheterocyclyl, amino$C_1$-$C_4$ alkylheterocyclyl, aryl $C_1$-$C_4$ alkylheterocyclyl, heteroarylbenzyl $C_1$-$C_4$ alkylheterocyclyl, heteroaryl $C_1$-$C_4$ alkylheterocyclyl, di($C_1$-$C_4$ alkyl)benzylheterocyclyl, $C_3$-$C_6$ cycloalkylheterocyclyl, $C_3$-$C_6$cycloalkyl heteroaryl, heteroarylcarbonylheterocyclyl, heterocyclylsulfonyl, —S(O)$_2$—NH-heterocyclyl, $C_1$-$C_4$ alkylsulfonyl, $C_1$-$C_4$ alkoxy, $C_3$-$C_6$ cycloalkyl$C_1$-$C_4$alkyl, —NR$_{11}$R$_{12}$, NHR$_{16}$ or N=heterocyclyl;
$R_3$ is hydrogen, NR$_{11}$R$_{12}$ or NHR$_{16}$;
$R_4$ and $R_5$ are each independently selected from: hydrogen, halogen, $C_1$-$C_4$ alkyl, nitro, amino, halo$C_1$-$C_4$alkylamino and heterocyclyl $C_1$-$C_4$ alkylamino;
$R_6$ and $R_8$ are each independently selected from: hydrogen, $C_1$-$C_4$ alkyl and halogen;
$R_7$ is hydroxy $C_1$-$C_4$ alkyl, chloro $C_1$-$C_4$ alkyl, cyano $C_1$-$C_4$ alkyl, formyl, —(CH$_2$).C(O)OR$_{10}$ or CONHR$_{16}$;
$R_{10}$ is hydrogen, $C_1$-$C_4$ alkyl, amino $C_1$-$C_4$ alkyl, heterocyclyl $C_1$-$C_4$ alkyl, aryl, heteroaryl or heterocyclyl;
$R_{11}$ and $R_{12}$ are each independently selected from: hydrogen, $C_1$-$C_4$ alkyl, hydroxy $C_1$-$C_4$ alkyl, halo$C_1$-$C_4$ alkyl, amino$C_1$-$C_4$ alkyl, aryl$C_1$-$C_4$ alkyl, $C_3$-$C_6$cycloalkyl$C_1$-$C_4$alkyl, $C_6$-$C_{10}$ aryl, heterocyclyl or heteroaryl; or $R_{11}$ and $R_{12}$, together with the N atom to which they are bonded, form a 6- or 7-membered heterocyclyl, optionally having one or more additional N or O heteroatoms;
$R_{16}$ is formyl, $C_1$-$C_4$ alkyl, $C_3$-$C_6$cycloalkyl, heterocyclyl$C_1$-$C_4$alkyl, heteroaryl $C_1$-$C_4$alkyl, heteroarylamino $C_1$-$C_4$ alkyl, di ($C_1$-$C_4$)alkyl amino $C_1$-$C_4$ alkyl, amino $C_1$-$C_4$ alkyl, heterocyclyl $C_1$-$C_4$alkylamino $C_1$-$C_4$ alkyl, halo $C_1$-$C_4$ alkyl, di ($C_1$-$C_4$)alkyl amino $C_1$-$C_4$ alkyl amino $C_1$-$C_4$alkyl, carboxy ($C_1$-$C_4$)alkyl, hydroxy $C_1$-$C_4$ alkyl, trifluoromethylcarbonyl, di ($C_1$-$C_4$alkyl) amino $C_1$-$C_4$alkylcarbonyl, $C_3$-$C_6$ cycloalkylamino$C_1$-$C_4$alkylcarbonyl, halo $C_1$-$C_4$alkylcarbonyl, hydroxy $C_1$-$C_4$ alkylcarbonyl, $C_1$-$C_4$ alkylcarbonyl, $C_1$-$C_4$ alkyl amino$C_1$-$C_4$alkylcarbonyl, $C_6$-$C_{10}$ aryl carbonyl, benzyloxycarbonyl, halo carbonyl $C_1$-$C_4$alkylcarbonyl, amino carbonyl $C_1$-$C_4$alkylcarbonyl, $C_1$-$C_4$alkoxycarbonyl $C_1$-$C_4$alkylcarbonyl, $C_1$-$C_4$alkylcarbonyloxy $C_1$-$C_4$alkylcarbonyl or heterocyclyl $C_1$-$C_4$ alkylcarbonyl;
n is 0, 1 or 2;
where heterocyclyl is unsubstituted or substituted by one or two of the same or different groups selected from: halogen, hydroxy, alkoxy, oxo, $C_1$-$C_4$ alkyl, $C_3$-$C_6$ cycloalkyl, $C_3$-$C_6$ cycloalkyl $C_1$-$C_4$ alkyl, $C_6$-$C_{10}$ aryl, hydroxy $C_1$-$C_4$ alkyl, amino, amino $C_1$-$C_4$ alkyl, $C_1$-$C_4$ alkylamino $C_1$-$C_4$ alkyl, heterocyclyl $C_1$-$C_4$ alkyl, heteroaryl $C_1$-$C_4$alkyl, $C_6$-$C_{10}$ aryl $C_1$-$C_4$ alkyl, $C_1$-$C_4$ alkylheteroaryl, $C_3$-$C_{10}$ cycloalkylheteroaryl, formyl, $C_1$-$C_4$alkylcarbonyl, $C_1$-$C_4$ alkoxycarbonyl, $C_6$-$C_{10}$ aryl $C_1$-$C_4$ alkoxycarbonyl, $C_6$-$C_{10}$ arylcarbonyl, $C_3$-$C_{10}$ cycloalkylcarbonyl, heteroarylcarbonyl, —SH, —S—$C_1$-$C_4$ alkyl, —S(O)$_2$—$C_1$-$C_4$ alkyl, —S(O)$_2$—$C_6$-$C_{10}$ aryl, $C_1$-$C_4$ alkylamino and $C_1$-$C_4$ alkylheteroarylamino;
aryl is unsubstituted or substituted by one or two of the same or different groups selected from: halogen, nitro, $C_1$-$C_4$alkyl, trifluoromethyl, $C_1$-$C_4$ alkoxy, amino, mono- or di-$C_1$-$C_4$ alkylamino, heteroaryl $C_1$-$C_4$ alkyl and $C_6$-$C_{10}$ar$C_1$-$C_4$ alkyl; and
heteroaryl is unsubstituted or substituted by one or two of the same or different groups selected from: halogen, $C_1$-$C_4$ alkyl, $C_3$-$C_4$ cycloalkyl, nitro and amino;
W is S(O)$_m$; and
m is 1 or 2;
in all its stereoisomeric and tautomeric forms and mixtures thereof in all ratios, and its pharmaceutically acceptable salts and solvates.

3. A compound according to claim 1, wherein
$R_2$ is hydrogen, halogen, nitro, amino, cyano, $C_1$-$C_4$alkyl, $C_1$-$C_4$alkoxy, morpholinyl, 1,4-diazepanyl, 4-cyclopropyl-2-oxo-piperazinyl, piperazinyl, N-formyl piperazinyl, $C_1$-$C_4$ alkylcarbonyl piperazinyl, $C_1$-$C_4$alkyl piperazinyl, hydroxy $C_1$-$C_4$alkyl piperazinyl, $C_1$-$C_4$alkyl sulfonyl piperazinyl, $C_3$-$C_6$ cycloalkyl piperazinyl, benzyl piperazinyl, $C_1$-$C_4$ alkoxycarbonyl piperazinyl, $C_6$-$C_{10}$ aryl $C_1$-$C_4$ alkoxycarbonyl piperazinyl, $C_6$-$C_{10}$ arylcarbonyl piperazinyl, amino$C_1$-$C_4$alkyl piperazinyl, substituted phenyl $C_1$-$C_4$alkyl piperazinyl, imidazolylbenzyl $C_1$-$C_4$alkyl piperazinyl, $C_3$-$C_6$cycloalkylthiadiazolylpiperazinyl, pyrrolylcarbonylpiperazinyl, furanyl$C_1$-$C_4$ alkylpiperazinyl, dimethylaminobenzylpiperazinyl, thiophenyl$C_1$-$C_4$ alkylpiperazinyl, morpholinyl$C_1$-$C_4$alkyl piperazinyl, $C_1$-$C_4$alkyl sulfonyl, piperazinylsulfonyl, isooxazolylaminosulfonyl, formyl amino, $C_1$-$C_4$ alkylamino, dimethyl amino, $C_1$-$C_4$ alkylcarbonylamino, dimethylamino $C_1$-$C_4$alkylcarbonylamino, $C_3$-$C_6$ cycloalkylamino$C_1$-$C_4$alkylcarbonyl amino, hydroxy $C_1$-$C_4$alkylcarbonylamino, $C_1$-$C_4$alkylcarbonyloxy $C_1$-$C_4$alkylcarbonylamino, chloro $C_1$-$C_4$alkylcarbonylamino, morpholinyl $C_1$-$C_4$ alkylcarbonylamino, trifluoromethylcarbonylamino, benzyloxycarbonylamino, piperazinyl$C_1$-$C_4$alkylamino, phenylalkylamino, imidazolylamino $C_1$-$C_4$ alkyl amino, imidazolyl $C_1$-$C_4$ alkyl amino, dimethylamino $C_1$-$C_4$ alkylamino, isobutylamino, amino $C_1$-$C_4$ alkylamino, morpholinyl $C_1$-$C_4$alkylamino $C_1$-$C_4$ alkylamino, morpholinyl $C_1$-$C_4$ alkylamino, $C_3$-$C_6$ cycloalkyl$C_1$-$C_4$alkylamino, chloro $C_1$-$C_4$alkylamino, dimethylamino$C_1$-$C_4$ alkylamino $C_1$-$C_4$ alkylamino, carboxy $C_1$-$C_4$ alkylamino, hydroxy $C_1$-$C_4$ alkylamino, di(hydroxy $C_1$-$C_4$ alkyl)amino, di(chloro$C_1$-$C_4$alkyl)amino, benzyloxycarbonyl$C_1$-$C_4$alkylamino, NR$_{11}$R$_{12}$ or pyrrolidin-2ylidene;
$R_{11}$ and $R_{12}$ are each independently selected from: hydrogen, $C_1$-$C_4$ alkyl, morpholinyl $C_1$-$C_4$alkyl, $C_6$-$C_{10}$ aryl $C_1$-$C_4$ alkyl, $C_3$-$C_6$cycloalkyl$C_1$-$C_4$alkyl, hydroxy $C_1$-$C_4$ alkyl, chloro $C_1$-$C_4$alkyl, $C_6$-$C_{10}$ aryl, heterocyclyl and heteroaryl;

where
heterocyclyl is substituted with $C_1$-$C_4$ alkyl; and
aryl is substituted with one or two of the same or different groups selected from: halogen, trifluoromethyl, $C_1$-$C_4$ alkyl, $C_1$-$C_4$ alkoxy and mono- or di-substituted amino;
$R_3$ is hydrogen, amino, $C_1$-$C_4$alkylamino, amino $C_1$-$C_4$alkylamino, unsubstituted piperazinyl or piperazinyl substituted by $C_1$-$C_4$alkyl;
$R_4$ is hydrogen or halogen; $R_5$ is hydrogen or $C_1$-$C_4$ alkyl; and
$R_7$ is $C(O)OC_1$-$C_4$ alkyl, $C(O)OH$, $CH_2C(O)OC_1$-$C_4$ alkyl, $CH_2C(O)OH$, formyl, hydroxy $C_1$-$C_4$ alkyl, chloro $C_1$-$C_4$ alkyl, cyano $C_1$-$C_4$ alkyl or —$C(O)NH$ $C_3$-$C_6$ cycloalkyl;
W is $S(O)_m$; and
m is 1 or 2.

4. A compound according to claim 3, wherein
$R_2$ is amino, formylamino, $C_1$-$C_4$alkylamino, $C_1$-$C_4$alkylcarbonylamino, chloro $C_1$-$C_4$alkylcarbonylamino, hydroxy $C_1$-$C_4$alkylcarbonylamino, $C_1$-$C_4$alkylcarbonyloxy$C_1$-$C_4$alkylcarbonylamino, carboxy$C_1$-$C_4$alkylamino, di(chloro$C_1$-$C_4$alkyl)amino, di(hydroxy$C_1$-$C_4$alkyl) amino, acetamide, propionamide, morpholinyl, [1,4]diazepanyl, unsubstituted piperazinyl or piperazinyl substituted by at least one group selected from: $C_1$-$C_4$alkyl, $C_3$-$C_6$cycloalkyl, formyl, $C_1$-$C_4$alkylcarbonyl, hydroxy $C_1$-$C_4$alkyl, $C_1$-$C_4$alkylsulfonyl, benzyl, oxo, $C_1$-$C_4$ alkoxycarbonyl, benzyloxycarbonyl, unsubstituted $C_6$-$C_{10}$ arylcarbonyl or $C_6$-$C_{10}$ arylcarbonyl substituted by at least one group selected from: $C_1$-$C_4$alkyl, $C_1$-$C_4$alkoxy, halogen and trifluoromethyl;
$R_3$ is hydrogen;
$R_4$ is halogen; $R_5$ is $C_1$-$C_4$ alkyl; and
$R_7$ is $C(O)OC_1$-$C_4$ alkyl, $C(O)OH$, $CH_2C(O)OC_1$-$C_4$ alkyl or $CH_2C(O)OH$;
W is $S(O)_m$; and
m is 1 or 2.

5. A compound according to claim 3, wherein
$R_1$ and $R_2$ are hydrogen;
$R_3$ is amino, amino $C_1$-$C_4$alkylamino, unsubstituted piperazinyl or piperazinyl substituted by $C_1$-$C_4$alkyl;
$R_4$ is chloro, bromo or fluoro;
$R_5$ is methyl or ethyl;
$R_6$ and $R_8$ are hydrogen; and
$R_7$ is $C(O)OC_1$-$C_4$ alkyl, or $C(O)OH$.

6. A compound according to claim 4, wherein
$R_1$ is hydrogen;
$R_2$ is unsubstituted piperazinyl or piperazinyl substituted by $C_1$-$C_4$alkyl, $C_3$-$C_6$cycloalkyl, formyl, $C_1$-$C_4$ alkylcarbonyl, hydroxy $C_1$-$C_4$alkyl, $C_1$-$C_4$alkylsulfonyl, benzyl, oxo, $C_1$-$C_4$ alkoxycarbonyl, benzyloxycarbonyl, unsubstituted $C_6$-$C_{10}$ arylcarbonyl or $C_6$-$C_{10}$ arylcarbonyl substituted by $C_1$-$C_4$alkyl;
$R_3$ is hydrogen;
$R_4$ is chloro, bromo or fluoro;
$R_5$ is methyl or ethyl; and
$R_6$ and $R_8$ are hydrogen.

7. A compound according to claim 1, wherein W is $SO_2$.

8. A compound according to claim 1, selected from:
(4-chloro-6-methyl-10,10-dioxo-2-piperazin-1-yl, 10,11-dihydro-5-oxa-10lambda*6*-thia-dibenzo[a,d]cycloheptene-8-yl) acetic acid methyl ester hydrochloride;
2-Amino-4-chloro-6-methyl-10,10-dioxo-10,11-dihydro-5-oxa-10lambda*6*-thia-dibenzo[a,d]cycloheptene-8-carboxylic acid methyl ester;
2-Amino-4-chloro-6-methyl-10,10-dioxo-10,11-dihydro-5-oxa-10lambda*6*-thia-dibenzo[a,d]cycloheptene-8-carboxylic acid;
2-Amino-4-chloro-6-methyl-10,10-dioxo-10,11-dihydro-5-oxa-10lambda*6*-thia-dibenzo[a,d]cycloheptene-8-carboxylic acid sodium salt;
4-Chloro-2-(2-chloro-acetylamino)-6-methyl-10,10-dioxo-10,11-dihydro-5-oxa-10lambda*6*-thia-dibenzo[a,d]cycloheptene-8-carboxylic acid methyl ester;
4-Chloro-2-(2-hydroxy-acetylamino)-6-methyl-10,10-dioxo-10,11-dihydro-5-oxa-10lambda*6*-thia-dibenzo[a,d]cycloheptene-8-carboxylic acid methyl ester;
2-(2-Acetoxy-acetylamino)-4-chloro-6-methyl-10,10-dioxo-10,11-dihydro-5-oxa-10lambda*6*-thia-dibenzo[a,d]cycloheptene-8-carboxylic acid methyl ester;
4-Chloro-6-methyl-10,10-dioxo-2-propionylamino-10,11-dihydro-5-oxa-10lambda*6*-thia-dibenzo[a,d]cycloheptene-8-carboxylic acid methyl ester;
4-Chloro-2-formylamino-6-methyl-10,10-dioxo-10,11-dihydro-5-oxa-10lambda*6*-thia-dibenzo[a,d]cycloheptene-8-carboxylic acid;
4-Chloro-2-formylamino-6-methyl-10,10-dioxo-10,11-dihydro-5-oxa-10lambda*6*-thia-dibenzo[a,d]cycloheptene-8-carboxylic acid sodium salt;
4-Chloro-2-formylamino-6-methyl-10,10-dioxo-10,11-dihydro-5-oxa-10lambda*6*-thia-dibenzo[a,d]cycloheptene-8-carboxylic acid methyl ester;
-Chloro-2-formylamino-6-methyl-10,10-dioxo-10,11-dihydro-5-oxa-10lambda*6*-thia-dibenzo[a,d]cycloheptene-8-carboxylic acid ethyl ester;
4-Chloro-2-formylamino-6-methyl-10,10-dioxo-10,11-dihydro-5-oxa-10lambda*6*-thia-dibenzo[a,d]cycloheptene-8-carboxylic acid isopropyl ester;
2-[Bis-(2-chloro-ethyl)amino]-4-chloro-6-methyl10,10-dioxo-10,11-dihydro-5-oxa-10lambda*6*-thia-dibenzo[a,d]-cycloheptene-8-carboxylic acid methyl ester;
2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carboxylic acid methyl ester;
4-Chloro-6-methyl-2-piperazin-1-yl-11H-5-oxa-10-thia-dibenzo[a,d]cyclo heptene-8-carboxylic acid methyl ester hydrochloride;
4-Chloro-6-methyl-10-oxo-2-piperazin-1-yl-10,11-dihydro-5-oxa-10lambda*4*-thia-dibenzo[a,d]cycloheptene-8-carboxylic acid methyl ester hydrochloride;
4-Chloro-6-methyl-10,10-dioxo-2-piperazin-1-yl-10,11-dihydro-5-oxa-10lambda*6*-thia-dibenzo[a,d]-cycloheptene-8-carboxylic acid methyl ester hydrochloride;
4-Chloro-6-methyl-10,10-dioxo-2-piperazin-1-yl-10,11-dihydro-5-oxa-10lambda*6*-thia-dibenzo[a,d]cycloheptene-8-carboxylic acid methyl ester mesylate;
4-Chloro-6-methyl-10,10-dioxo-2-piperazin-1-yl-10,11-dihydro-5-oxa-10lambda*6*-thia-dibenzo[a,d]cycloheptene-8-carboxylic acid;
4-Chloro-6-methyl-10,10-dioxo-2-piperazin-1-yl-10,11-dihydro-5-oxa-10lambda*6*-thia-dibenzo[a,d]cycloheptene-8-carboxylic acid mesylate;
4-Chloro-2-(4-formyl-piperazin-1-yl)-6-methyl-10,10-dioxo-10,11-dihydro-5-oxa-10lambda*6*-thia-dibenzo[a,d]cycloheptene-8-carboxylic acid methyl ester;
2-(4-Acetyl-piperazin-1-yl)-4-chloro-6-methyl-10,10-dioxo-10,11-dihydro-5-oxa-10lambda*6*-thia-dibenzo[a,d]cycloheptene-8-carboxylic acid methyl ester;

4-Chloro-2-[4-(2-hydroxy-ethyl)-piperazin-1-yl]-6-methyl-10,10-dioxo-10,11-dihydro-5-oxa-10lambda*6*-thia-dibenzo[a,d]cycloheptene-8-carboxylic acid methyl ester;

2-(4-Benzyl-piperazin-1-yl)-4-chloro-6-methyl-10,10-dioxo-10,11-dihydro-5-oxa-10lambda*6*-thia-dibenzo[a,d]cycloheptene-8-carboxylic acid methyl ester;

4-Chloro-6-methyl-2-[4-(2-methyl-benzoyl)-piperazin-1-yl]-10,10-dioxo-10,11-dihydro-5-oxa-10lambda*6*-thia-dibenzo[a,d]cycloheptene-8-carboxylic acid methyl ester;

4-Chloro-2-(4-methanesulfonyl-piperazin-1-yl)-6-methyl-10,10-dioxo-10,11-dihydro-5-oxa-10lambda*6*-thia-dibenzo[a,d]cycloheptene-8-carboxylic acid methyl ester;

4-(4-Chloro-8-methoxycarbonyl-6-methyl-10,10-dioxo-10,11-dihydro-5-oxa-10lambda*6*-thia-dibenzo[a,d]cyclohepten-2-yl)-piperazine-1-carboxylic acid benzyl ester;

4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carboxylic acid methyl ester hydrochloride;

4-Chloro-6-methyl-10,10-dioxo-2-piperazin-1-yl-10,11-dihydro-5-oxa-10lambda*6*-thia-dibenzo[a,d]cycloheptene-8-carboxylic acid isopropyl ester;

4-Chloro-2-[1,4]diazepan-1yl-6-methyl-10,10-dioxo-10,11-dihydro-5-oxa-10lambda*6*-thia-dibenzo[a,d]cycloheptene-8-carboxylic acid methyl ester hydrochloride;

4-Chloro-6-methyl-2-morpholin-4-yl-10,10-dioxo-10,11-dihydro-5-oxa-10lambda*6*-thia-dibenzo[a,d]cycloheptene-8-carboxylic acid methyl ester;

3-(2-Amino-ethylamino)-4-Chloro-6-methyl-10,10-dioxo-10,11-dihydro-5-oxa-10lambda*6*-thia-dibenzo[a,d]cycloheptene-8-carboxylic acid methyl ester hydrochloride;

4-Chloro-6-methyl-10,10-dioxo-3-piperazin-1-yl-10,11-dihydro-5-oxa-10lambda*6*-thia-dibenzo[a,d]cycloheptene-8-carboxylic acid methyl ester hydrochloride;

4-Chloro-6-methyl-10,10-dioxo-2-piperazin-1-yl-10,11-dihydro-5-oxa-10lambda*6*-thia-dibenzo[a,d]cycloheptene-8-carbaldehyde;

[4-Chloro-2-(4-ethyl-piperazin-1-yl)-6-methyl-10,10-dioxo-10,11-dihydro-5-oxa-10lambda*6*-thia-dibenzo[a,d]cycloheptene-8-yl]-methanol; or 4-Chloro-6-methyl-10,10-dioxo-2-piperazin-1-yl-10,11-dihydro-5-oxa-10lambda*6*-thia-dibenzo[a,d]cycloheptene-8-carboxylic acid cyclopropyl amide hydrochloride.

9. A process for the preparation of a compound of formula (1a):

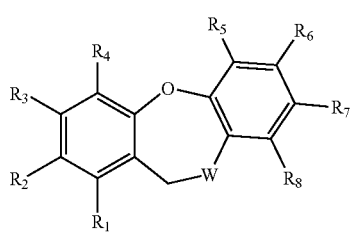

wherein,
W is $SO_2$ or SO; $R_2$, $R_3$, $R_4$, $R_5$ and $R_7$ are as defined in claim 1; $R_1$, $R_6$ and $R_8$ are H; which comprises, a) subjecting a compound of formula E:

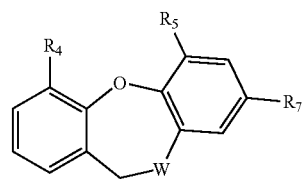

wherein W is $SO_2$ or SO as defined in formula (1a) and $R_4$, $R_5$ and $R_7$ are as defined above, to nitration to obtain a nitro compound of the general formula E1 or E1':

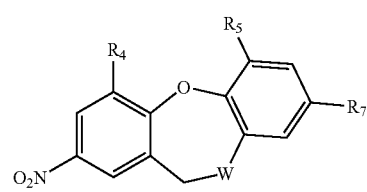

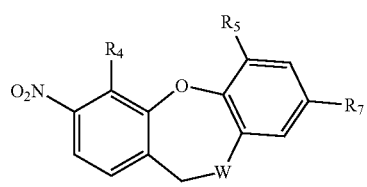

wherein W, $R_4$, $R_5$ and $R_7$ are as defined above;

b) subjecting the nitro compound of formula E1 or E1' above to reduction to obtain the corresponding amino compound of formula E2 or E2', respectively:

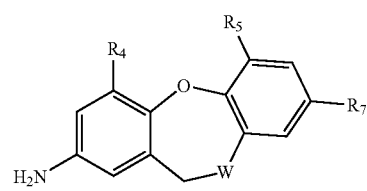

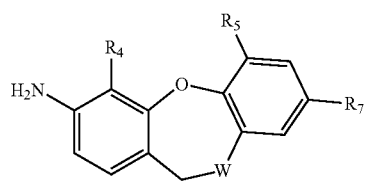

wherein W, $R_4$, $R_5$ and $R_7$ are as defined above;

c) subjecting the amino compound of formula E2 or E2' above to a reaction enabling conversion of the primary amino group in the compound of formula E2 into a group $R_2$ as defined above or to convert the primary amino group in the compound of formula E2' into a group $R_3$ as defined above and, optionally, converting the resulting compound into a pharmaceutically acceptable salt.

10. A process according to claim 9, wherein the compound of formula E is prepared by
subjecting a compound of formula D,

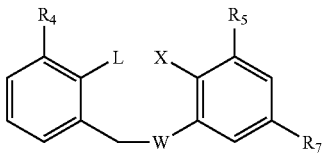

wherein $R_4$, $R_5$ and $R_7$ are as defined in claim 14; L is protected hydroxy group; and X is halogen, to deprotection to obtain the corresponding hydroxy compound, subjecting the hydroxy compound to cyclisation to obtain a compound of formula E, wherein $R_4$, $R_5$ and $R_7$ are as defined herein above; and U is O.

11. A pharmaceutical composition, comprising a therapeutically effective amount of a compound of formula (1a) according to claim 1 or a tautomer, stereoisomer, pharmaceutically acceptable salt, or pharmaceutically acceptable solvate thereof, and a pharmaceutically acceptable carrier or diluent.

12. A pharmaceutical composition, comprising a therapeutically effective amount of a compound of formula (1a) according to claim 1, or a tautomer, stereoisomer, pharmaceutically acceptable salt, or pharmaceutically acceptable solvate thereof, and at least one further pharmaceutically active compound, together with a pharmaceutically acceptable carrier or diluent.

13. A process for producing a pharmaceutical composition, comprising bringing into a suitable administration form at least one compound of formula (1a) according to claim 1 or a tautomer, stereoisomer, pharmaceutically acceptable salt, or solvate thereof, with a pharmaceutically suitable and physiologically tolerable excipient and, optionally active compounds, additives or auxiliaries.

14. A compound according to claim 5, wherein W is $SO_2$.

* * * * *